US008238516B2

(12) United States Patent
Sakurai et al.

(10) Patent No.: US 8,238,516 B2
(45) Date of Patent: Aug. 7, 2012

(54) RADIOTHERAPY SUPPORT APPARATUS

(75) Inventors: Yasuo Sakurai, Otawara (JP); Yoichi Takada, Otawara (JP); Masahiro Kumakura, Otawara (JP); Shigeharu Ohyu, Yaita (JP); Motoji Haragashira, Utsunomiya (JP); Kyojiro Nambu, Nasushiobara (JP); Mariko Shibata, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 98 days.

(21) Appl. No.: 12/349,680

(22) Filed: Jan. 7, 2009

(65) Prior Publication Data

US 2009/0175418 A1 Jul. 9, 2009

(30) Foreign Application Priority Data

Jan. 9, 2008 (JP) ................................ 2008-002370
Jan. 9, 2008 (JP) ................................ 2008-002371
Jan. 9, 2008 (JP) ................................ 2008-002372

(51) Int. Cl.
*A61N 5/10* (2006.01)

(52) U.S. Cl. ........................................................ 378/65

(58) Field of Classification Search ...................... 378/65
See application file for complete search history.

(56) References Cited

U.S. PATENT DOCUMENTS

| | | | |
|---|---|---|---|
| 6,298,115 B1 * | 10/2001 | Nilsson | 378/65 |
| 7,460,640 B2 | 12/2008 | Kamikonya et al. | |
| 2001/0017907 A1 * | 8/2001 | Tarr | 378/65 |
| 2001/0033682 A1 * | 10/2001 | Robar et al. | 378/65 |
| 2003/0007601 A1 * | 1/2003 | Jaffray et al. | 378/65 |
| 2006/0064014 A1 * | 3/2006 | Falco et al. | 600/439 |
| 2007/0058778 A1 * | 3/2007 | Coleman et al. | 378/65 |
| 2007/0071169 A1 * | 3/2007 | Yeo et al. | 378/65 |
| 2009/0161818 A1 | 6/2009 | Sakurai et al. | |

FOREIGN PATENT DOCUMENTS

| | | |
|---|---|---|
| JP | 5-156526 | 6/1993 |
| JP | 7-148276 | 6/1995 |
| JP | 9-99109 | 4/1997 |
| JP | 2003-210596 | 7/2003 |
| JP | 2007-130448 | 5/2007 |
| JP | 2007-331108 | 12/2007 |
| JP | 2008-26733 | 2/2008 |
| JP | 2008-33361 | 2/2008 |
| JP | 2008-33362 | 2/2008 |
| WO | WO 99/39628 A | 8/1999 |
| WO | WO 01/10299 A1 | 2/2001 |

* cited by examiner

*Primary Examiner* — Glen Kao
(74) *Attorney, Agent, or Firm* — Oblon, Spivak, McClelland, Maier & Neustadt, L.L.P.

(57) ABSTRACT

A radiotherapy treatment support apparatus includes a storage unit which stores absorption dose volume data expressing a spatial distribution of absorption dose in a subject, a generation unit which generates fusion data associated with morphology volume data of the subject and the absorption dose volume data so as to be associated with a plurality of segments, and a display unit which displays an image which has the distribution of absorption dose superimposed on the two-dimensional morphology image of the subject using the fusion data.

4 Claims, 42 Drawing Sheets

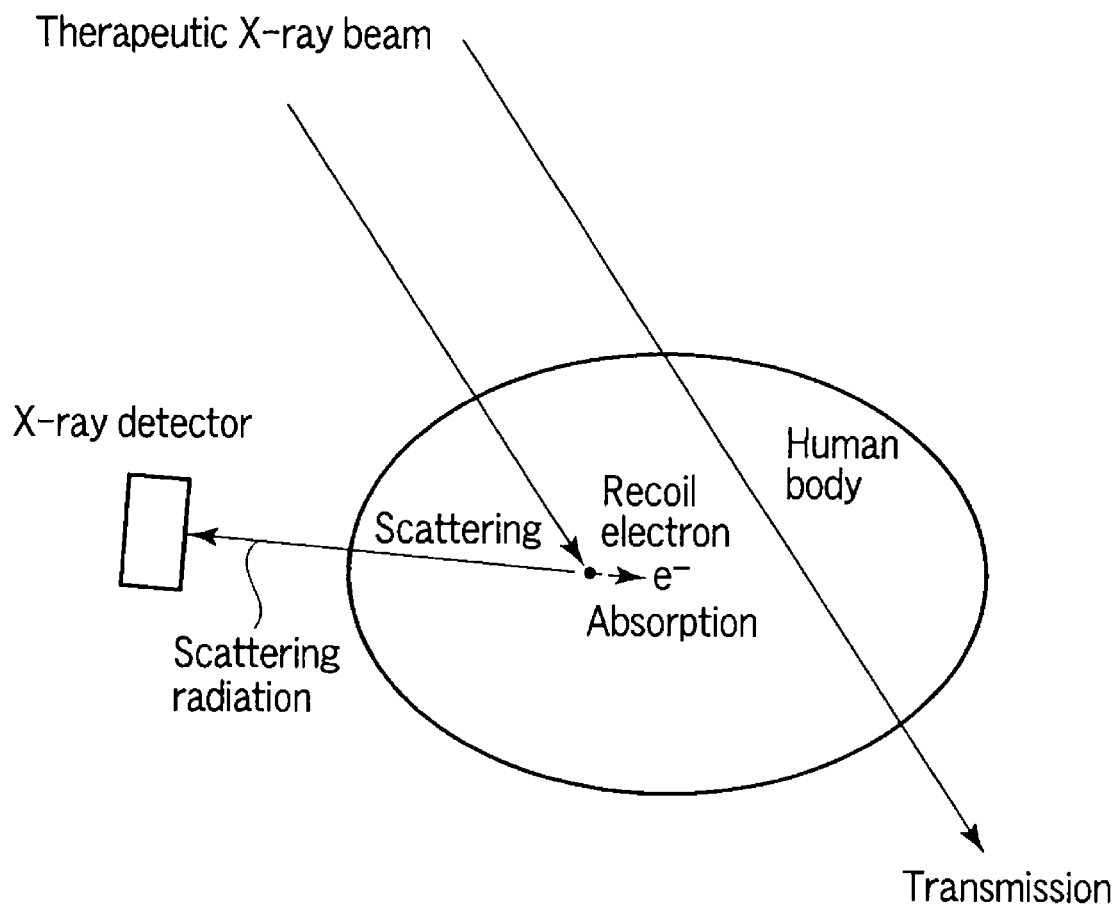
F I G. 1

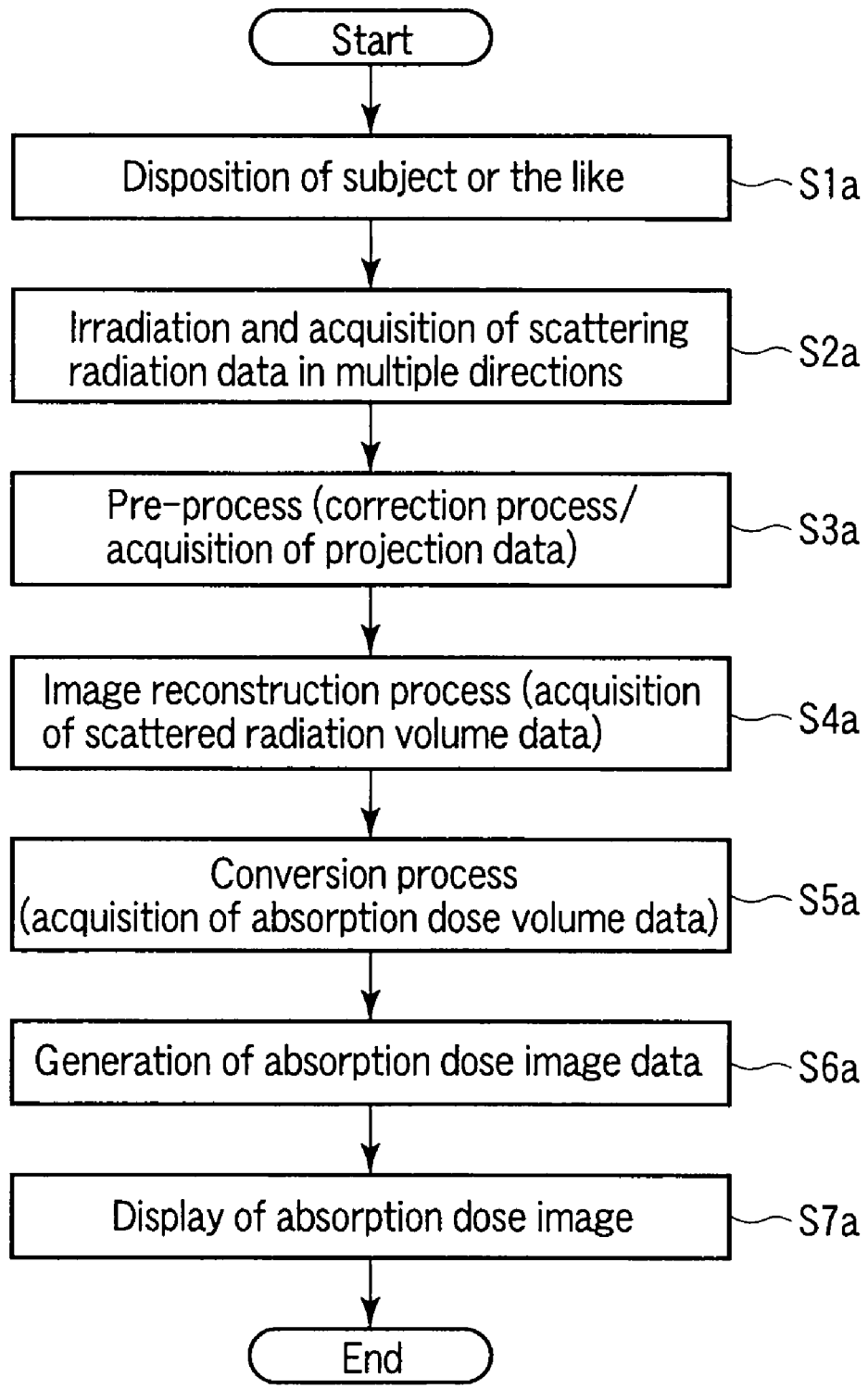
F I G. 5

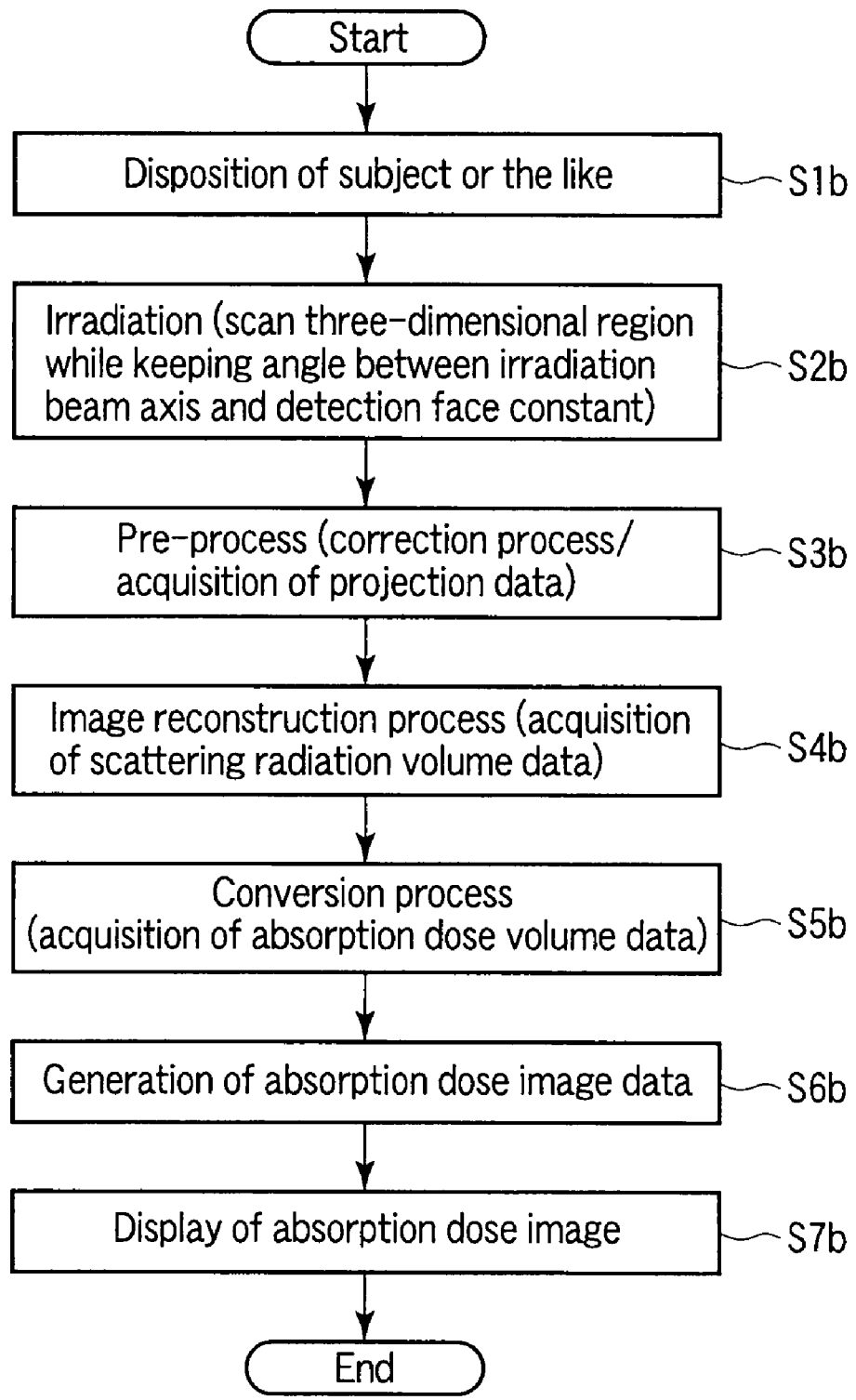
F I G. 7

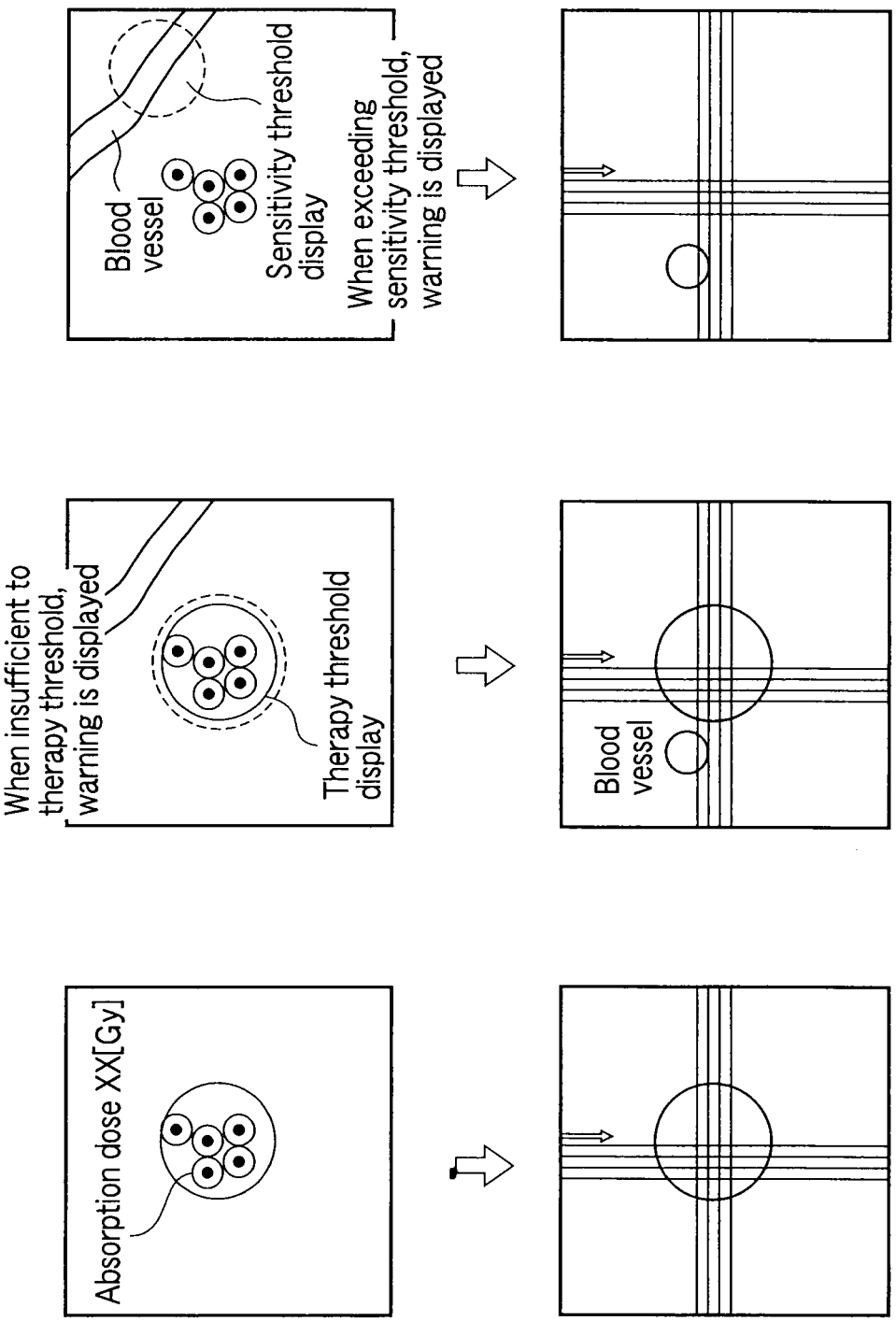

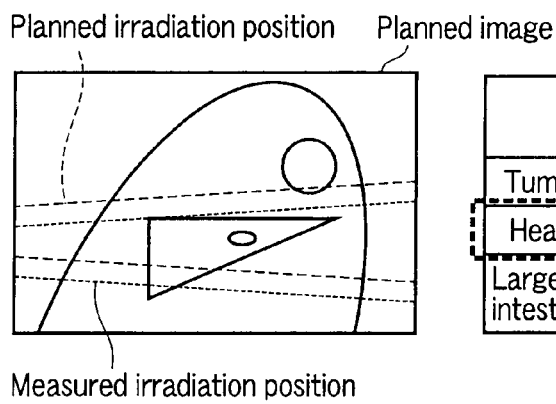
Planned irradiation position    Planned image
Measured irradiation position
F I G. 16A
| | Planned value | Measured value | Determination |
|---|---|---|---|
| Tumor | 5.2 | 4.8 | △− |
| Heart | 0.5 | 0.0 | ○ |
| Large intestine | 2.3 | 2.5 | △+ |
F I G. 16B
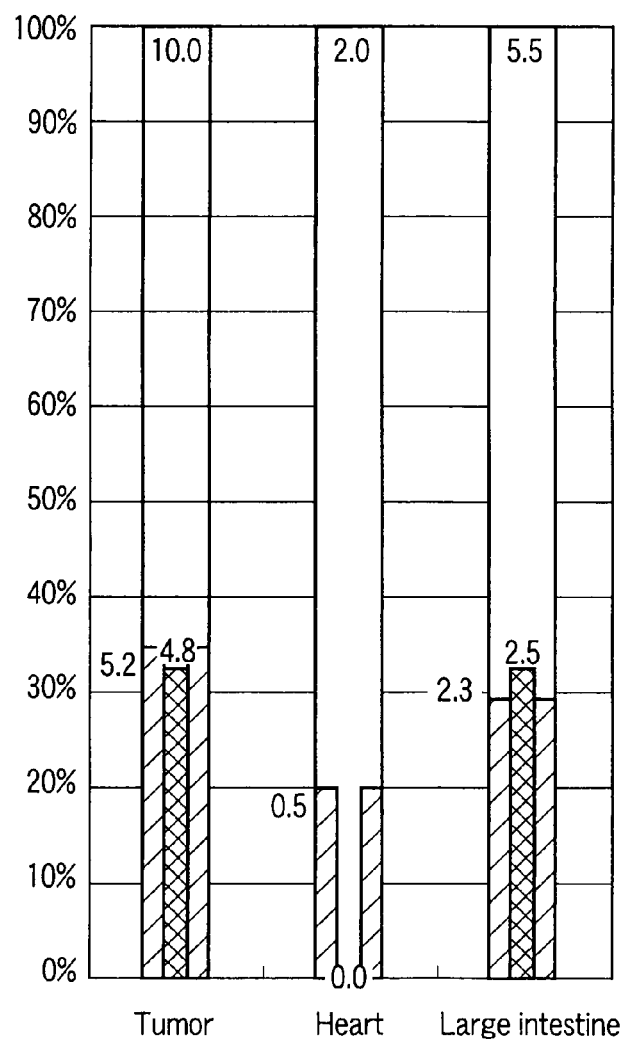
F I G. 16C

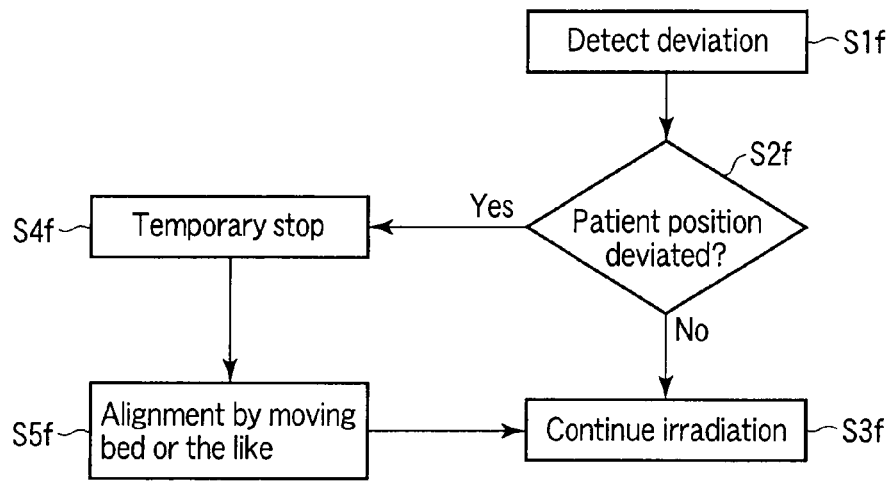
FIG. 20
| | Tumor | Heart | Large intestine |
|---|---|---|---|
| Measured value of first time | 5.0 | 0.5 | 0.5 |
| Measured value of second time | 2.5 | 1.0 | 2.5 |
| Present total irradiation dose | 7.5 | 1.5 | 3.0 |
| Planned value of third time | 2.5 | 0.6 | 2.5 |
| Total irradiation dose of next time | 10.0 | 2.1 | 5.5 |
FIG. 22
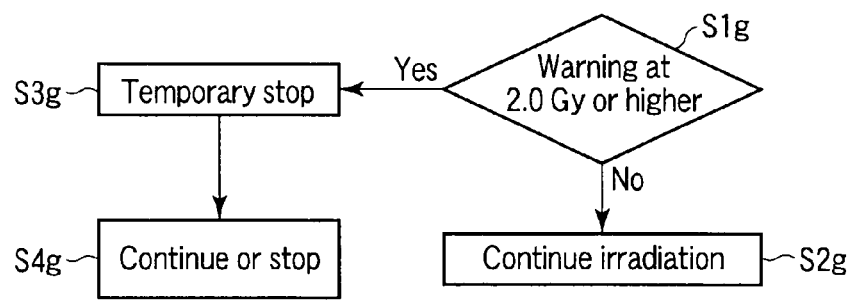
FIG. 23

| Region | Number of voxels | Region name | Total permissible dose |
|---|---|---|---|
| a | | Liver malignancy (GTV+CTV) | 70Gy or more each |
| b | | Margin | About 60 Gy each |
| c | | Liver normal tissue | Up to 33% in whole  50 Gy or less<br>Up to 66% in whole  35 Gy or less<br>Up to 100% in whole  30 Gy or less |
| d | | Pancreas normal tissue | 50 Gy or less in any tissue |
| e | | Stomach normal tissue | 50 Gy or less in any tissue |
| f | | Intestine normal tissue | 36 Gy or less in any tissue |
| g | | Spinal cord | 25 Gy or less in any tissue |

F I G. 27

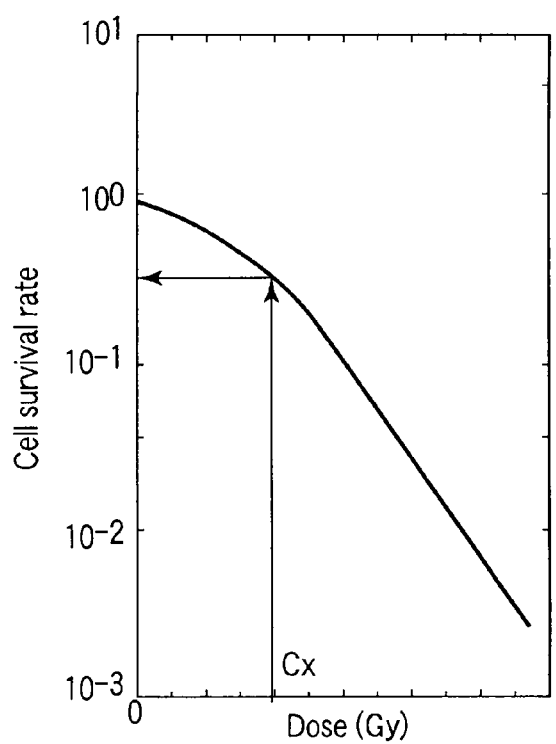

F I G. 28

First day First plan

| Region | Number of voxels | Region name | Permissible dose per time |
|---|---|---|---|
| a | | Liver malignancy (GTV+CTV) | 2 Gy or more each |
| b | | Margin | About 1.7 Gy each |
| c | | Liver normal tissue | Residual tissue rate: 90% or higher |
| d | | Pancreas normal tissue | 1.4 Gy or less in any tissue |
| e | | Stomach normal tissue | 1.4 Gy or less in any tissue |
| f | | Intestine normal tissue | 1.0 Gy or less in any tissue |
| g | | Spinal cord | 0.7 Gy or less in any tissue |

⋮

Third day Third plan

F I G. 29

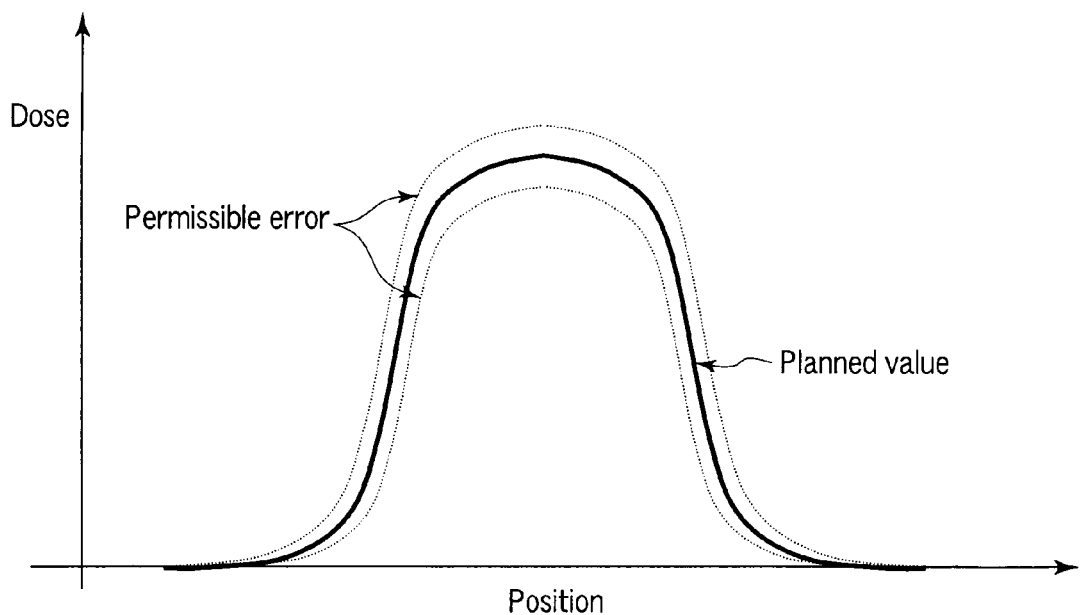

F I G. 30

First day First plan

| Region | Nnumber of voxels | Region name | Permissible dose per time |
|---|---|---|---|
| a | | Liver malignancy (GTV+CTV) | 2 Gy or more each |
| b | | Margin | About 1.7 Gy each |
| c | | Liver normal tissue | Up to 33% in whole   1.4 Gy or less<br>Up to 66% in whole   1.0 Gy or less<br>Up to 100% in whole  0.8 Gy or less |
| d | | Pancreas normal tissue | 1.4 Gy or less in any tissue |
| e | | Stomach normal tissue | 1.4 Gy or less in any tissue |
| f | | Intestine normal tissue | 1.0 Gy or less in any tissue |
| g | | Spinal cord | 0.7 Gy or less in any tissue |

⋮

Third day  Third plan

| Number of times | 1 | 2 | 3 |
|---|---|---|---|
| Time | 10:30:00 | 10:40:25 | 10:50:50 |
| Region | Absorption dose [Gy] | Absorption dose [Gy] | Absorption dose [Gy] |
| a1 | 2.0 | 1.9 | 2.1 |
| b1 | 1.3 | 1.3 | 1.2 |
| b2 | 1.5 | 1.3 | 1.6 |
| b3 | 1.4 | 1.4 | 1.5 |
| . | . | . | . |
| . | . | . | . |
| c1 | 0.6 | 0.6 | 0.7 |
| c2 | 0.8 | 0.7 | 0.8 |
| . | . | . | . |
| . | . | . | . |
| d1 | 0.1 | 0.1 | 0.1 |
| d2 | 0.1 | 0.1 | 0.1 |
| d3 | 0.4 | 0.5 | 0.4 |
| . | . | . | . |
| . | . | . | . |
| fn | 0.0 | 0.0 | 0.0 |

FIG. 34B

| Integrated value | | | |
|---|---|---|---|
| Number of times | 1 | 2 | 3 |
| Time | 10:30:00 | 10:40:25 | 10:50:50 |
| Region | Absorption dose [Gy] | Absorption dose [Gy] | Absorption dose [Gy] |
| a1 | 2.0 | 3.9 | 6.0 |
| b1 | 1.3 | 2.6 | 3.8 |
| b2 | 1.5 | 2.8 | 4.4 |
| b3 | 1.4 | 2.8 | 4.3 |
| . | . | . | . |
| . | . | . | . |
| c1 | 0.6 | 1.2 | 1.9 |
| c2 | 0.8 | 1.5 | 2.3 |
| . | . | . | . |
| . | . | . | . |
| d1 | 0.1 | 0.2 | 0.3 |
| d2 | 0.1 | 0.2 | 0.3 |
| d3 | 0.4 | 0.9 | 1.3 |
| . | . | . | . |
| . | . | . | . |
| fn | 0.0 | 0.0 | 0.0 |

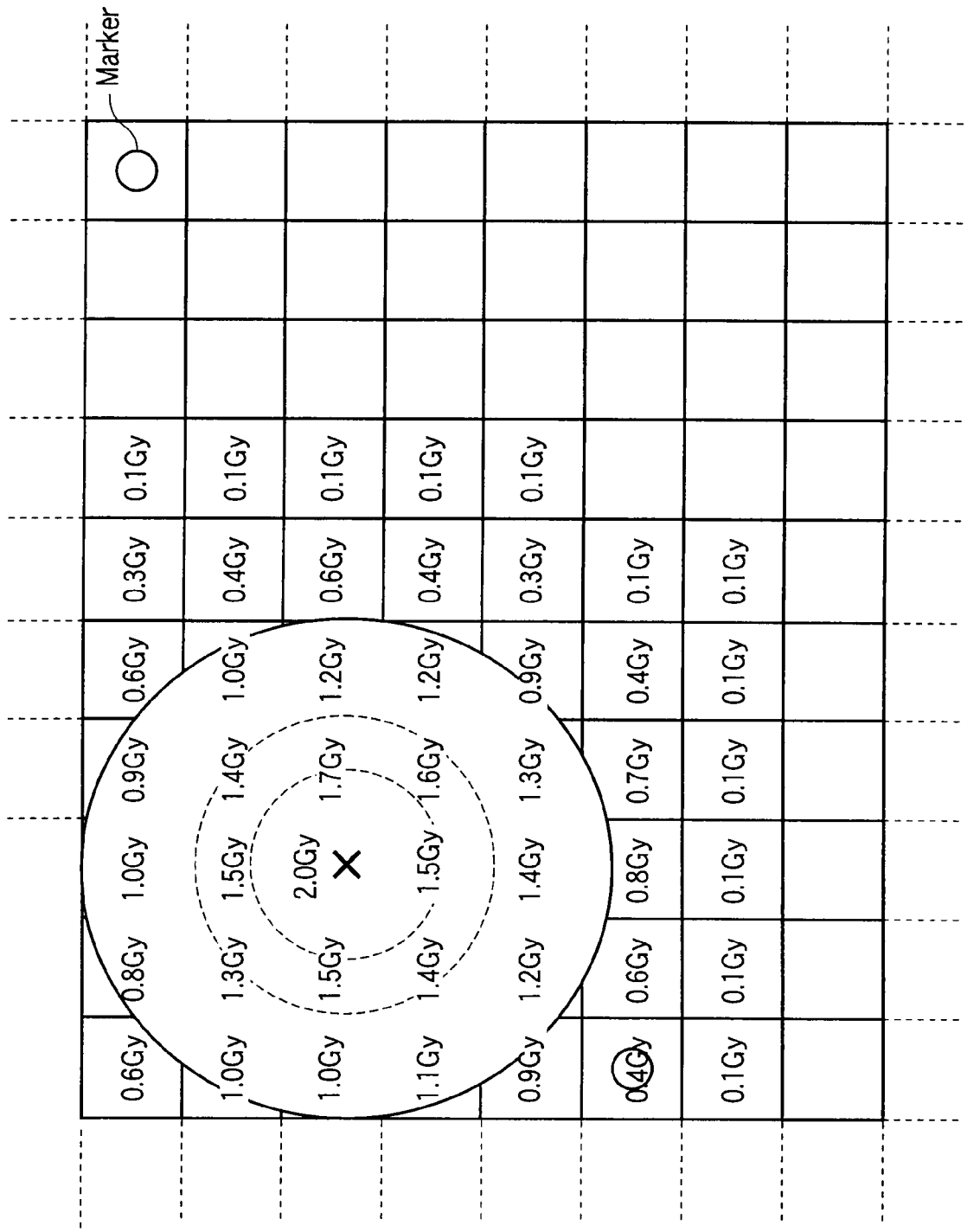
F I G. 35

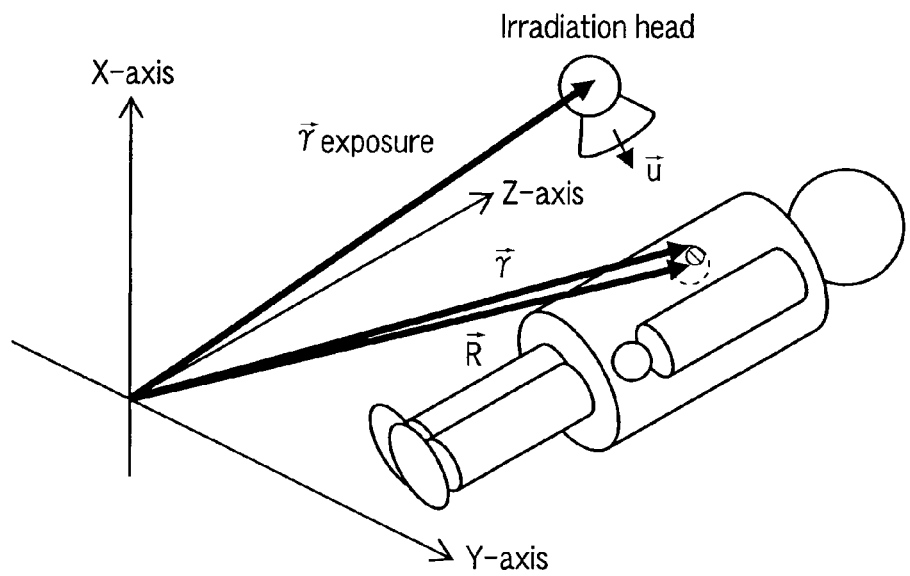
F I G. 42
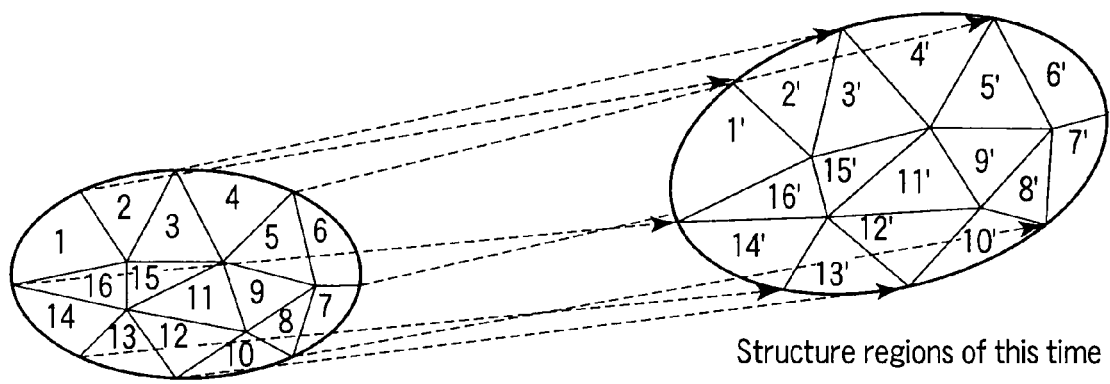
Structure regions of last time          Structure regions of this time
F I G. 43

Irradiation protocol

Patient ID: P005  Name: Taro Toshiba   [Get Study]

Treatment history

| Date | Tumor Absorption dose | Risk organ 1 Absorption dose | Risk organ 2 Absorption dose | ... | Risk organ n Absorption dose |
|---|---|---|---|---|---|
| 2007/10/02 | 5Gy | 0.05Gy | 0.05Gy | ... | 0.05Gy |
| 2007/10/03 | 5Gy | 0.01Gy | 0.01Gy | ... | 0.01Gy |
| 2007/10/04 | 5Gy | 0.01Gy | 0.01Gy | ... | 0.01Gy |
| 2007/10/05 | 5Gy | 0.03Gy | 0.03Gy | ... | 0.03Gy |
| 2007/10/06 | 5Gy | 0.07Gy | 0.07Gy | ... | 0.07Gy |
| 2007/10/07 | 5Gy | 0.10Gy | 0.10Gy | ... | 0.10Gy |
| Accumulated dose | 30Gy | 0.27Gy | 0.27Gy | ... | 0.27Gy |

Risk organ permissible limit setting

○ Automatic   ● Manual

| | Risk organ 1 | Risk organ 2 | ... | Risk organ n |
|---|---|---|---|---|
| Permissible accumulated dose | 30Gy | 40Gy | | 10Gy |
| Function residual ratio (present value) | 98% | 98% | | 73% |
| Permissible function residual ratio setting | 65% (0%–100%) | 65% (0%–100%) | | 85% (0%–100%) |

Setting of division number and dose of crossfiring

Irradiation division number of times: 5 times    Total irradiation dose: 5 Gy

[Start Simulation]

Crossfiring irradiation plan

[update]

| Number of irradiations | Head position | Head direction | Output | Absorption dose (record) |
|---|---|---|---|---|
| 1st | $\vec{r} = (x_e\ y_e\ z_e)$ | $\vec{u} = (x_u\ y_u\ z_u)$ | A | 1Gy |
| 2nd | | | | |
| 3rd | | | | |
| 4th | | | | |
| 5th | | | | |

[Send Protocol]

FIG. 45

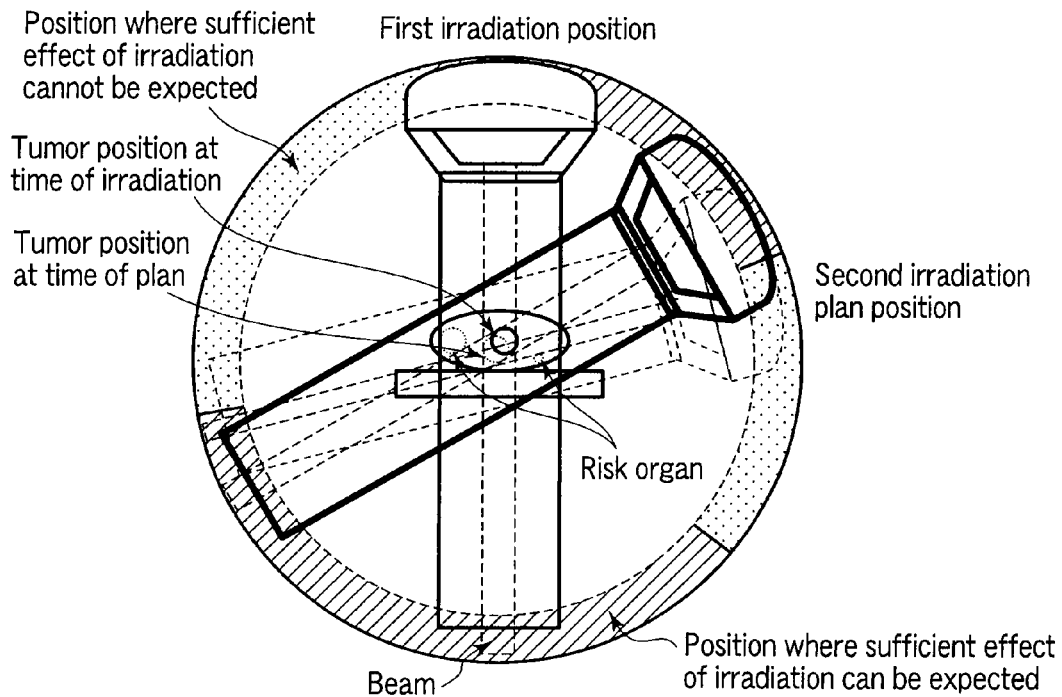
F I G. 47
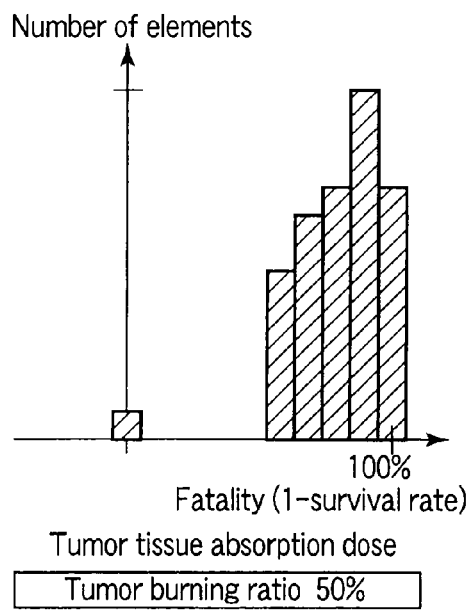
F I G. 48A
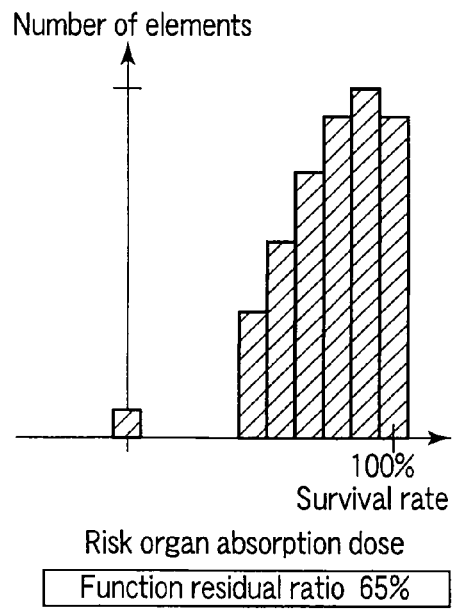
F I G. 48B

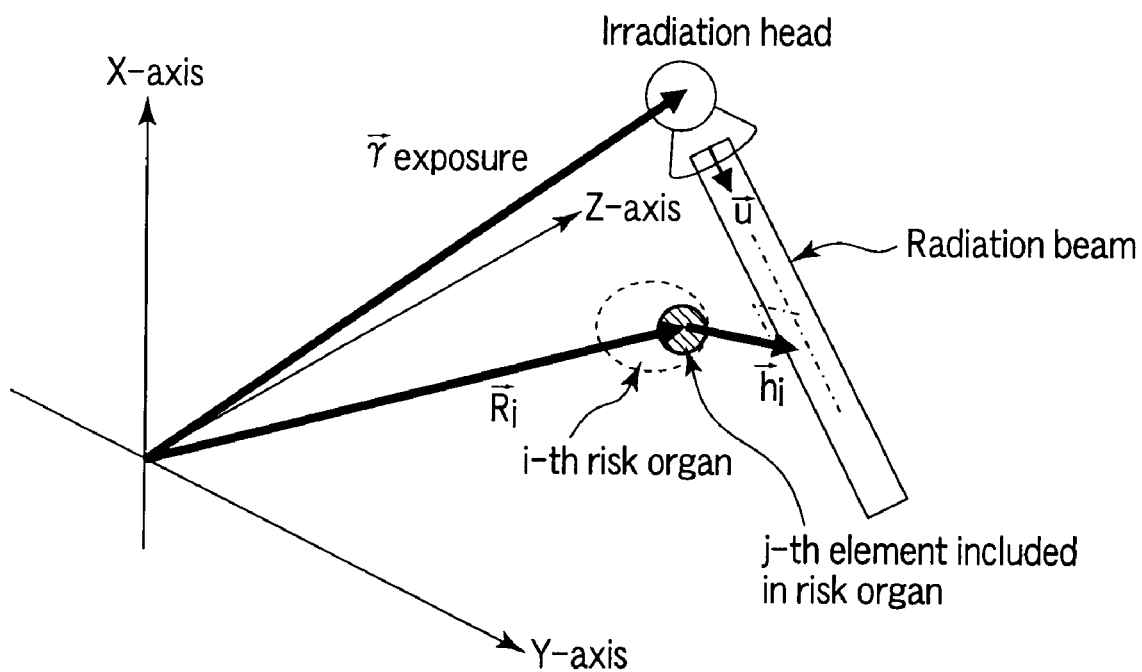
F I G. 51

RADIOTHERAPY SUPPORT APPARATUS

CROSS-REFERENCE TO RELATED APPLICATIONS

This application is based upon and claims the benefit of priority from prior Japanese Patent Applications No. 2008-002370, filed Jan. 9, 2008; No. 2008-002371, filed Jan. 9, 2008; and No. 2008-002372, filed Jan. 9, 2008, the entire contents of all of which are incorporated herein by reference.

BACKGROUND OF THE INVENTION

1. Field of the Invention

The present invention relates to an apparatus for supporting an operator at the time of radiotherapy treatment.

2. Description of the Related Art

In radiotherapy treatment typified by external X-ray radiotherapy treatment, before the treatment, an irradiation plan (the direction and the dose of radiation to an affected region) is made on a patient image. On the basis of the irradiation plan, irradiation of the patient is performed. However, at present, there is no means for confirming whether irradiation is actually performed to the patient with the planned position and dose or not. Even if insufficient irradiation of an affected region or excessive irradiation of a normal tissue occurs, it is not noticed. In some cases, using a phantom and an X-ray detector prior to irradiation, whether planned irradiation can be performed or not is confirmed. However, it is difficult to place a patient in a position according to the irradiation plan, on a bed different from a phantom which is easily portable and whose position can be freely adjusted. The confirmation prior to radiation does not completely assure the planned irradiation of the patient.

A technique disclosed in Jpn. Pat. Appln. KOKAI Publication No. 05-156526 is to detect scattered X-rays in an X-rayed subject and to obtain a cross-sectional image of the subject. The characteristic of the technique is that a scan is performed with a pencil beam and a three-dimensional scattering radiation image of the subject is reconstructed. That is, the technique assumes only the pencil beam but is not directed to obtain a scattering radiation image of a region through which a beam having a limited width passes (a spatial distribution of dose of a therapeutic beam), which is used in X-ray therapy. Since forward scattering is dominant in the scattering in a subject of a therapeutic beam (a few MeV) having high energy, when a detector is disposed in the incident X-ray direction, it is difficult to distinguish scattering radiation and penetrated radiation from each other. A correction process is therefore necessary for detection of scattering radiation.

Amid mounting social concern over medical errors, also in radiotherapy treatment, excessive irradiation of a patient has been reported and has become an issue. It is predicted that recording of the "fact" of medical acts performed such as a region in a patient and an irradiation dose is becoming more and more important. In the field of external X-ray radiotherapy treatment, attempts to irradiate an affected region more precisely are being made such as a method of irradiation so as to synchronize and trace motion of a tumor in a patient caused by breathing or the like, a method of collimating a therapeutic X-ray beam in accordance with the shape of a tumor and irradiating the tumor with the beam, and the like. The object of the precise irradiation is to concentrate the dose to an affected region. Therefore, if the therapeutic X-ray beam is off from the irradiation target, normal tissue is considerably damaged. As the irradiation is becoming more precise, it is becoming more important to check whether the irradiation is performed as planned.

BRIEF SUMMARY OF THE INVENTION

In view of the circumstances, an object of the present invention is to provide an apparatus for supporting radiotherapy treatment to enable treatment to be performed accurately and safely by providing the operator with information for preventing insufficient irradiation of a region to be treated and excessive irradiation of a normal tissue in radiotherapy treatment.

According to an aspect of the present invention, there is provided a radiotherapy support apparatus comprising: a storage unit which stores absorption dose volume data expressing a spatial distribution of absorption dose in a subject; a generation unit which generates fusion data associated with morphology volume data of the subject and the absorption dose volume data so as to be associated with a plurality of segments; and a display unit which displays an image which has the distribution of absorption dose superimposed on the two-dimensional morphology image of the subject using the fusion data.

According to an aspect of the present invention, there is provided a radiotherapy support apparatus comprising: a storage unit which stores absorption dose volume data expressing a spatial distribution of absorption dose in a subject; a comparison unit which compares between the absorption dose volume data and predetermined reference dose data for the subject so as to be associated with a plurality of segments; and an evaluation unit which evaluates a result of the comparison of the absorption dose and the reference dose, and outputs a warning or stops operation of a treatment apparatus in accordance with the evaluation result.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

FIG. 1 is a diagram for explaining the principle and method of measuring scattering radiation from a subject based on therapeutic radiation of a radiotherapeutic system;

FIG. 5 is a flowchart showing the flow of processes at the time of radiotherapy treatment including the operation of the radiotherapeutic system;

FIG. 7 is a flowchart showing the flow of processes at the time of radiotherapy treatment including the operation of the radiotherapeutic system;

FIG. 13A is a display example of an absorption dose image for radiation sensitivity threshold indication;

FIG. 13B is a display example of an absorption dose image for radiation sensitivity threshold indication;

FIG. 13C is a display example of an absorption dose image for radiation sensitivity threshold indication;

FIG. 16A is a diagram showing an example of a display image generated by a plan evaluation module;

FIG. 16B is a diagram showing another example of a display image generated by the plan evaluation module;

FIG. 16C is a diagram showing another example of a display image generated by the plan evaluation module;

FIG. 20 is a flowchart showing the procedure of a positioning process;

FIG. 22 is a diagram showing an example expressing the present state and a simulation result in a table form;

FIG. 23 is a flowchart showing the procedure of warning when irradiation exceeds an irradiation permissible value;

FIG. 27 is a diagram showing an example of the configuration of a permissible dose table;

FIG. 28 is a diagram showing an example of cell survival curve with respect to radiation;

FIG. 29 is a diagram showing an example of a therapeutic plan in a table form;

FIG. 30 is a diagram in which a permissible error is reflected in a plan value;

FIG. 31 is a diagram showing an example of a therapeutic plan in a table form;

FIG. 34A is a diagram showing an actual measurement irradiation position and an actual measurement absorption dose stored in a storage unit 7;

FIG. 34B is a diagram showing an actual measurement irradiation position and an actual measurement absorption dose stored in the storage unit 7;

FIG. 35 is a diagram showing the actual measurement irradiation position and the actual measurement absorption dose in a distribution map;

FIG. 42 is a diagram for explaining definition of a variable;

FIG. 43 is a diagram for explaining segmentation;

FIG. 45 is a diagram showing an example of a screen image displayed in a display unit;

FIG. 47 is a diagram showing an irradiation position presentation method;

FIG. 48A is a diagram showing the relation between absorption doses in a tumor and a risk organ and the number of elements;

FIG. 48B is a diagram showing the relation between absorption doses in a tumor and a risk organ and the number of elements;

FIG. 51 is a diagram showing arrangement of a risk organ and a radiation beam.

DETAILED DESCRIPTION OF THE INVENTION

Figure 2:
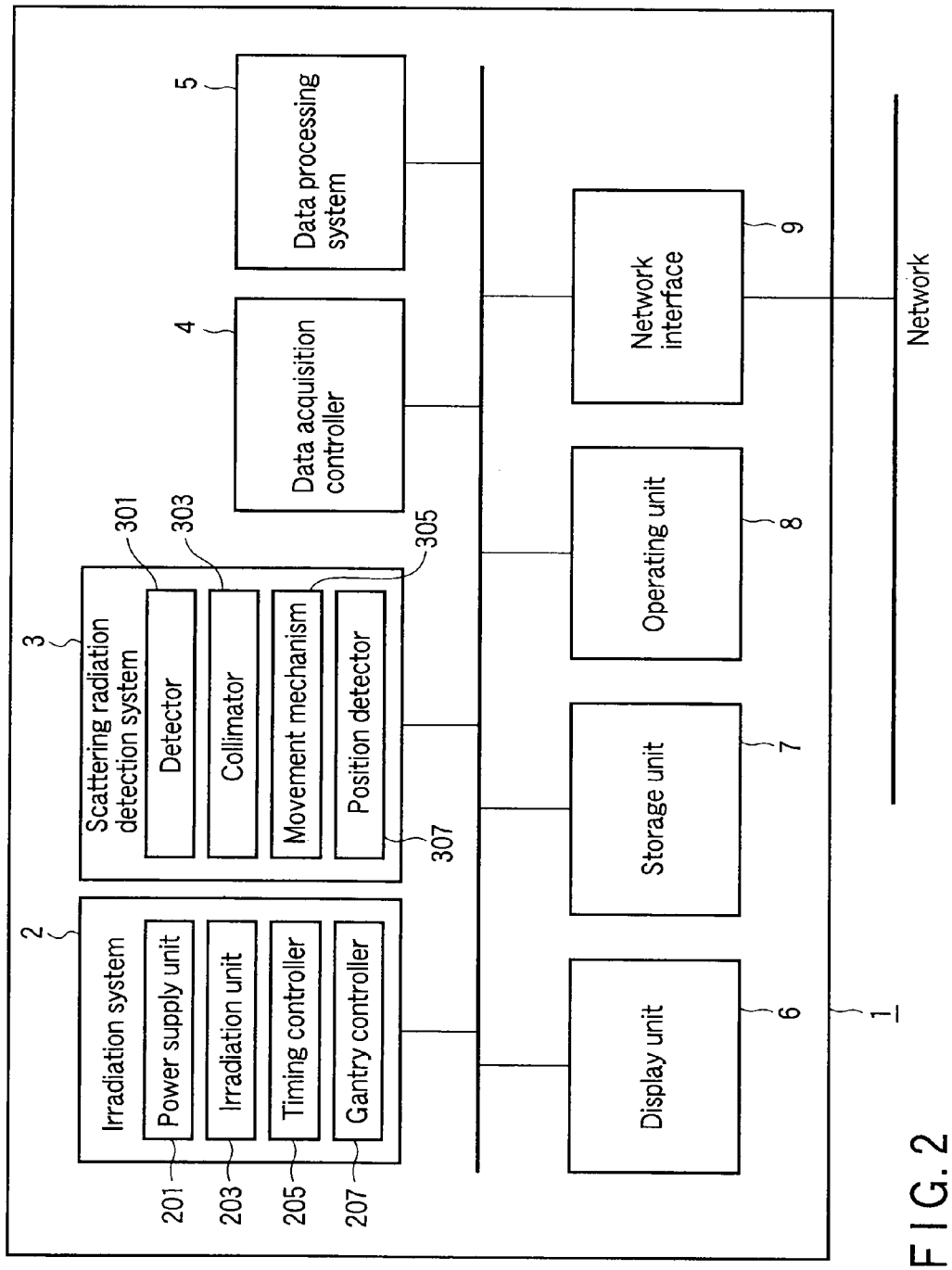
FIG. 2 is a block configuration diagram of the radiotherapeutic system according to an embodiment of the present invention.

Embodiments of the present invention will be described below with reference to the drawings. In the following description, the same reference numbers are designated to components having almost the same functions and configurations and repetitive description will be given only when required.

[Principle and Method]

A radiotherapeutic system of this embodiment measures scattering radiation from a subject on the basis of radiation emitted to the subject and, on the basis of the scattering radiation, obtains information objectively showing an irradiated region in the subject and dose of the radiation. The principle and the method are as follows.

FIG. 1 is a diagram for explaining the principle and method of measuring scattering radiation from a subject on the basis of therapeutic radiation of the radiotherapeutic system of the invention.

The effect of treatment with external X-ray radiation is produced mainly by X-rays scattered in the body of a patient. Specifically, when a therapeutic X-ray beam is scattered by electrons in the body of a patient, the electrons which receive the energy fly in tissues and then stop. Until the electrons stop, the electrons generate radicals from molecules in the tissues, and damage DNA in the cells. The cells which are damaged and could not recover finally die. This is the effect of the treatment with the X-ray irradiation. The more recoil electrons are generated, the higher the probability that cells composing a tissue die becomes. Consequently, the treatment effect is proportional to the number of occurrences of scattering reaction.

From the above, when the number of times of scattering that occurs in a tissue is known, the treatment effect (how the tissue is damaged) can be known. The number of occurrences of scattering can be known by measuring the number of scattering rays. The travel directions of most X-rays scattered are changed by the electrons and the resultant rays exit from the patient body, so that they can be measured by an X-ray detector mounted outside of the patient body.

In the radiotherapeutic system according to a first example of the embodiment of the present invention, a detector having a collimator is mounted in a position at a specific angle with respect to a therapeutic X-ray beam and selectively detects only scattering radiation in the direction. Since the angle and the degree of X-rays scattered by Compton scattering are known theoretically, if scattering radiation at a certain angle can be detected, the magnitude of scattering radiation at other angles can be also estimated. Further, to three-dimensionally obtain a distribution of places where scattering occurs in the patient body, the detector is rotated during irradiation and scattering radiation is measured from all of directions (refer to, for example, FIG. 5). After that, a reconstruction process is performed, and a distribution of occurrence of scattering radiation in the subject is three-dimensionally imaged.

In the radiotherapeutic system according to a second example of the embodiment of the present invention, a detector having a collimator is mounted in a position at a predetermined angle (scattering angle) with respect to a therapeutic X-ray beam and selectively detects only scattering radiation in the direction. By executing the detection while maintaining the angle formed between the axis of a therapeutic X-ray beam emitted from an irradiation unit and a detection face of the detector and moving a therapeutic X-ray beam and the detection face, a three-dimensional region in the subject is scanned. Using three-dimensional scattering radiation data related to the predetermined scattering angle, the scattering radiation volume data is reconstructed, and the scattering radiation volume data is converted to absorption dose volume data indicative of a three-dimensional distribution of absorbed radiation dose, thereby generating an absorption dose image.

[Configuration]

FIG. 2 is a block configuration diagram of a radiotherapeutic system 1 of the embodiment. As shown in FIG. 2, the radiotherapeutic system 1 has an irradiation system 2, a scattering radiation detection system 3, a data acquisition controller 4, a data processing system 5, a display unit 6, a storage unit 7, an operating unit 8, and a network interface 9. The irradiation system 2 and the scattering radiation detection system 3 are installed in a gantry. By moving and rotating the gantry, the irradiation system 2 and the scattering radiation detection system 3 can be disposed in arbitrary positions with respect to the subject. The data acquisition controller 4, the data processing system 5, the display unit 6, the storage unit 7, the operating unit 8, and the network interface 9 are installed, for example, in the body (casing) of the radiotherapeutic system 1.

[Irradiation System]

The irradiation system 2 has a power supply unit 201, an irradiation unit 203, a timing controller 205, and a gantry controller 207.

The power supply unit 201 supplies power to the irradiation unit 203 under control of the data acquisition controller 4.

The irradiation unit 203 is an irradiation apparatus having the configuration of, for example, a linear accelerator (linac) or the like. In the irradiation unit 203, thermal electrons emitted from a cathode are accelerated to a few hundreds keV by an electron gun provided at one end of an accelerating tube. Next, microwaves generated from a klystron are guided to the accelerating tube by using a waveguide. In the accelerating tube, the thermal electrons are accelerated to energy of a few MeV. The direction of the accelerated thermal electrons is changed by a magnet, and the thermal electrons collide with a transmission target. By breaking radiation, X-rays of energy of a few MeV are generated. The irradiation unit 203 shapes the X-rays to a predetermined shape (for example, a conical shape or thin flat shape) by a collimator, and emits the resultant rays to a three-dimensional region in the subject laid on the bed.

The timing controller 205 controls the power supply unit 201 so that power is supplied to the irradiation unit 203 at a predetermined timing under control of the data acquisition controller 4.

The gantry controller 207 controls, for example, the movement position and the rotation position of the gantry in accordance with the control instruction from the operating unit 8 and the data acquisition controller 4.

[Scattering Radiation Detection System]

The scattering radiation detection system 3 has a detector 301, a collimator 303, a movement mechanism 305, and a position detector 307.

The detector 301 is a semiconductor detector capable of detecting X-rays of a few hundred keV, an imaging plate, or the like, and detects scattering radiation from a subject based on radiation emitted to the subject. The preferred size of the detector, the disposition angle with respect to the radiation beam axis, the number of pixels, and the like will be described later.

The collimator 303 is a narrowing device for selectively detecting only scattering radiation in a specified direction.

The movement mechanism 305 is a movement mechanism for moving the position and the angle of the detector 301 to control the angle of the detection face of the detector 301 to the irradiation beam axis of the irradiation unit 203 (that is, the angle between the irradiation beam axis and the normal line to the detection face of the detector 301), the rotation angle of the detector 301 using the radiation beam axis as a center, the distance between the subject and the detection face of the detector 301, and the like.

The position detector 307 is an encoder for detecting the position of the detector 301.

[Data Acquisition Controller]

The data acquisition controller 4 performs total control on the scattering radiation measurement at the time of radiotherapy treatment. For example, the data acquisition controller 4 statically or dynamically controls the radiotherapeutic system 1 in terms of irradiation, scattering radiation measurement, data process, image display, network communication and the like by obtaining a signal from the timing controller 205 of the irradiation system 2 and transmitting a scattering radiation measurement start trigger and a detection data transmission trigger to the scattering radiation detection system 3. As necessary, the data acquisition controller 4 optimizes scan time in accordance with irradiation time of each radiation on the basis of a therapeutic plan received from a radiotherapy planning apparatus via a network.

[Data Processing System]

Figure 3:
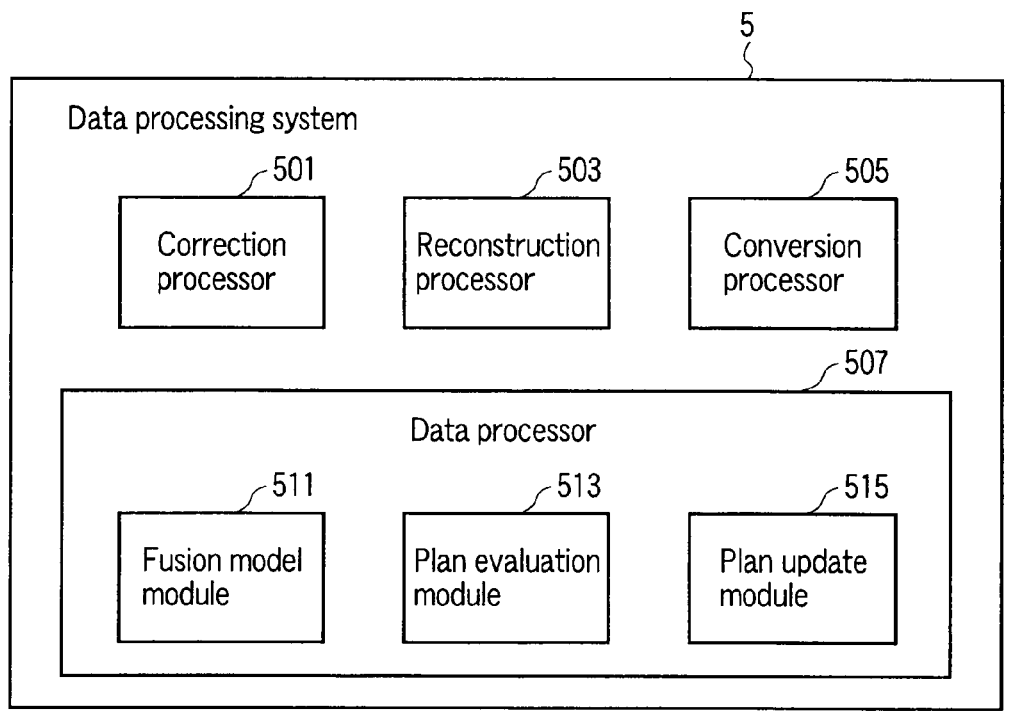
FIG. 3 is a functional block diagram showing the configuration of a data processing system.

FIG. 3 is a functional block diagram showing the configuration of the data processing system 5.

The data processing system 5 has a correction processor 501, a reconstruction processor 503, a conversion processor 505, and a data processor 507.

The correction processor 501 performs a data calibration process, a correction process for eliminating noise, and the like as necessary. The correction process executed by the correction processor 501 will be described in detail later.

The reconstruction processor 503 executes an image reconstruction process using scattering radiation image data detected by the scattering radiation detection system 3 and position information indicative of a position in which the scattering radiation image data is detected to obtain scattering radiation volume data indicative of a three-dimensional distribution of density of the number of scattering events (the number of scattering occurrences). As the reconstruction method, for example, when the direction of the collimator is perpendicular to the scan axis, a CT reconstruction method is used. On the other hand, when the direction of the collimator is not perpendicular to the scan axis, a tomographic reconstruction method is used.

The conversion processor 505 converts three-dimensional image data obtained by the image reconstruction process to absorption dose volume data indicative of a three-dimensional distribution of absorbed radiation dose (absorption dose).

The data processor 507 has a fusion model module 511, a plan evaluation module 513, and a plan update module 515.

The fusion model module 511 generates a three-dimensional model on the basis of morphology image data obtained by an X-ray image pickup apparatus, a CT, or other modality, and generates fusion model data obtained by fusing an absorption dose image to the three-dimensional model using the absorption dose volume data.

The plan evaluation module 513 compares and displays an irradiation plan and an irradiation record and performs simulation for predicting the influence of irradiation of the next time on.

The plan update module 515 determines whether the irradiation plan is proper or not on the basis of the absorption dose data using a predetermined evaluation reference, and provides an optimum therapeutic plan. The details of the modules will be described later.

[Display Unit, Storage Unit, Operating Unit, and Network Interface]

The display unit 6 is constructed by a display such as an LCD. On the basis of data output from various module of the data processor 507, for example, the display unit 6 fuses the absorption dose image with a plan image and images obtained just before irradiation and during the irradiation, and displays the resultant images.

Figure 4:
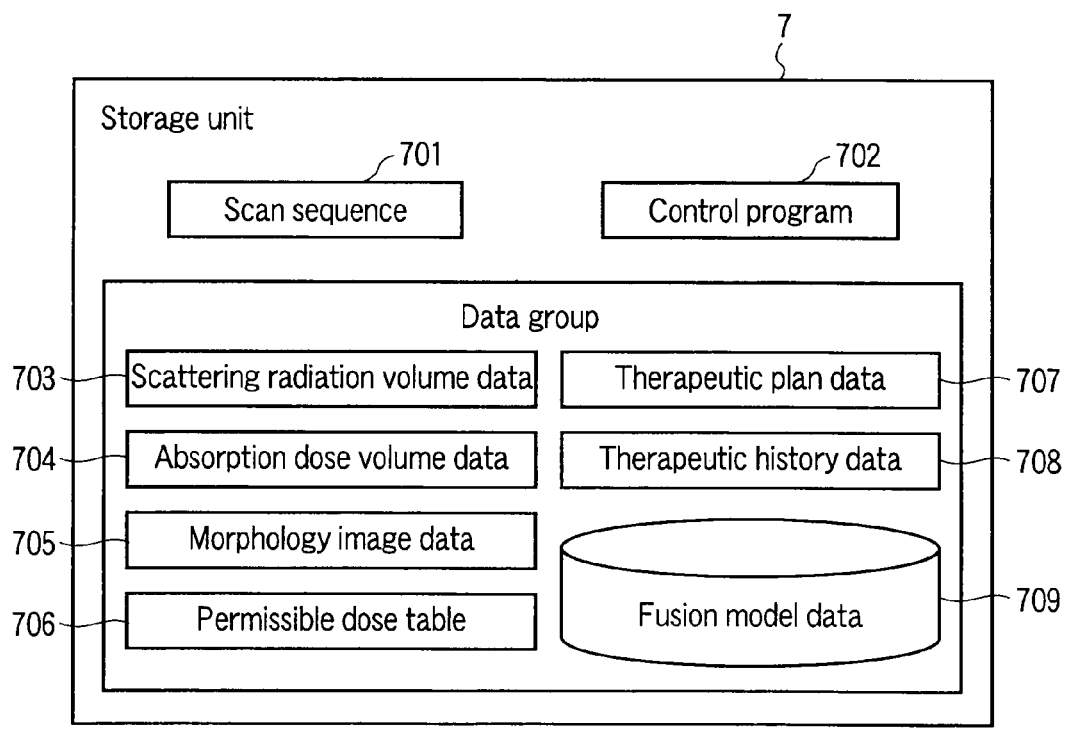
FIG. 4 is a diagram showing the configuration of data stored in a storage unit.

As shown in FIG. 4, the storage unit 7 stores: a predetermined scan sequence 701 for obtaining (scanning) scattering radiation data while rotating the detector 301 around the axis of a radiation beam emitted as a center; a control program 702 for executing the correction process, the image reconstruction process, the conversion process, the display process, and the like, and displaying and editing a therapeutic plan on the system; scattering radiation volume data 703 obtained by the radiotherapeutic system 1; absorption dose volume data 704; morphology image data 705 obtained by other modalities such as an X-ray computerized tomography apparatus; and the like. The data stored in the storage unit 7 can be also transferred to an external apparatus via a network interface 90.

In the storage unit 7, a permissible dose table 706, therapeutic plan data 707, and therapeutic history data 708 captured from an external therapeutic planning apparatus or the like via the network interface 90 are stored. Further, the storage unit 7 stores fusion model data 709 generated by the fusion model module 511.

The operating unit 8 has various switches, buttons, a track ball 13s, a mouse 13c, a keyboard 13d, and the like for taking various instructions, conditions, region-of-interest (ROI) setting instructions, various image quality parameter setting instructions, and the like from the operator to an apparatus body 11.

The network interface 9 transfers the absorption dose image data or the like obtained by the radiotherapeutic system 1 to another apparatus via a network and obtains, for example, a therapeutic plan or the like generated by a radiotherapy planning apparatus via a network.

(Method of Generating Absorption Dose Image Data)

FIRST EXAMPLE

Next, a method of generating absorption dose image data using the radiotherapeutic system 1 of the first example will be described. In the radiotherapeutic system according to the first example, a detector having a collimator is mounted in a position at a specific angle with respect to a therapeutic X-ray beam and selectively detects only scattering radiation in the direction. Further, to three-dimensionally obtain a distribution of places where scattering occurs in the patient body, the detector is rotated during irradiation and scattering radiation is measured from all of directions (refer to, for example, FIG. 6). After that, a reconstruction process is performed, and a distribution of occurrence of scattering radiation in the subject is three-dimensionally imaged.

FIG. 5 is a flowchart showing the flow of processes in radiotherapy treatment including a process of generating absorption dose image data according to the example. The processes in the steps will be described below.

[Disposition of Subject and the like in Step S1a]

First, the data acquisition controller 4 acquires therapeutic plan information on the subject via, for example, a network and displays it on the display unit 6. The operator disposes the subject on the bed in accordance with the displayed therapeutic plan and performs setting of irradiation time, selection of a scan sequence such as setting of the number of times of measuring scattering radiation per rotation, measurement angle, and the like via the operating unit 8 (step S1a). The irradiation time and the like may be automatically set on the basis of the obtained therapeutic plan information.

[Irradiation and Acquisition of Scattering Radiation Image Data in Multiple Directions in Step S2a]

Figure 6:
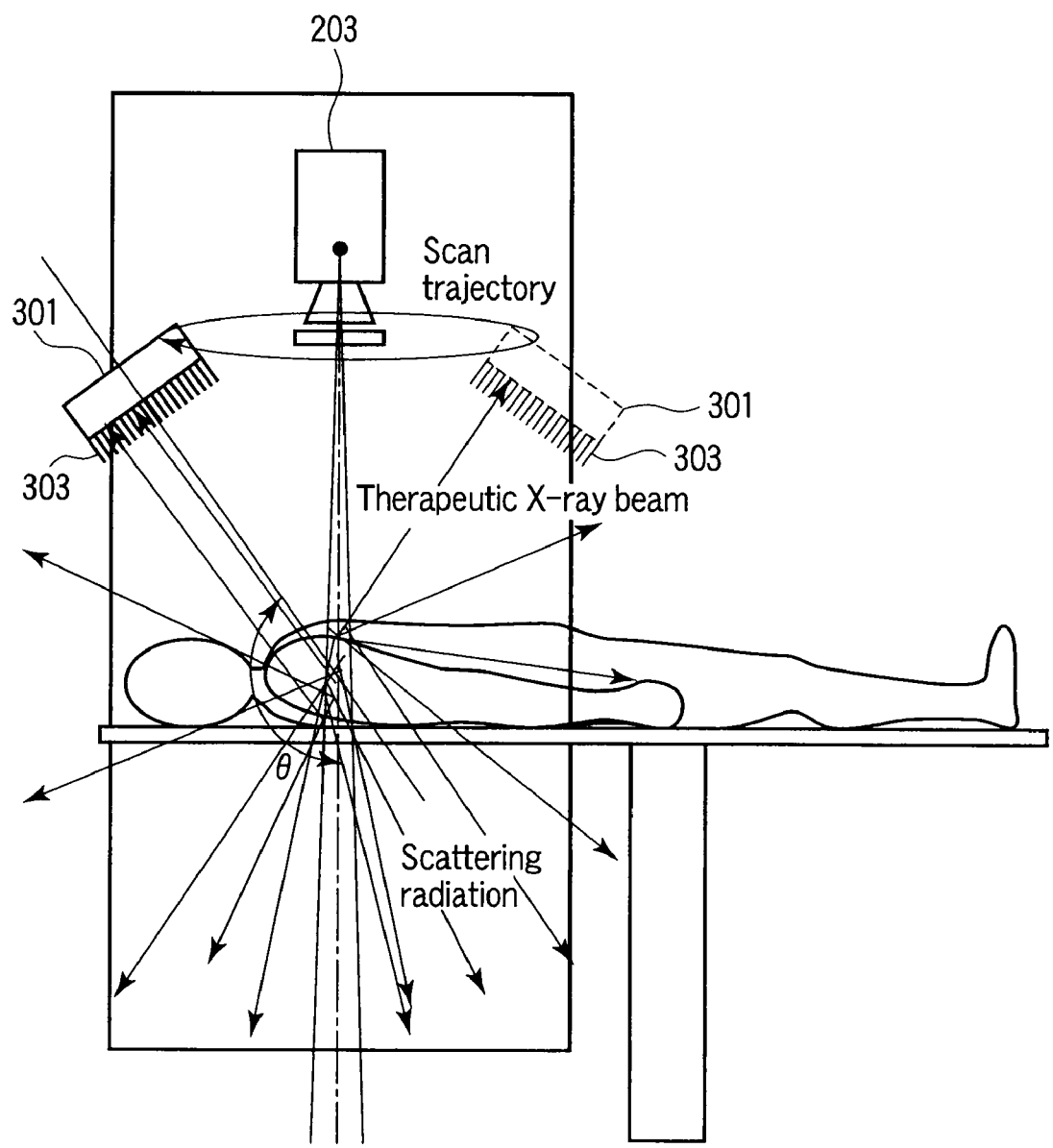
FIG. 6 is a diagram showing a form of measurement of scattering radiation of the radiotherapeutic system.

FIG. 6 is a diagram showing a form of measuring scattering radiation of the radiotherapeutic system 1. As shown in the diagram, the irradiation system 2 generates therapeutic radiation to be applied to a three-dimensional region in the subject at a predetermined timing. The scattering radiation detection system 3 detects scattering radiation to the outside of the subject on the basis of the irradiation radiation at a plurality of rotation angles using the axis of the emitted radiation beam as a center (step S2a). For example, in the case where irradiation can be performed from one direction for three minutes, data in 18 directions is collected for 10 seconds in each of the directions. Preferably, the 18 directions are set at equal angle intervals using the beam axis as a center. The number of counting times of scattering radiation in each of the directions detected by the detector 301 and position information of the detector 301 at the time of detecting the scattering radiation measured by the position detector 307 is transmitted to the data processing system 5.

In the example, it is assumed that the disposition angle of the detector 301 is set so as to detect back scattering radiation whose scattering angle $\theta$ lies in the range of $120° \leq \theta \leq 165°$ (for example, 155°).

In the above example, for example, when irradiation of 2 Gy is performed from three directions, the number of counts per direction is $1.24 \times 10^5 \times 1/3$ which is almost equal to $4 \times 10^4$ [counts/cm$^2$]. When it is assumed that the irradiation is performed for 180 seconds per direction and measured for 10 seconds, $4 \times 10^4 \times 10/180 = 2 \times 10^3$ [counts/cm$^2$]. The count value does not make any problem for the S/N ratio.

The scattering radiation has to be detected in at least two directions. In reality, it is preferable to detect the scattering radiation in directions as many as possible. The detection positions are preferably arranged at equal angle intervals around the axis of the irradiation beam as a center.

[Pre-process (Correction Process and the like) in Step S3a]

In the collected data, only X-rays scattered in detector disposition angle directions are counted. In reality, however, scattering of X-rays occurs in all directions. The correction processor 501 in the data processing system 5 corrects the count value of the detector and obtains the number of scattering times in all of the direction in accordance with a predetermined calculation equation (step S3a).

[Image Reconstruction Process in Step S4a]

Next, the reconstruction processor 503 in the data processing system 5 executes an image reconstruction process using the projection data in multiple directions to obtain scattering radiation volume data (step S4a). At this time, the axis of rotation of the detector 301 and the direction of the collimator are perpendicular to each other. In the case of capturing an image in an angle range of 180 degrees (+α) or larger, it is sufficient to use the CT reconstruction method. In the other case, the tomographic reconstruction method is used. As the tomographic method, for example, the filtered back-projection method of applying a filter process on a projection image and, after that, performing a back-projection process is used. As the filter construction method, a classical Shepp-Logan filter or a filter disclosed in Japanese Patent Application Nos. 2006-284325 and 2007-269447 is used. In particular, when the methods described in Japanese Patent Application Nos. 2006-284325 and 2007-269447 are used, a scattering source distribution image having clear physical meaning can be generated.

An image obtained by performing the filtering process on the detector image and performing back-projection on the resultant image shows scattering radiation occurrence density per unit volume (the number of scattering times per unit volume). Through all of the steps in the reconstruction process (various correction processes, filter process, and back-projection process), a three-dimensional distribution of scattering radiation occurrence density (scattering radiation volume data) near the place where the therapeutic radiation passes through the subject can be obtained.

[Conversion Process in Step S5a]

The conversion processor 505 in the data processing system 5 converts the scattering radiation volume data to absorption dose volume data indicative of the three-dimensional distribution of the absorbed radiation dose (absorption dose) by converting the number "n" of scattering times per unit volume calculated voxel by voxel to absorption dose (step S5a).

[Generation of Absorbed Dose Image Data and Display of Image Data in Steps S6a and S7a]

Next, the data processor 507 generates absorption dose image data indicative of the distribution of radiation dose absorbed (absorption dose) in a predetermined region in a subject CT image and, for example, combines it with a CT image (step S6a). The display unit 6 displays an absorption dose image in a predetermined form (step S7a).

SECOND EXAMPLE

Next, a method of generating absorption dose image data using the radiotherapeutic system 1 of a second example will be described. In the radiotherapeutic system as the second example, a detector having a collimator is mounted in a position at a specific (scattering angle) angle with respect to a therapeutic X-ray beam and selectively detects only scattering radiation in the direction. By executing the detection while moving the therapeutic X-ray beam and the detection face and maintaining the angle formed between the axis of the therapeutic X-ray beam emitted from the irradiation unit and the detection face of the detector, a three-dimensional region in the subject is scanned. Scattering radiation volume data is reconstructed by using obtained three-dimensional scattering radiation data at the predetermined scattering angle, the scattering radiation volume data is converted to absorption dose volume data indicative of a three-dimensional distribution of the absorbed radiation dose, and an absorption dose image is generated.

FIG. 7 is a flowchart showing the flow of processes in radiotherapy treatment including a process of generating absorption dose image data according to the example. The processes in the steps will be described below.

[Disposition of Subject and the like in Step S1b]

First, in a manner similar to the first example, disposition of a subject and the like is executed (step S1b).

[Irradiation (and Acquisition of Scattering Radiation Data) in Step S2]

Figure 8:
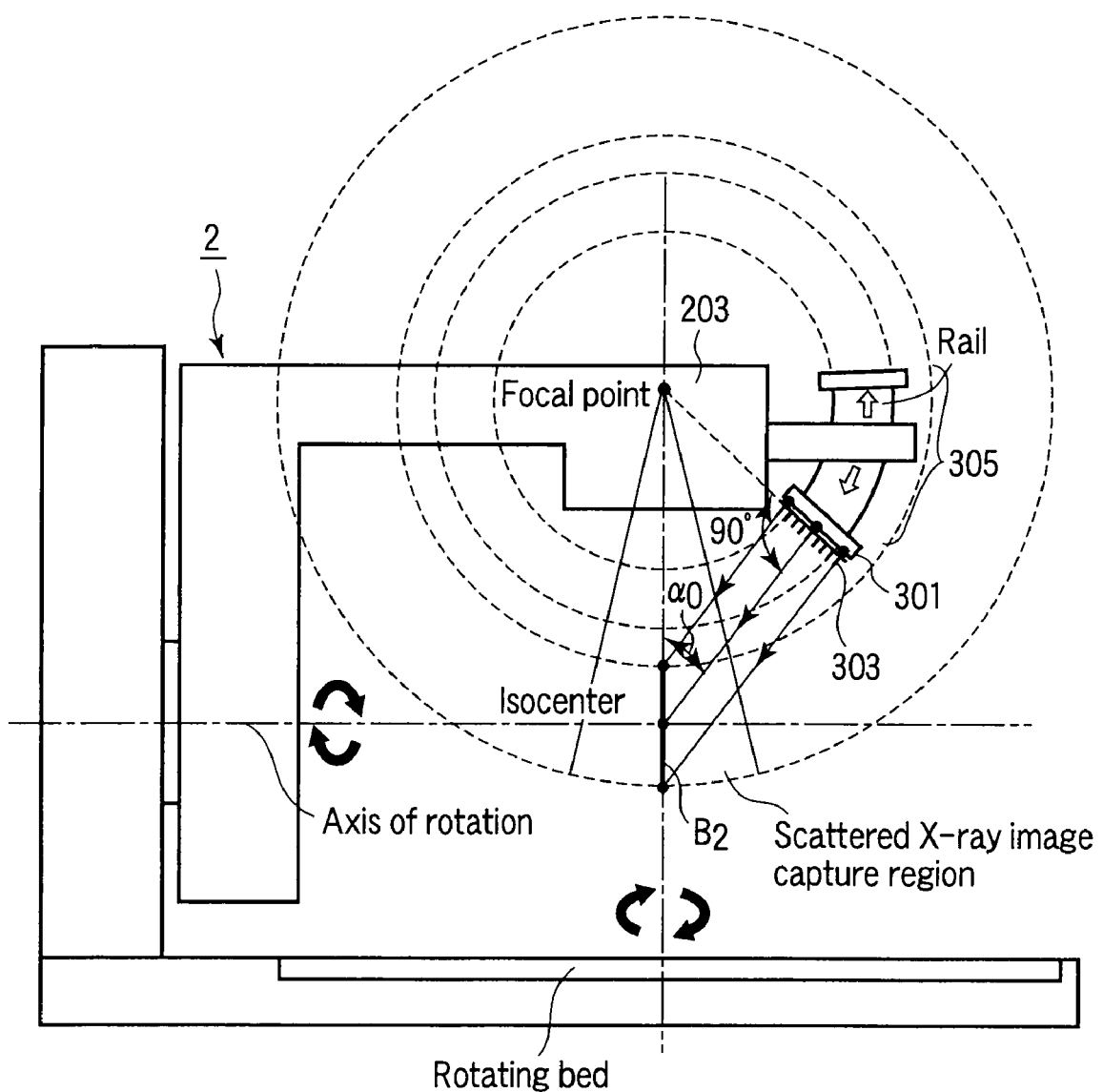
FIG. 8 is a diagram showing a form of measurement of scattering radiation of the radiotherapeutic system.

FIG. 8 is a diagram showing an example of a form of measuring scattering radiation of the radiotherapeutic system 1. As shown in the diagram, the irradiation system 2 emits an X-ray beam B2 shaped in a thin flat state to a subject at a predetermined timing. The scattering radiation detection system 3 detects scattering radiation at a predetermined scattering angle to the outside of the subject on the basis of the irradiation radiation. The data acquisition controller 4 moves an excitation cross section by an X-ray beam B2 wile maintaining the angle formed between the axis of the X-ray beam B2 for treatment emitted from the irradiation unit 203 and the visual line direction of the detector 301, and controls the gantry controller 207 or the movement mechanism 305 so as to scan the three-dimensional region in the subject (step S2).

By the scanning of the three-dimensional region with the X-ray beam B2 for treatment, three-dimensional scattering radiation data made of a plurality of items of two-dimensional scattering radiation data corresponding to the plane of the X-ray beam B2 is obtained.

Figure 9:
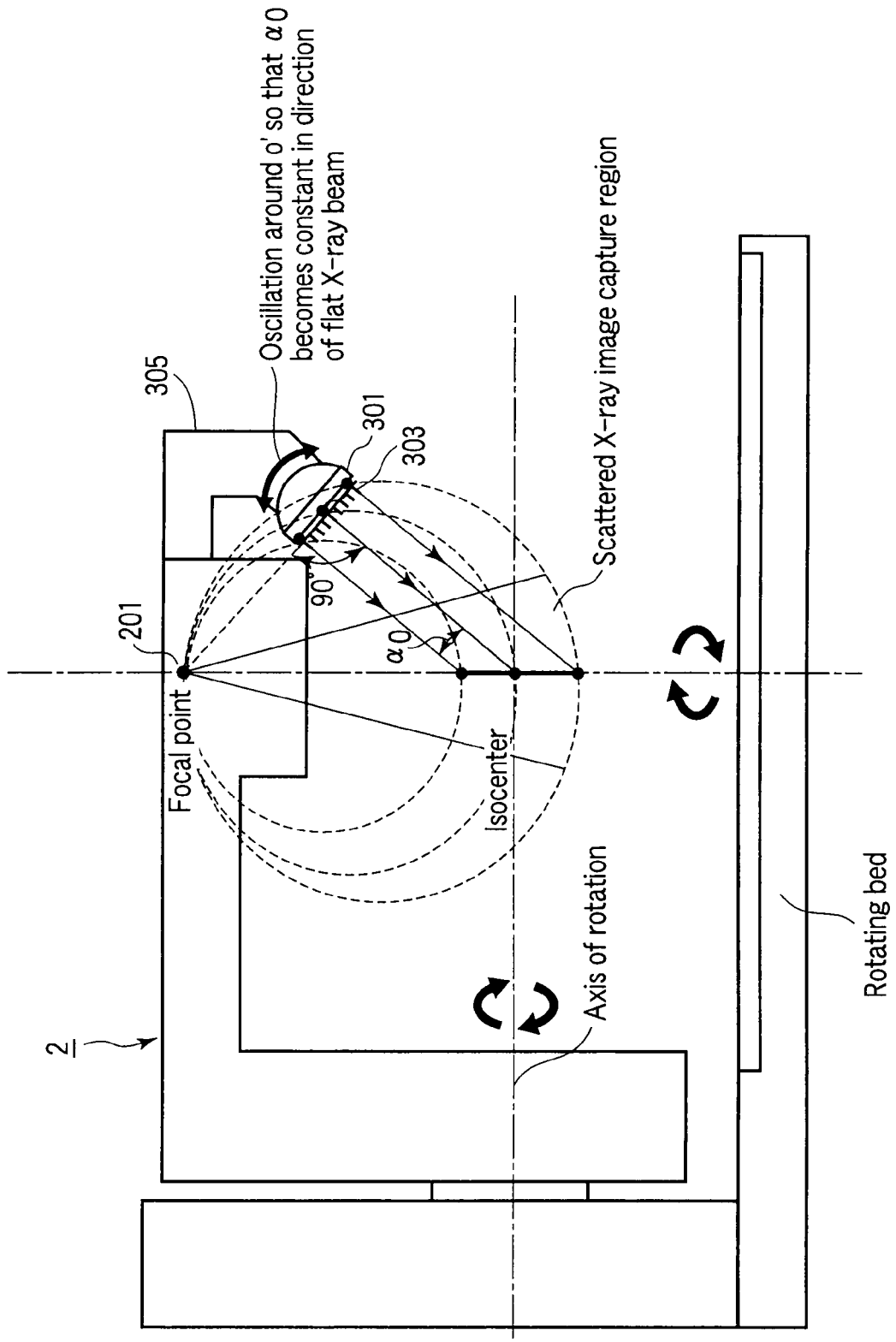
FIG. 9 is a diagram showing another form of the measurement of scattering radiation of the radiotherapeutic system.

FIG. 8 shows an example of a form of measuring the scattering radiation. Therefore, the form of measuring the scattering radiation according to the examples not limited to the example. For example, as shown in FIG. 9, also by moving the detection face of the detector 301 (and the opening face of the collimator 303) interlockingly with the movement of the position of the axis of the therapeutic radiation beam while keeping the angle formed between the detection face and the irradiation direction of the therapeutic radiation beam constant, three-dimensional scattering radiation data made of a plurality of items of two-dimensional scattering radiation data can be obtained.

[Pre-process (Correction Process and the like) in Step S3b]

The correction processor 501 in the data processing system 5 executes pre-process including attenuation correction and obtains projection data (step S3). The attenuation correction is a correction process on signal attenuation caused by propagation of the therapeutic radiation and scattering radiation in a subject.

[Image Reconstruction Process in Step S4b]

Next, the reconstruction processor 503 in the data processing system 5 executes an image reconstruction process using the obtained projection data to obtain scattering radiation volume data (step S4).

[Conversion Process in Step S5b]

In a manner similar to the first example, the conversion processor 505 in the data processing system 5 converts the scattering radiation volume data to absorption dose volume data indicative of the three-dimensional distribution of the absorbed radiation dose (absorption dose) (step S5).

[Generation of Absorbed Dose Image Data/Display of Image Data in Steps S6b and S7b]

Next, the data processor 507 combines absorption dose image data with morphology image volume data, which has a subject captured by CT etc., and, further, generates an image for display. The image for display is a two-dimensional image of a section including, for example, a site to be treated, in which distribution of an absorption dose and morphology image are superimposed (step S6b). The display unit 6 displays an absorption dose image in a predetermined form (step S7b).

The operation of the modules in the data processing system will be described in detail.

(Fusion Model Module)

Processes of the fusion model module 511 will be described.

[Configuration of Fusion Model Data]

Figure 10:
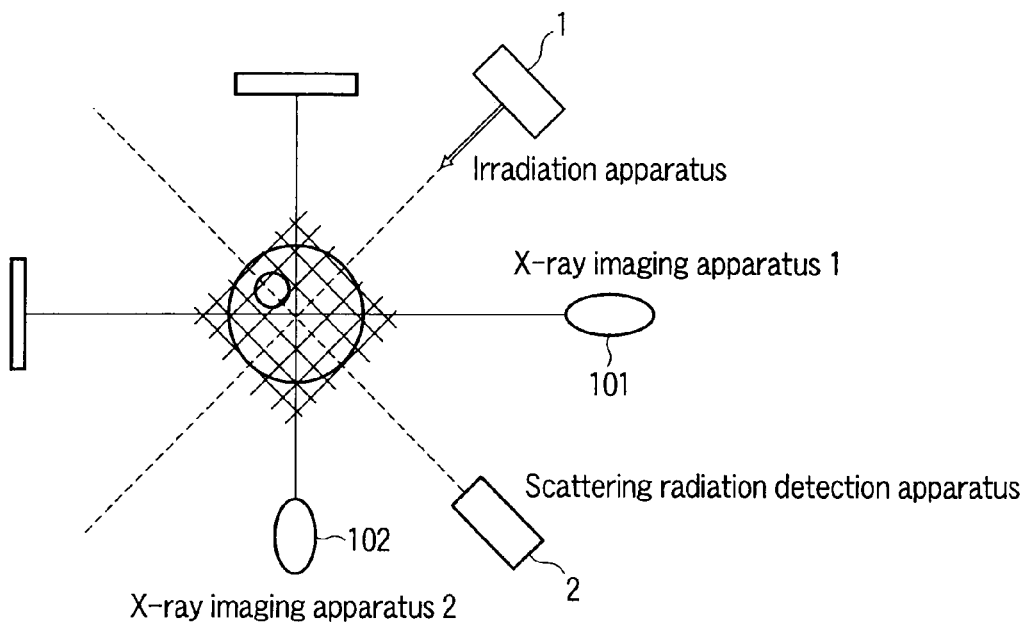
FIG. 10 is a diagram showing the positional relations of the systems.

FIG. 10 shows the positional relations of the irradiation system 2, the scattering radiation detection system 3, and X-ray imaging systems 101 and 102.

The X-ray imaging systems 101 and 102 are means for measuring a morphology image from a plurality of directions. Although the X-ray imaging systems 101 and 102 are shown as an X-ray bi-plane system in the embodiment, they may be CT apparatuses, MRI apparatuses, ultrasonic apparatuses, or the like. Images captured by the imaging apparatuses are stored as the morphology image data 705 in the storage unit 7.

Figure 11:
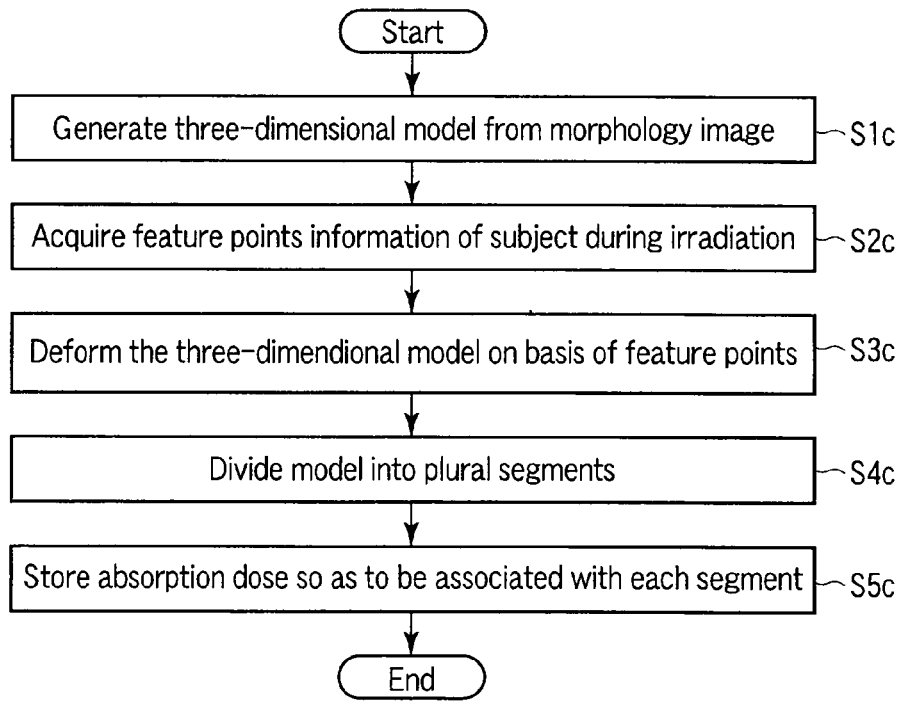
FIG. 11 is a flowchart showing a process procedure of a fusion model module.

FIG. 11 is a flowchart showing the procedure of the process of the fusion model module 511.

In FIG. 11, the fusion model module 511 generates a three-dimensional model image as the base of a fusion model by arbitrarily combining three-dimensional images (for example, a morphology image, a metabolism image, and a function image) of a CT, a PET, or the like obtained before radiotherapy treatment in the morphology image 705 stored in the storage unit 7 (step S1c).

Since the three-dimensional model image is combined with absorption dose volume data, it should show the position, size and shape of organs or tissues in a subject under irradiation. For regions which undergo less deformation such as brain, it is possible to use the three-dimensional model generated from an image prior to therapy. However, for regions subject to deformation such as abdominal organs, since there are cases in which the position, size and shape of the organ under irradiation differs significantly from those prior to therapy, it is favorable to obtain a real-time image which captures the subject in real time. For example, in an MRI integrated radiation therapy apparatus, it is possible to capture an image of a subject under irradiation or an image extremely close to its image. In a case where such image cannot be captured, a subject image model under irradiation can also be generated by deforming the subject image prior to irradiation appropriately.

Further, the fusion model module 511 uses CT, an X-ray imaging apparatus, an optical position measuring sensor, or the like during the radiation therapy to obtain images or position information of feature tissues such as bones and tumor in the subject and structures such as markers placed on the subject as feature points (step S2c).

The fusion model module 511 generates a three-dimensional model which imitates the subject under irradiation from the three-dimensional image of CT or PET which was obtained prior to irradiation therapy by extracting feature tissue/structure corresponding to the feature points obtained in step S2c and deforming them appropriately so as to fit the information obtained during therapy (step S3c). The fusion model module 511 divides the three-dimensional model which imitates the subject under irradiation into a plurality of segments (step S4c). The minimum unit of segments is a voxel size of the absorption dose volume data.

The fusion model data 709 for storing the absorption dose volume data 704 is constructed so as to be associated with the divided segments (step S5c). The associating operation is performed, for example, using the result of fitting of the feature points of the three-dimensional model and the real-time image and the mechanical positional relation between the X-ray imaging apparatus that has captured the real-time image and a scattering radiation detection apparatus as the base of generating the absorption dose volume data or the irradiation therapy apparatus. As a result, the absorption doses corresponding to the plurality of segments are stored as fusion model data. A fitting parameter for associating the segments and the mechanical positional relation are also stored as a part of the fusion model data.

Further, parameters (attribute information) such as "X-ray absorbance", "function information", and "radiation sensitivity" on the fusion model data 709 are associated with the segments and stored in a manner similar to the above. The X-ray absorbance can be obtained from a CT value obtained from another modality, X-ray absorption coefficient, or the like. The function (MI) information and the metabolism information is obtained from PET or MRS images or the like. In particular, by a molecule imaging image using PET or the like, activation level of a cancer, a low oxygen state, and the like can be grasped. When a tissue site or a target region to be treated can be specified, the radiation sensitivity can be also grasped from pre-held information of a database (table information of tissues and radiation sensitivities).

[Display of Absorption Dose Using Fusion Model Data]

By using the fusion model data 709, an image showing an absorption dose of an arbitrary section can be displayed on the display unit 6. Using "position information in the irradiation direction based on the position of the irradiation beam axis obtained from the irradiation therapy apparatus" and "the mechanical positional relation between the scattering radiation detection apparatus which is stored as a part of fusion model data or the irradiation therapy apparatus", for example, an image of a section perpendicular to the irradiation direction and an image of a section horizontal to the irradiation direction are generated.

With respect to accumulated information of the radiation absorption dose, by performing a fusing process on a reconstruction result of absorption doze of each time every measurement and associating it with each segment on the fusion model, then, storing it, the information of radiation absorption dose accumulated on the target site and the tissue site can be displayed. To specify a display region, tissue recognition is performed on the fusion model image of a tissue designated by the operator. There are a method of performing tissue recognition by designation of an operator, and a method of automatically performing segmentation and performing tissue recognition by selecting a tissue site or a target site.

Display examples of the generated fusion model will be described below.

DISPLAY EXAMPLE 1

Figure 12C:
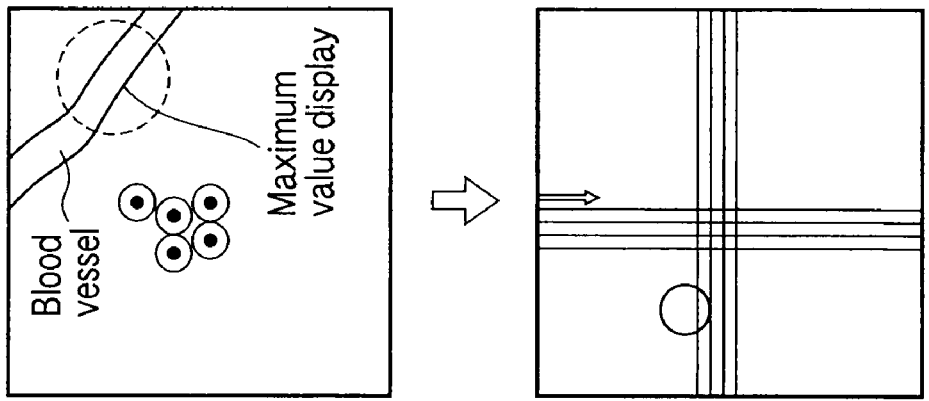
FIG. 12C is a display example of an absorption dose image displayed by fusion model data.
Figure 12B:
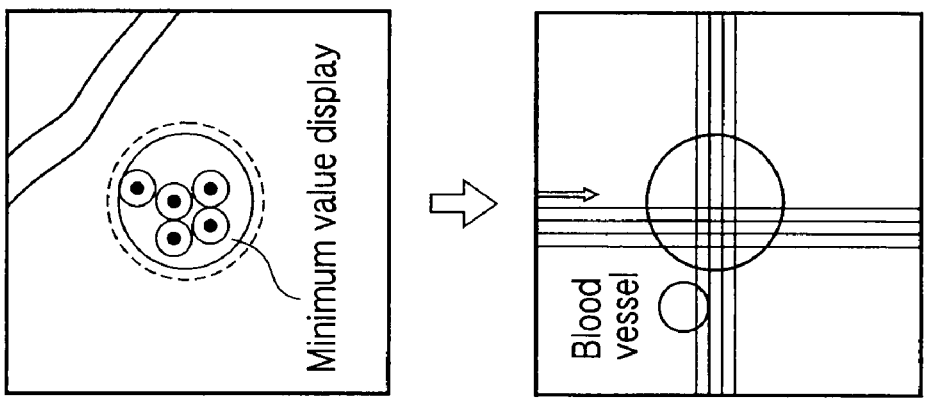
FIG. 12B is a display example of an absorption dose image displayed by fusion model data.
Figure 12A:
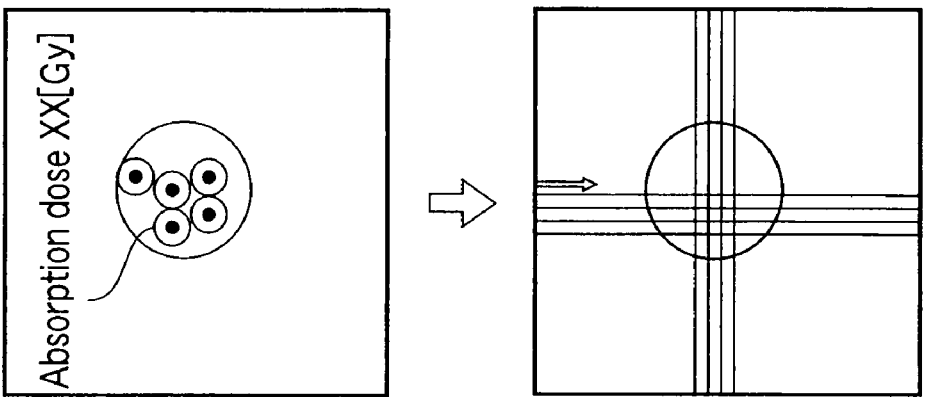
FIG. 12A is a display example of an absorption dose image displayed by fusion model data.

FIGS. 12A to 12C show an example of an absorption dose image displayed by the fusion model. Images in the upper stage of FIGS. 12A to 12C are cross sections perpendicular to the irradiation direction of the therapeutic radiation beam. Images in the lower stage are cross sections horizontal to the irradiation direction of the therapeutic radiation beam. FIG. 12A shows an example of display including a tumor (therapy target region) on which a radiation irradiated part and an accumulated absorption dose are superimposed. FIG. 12C displays a tissue (risk organ: risk region) existing near a therapeutic radiation beam passing region and relatively weak to irradiation. By displaying the irradiation history and the accumulated value, whether radiation does not exceed exposure limit or not can be confirmed on site. FIG. 12B shows an example of display where the images of FIGS. 12A and 12C are superimposed.

Although each of FIGS. 12A to 12C shows an example of displaying a section including a tumor and a risk organ, it may display an image with thickness including a tumor and a risk organ. In this case, as shown in FIGS. 12B and 12C, as the accumulated dose, a numerical value calculated by minimum intensity projection is shown in a tumor. A numerical value calculated by maximum intensity projection is shown in a risk organ. The accumulated dose may be displayed in certain slice pitches. The accumulated absorption dose may be displayed in numerical value, color, or brightness.

DISPLAY EXAMPLE 2

FIGS. 13A to 13C show a display example of an absorption dose image with respect to radiation sensitivity threshold indication. Images in the upper stage of FIGS. 13A to 13C are cross sections perpendicular to the irradiation direction of a radiation beam. Images in the lower stage are cross sections horizontal to the irradiation direction of the therapeutic radiation beam.

As shown in FIG. 13B, when the absorption dose does not exceed a predetermined therapeutic radiation dose in a region desired to be treated (cancer target site), a warning is displayed. For example, when the absorption dose does not exceed a threshold, the region is displayed in another color. On the contrary, as shown in FIG. 13C, when the absorption dose reaches the threshold on the outside of the treatment target range, in particular, in a tissue region having high radiation sensitivity, a warning is displayed. For example, when the absorption dose exceeds the threshold, an image is displayed in another color.

DISPLAY EXAMPLE 3

Figure 14C:
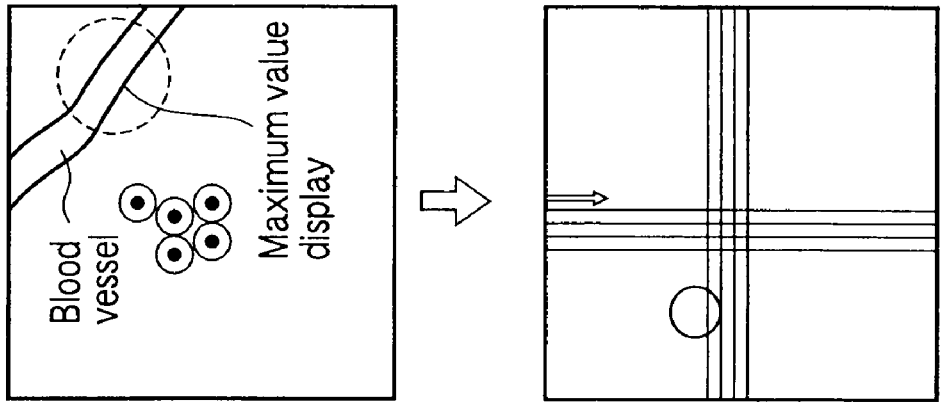
FIG. 14C is a display example of an absorption dose image in the case where molecular level activation degree information is added.
Figure 14B:
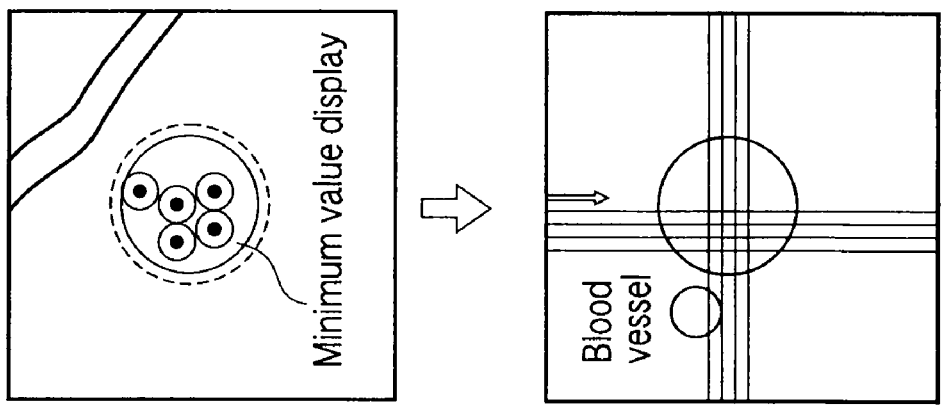
FIG. 14B is a display example of an absorption dose image in the case where molecular level activation degree information is added.
Figure 14A:
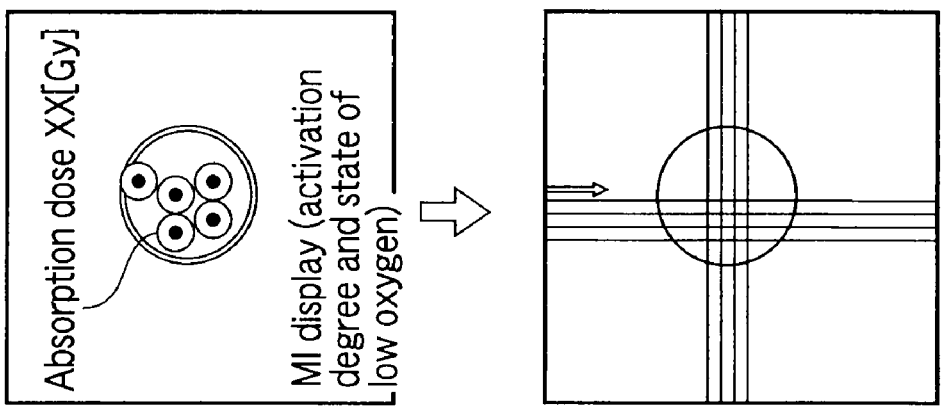
FIG. 14A is a display example of an absorption dose image in the case where molecular level activation degree information is added.

FIGS. 14A to 14C show a display example of an absorption dose image in the case where molecule level activation degree information is added. Images in the upper stage of FIGS. 14A to 14C are cross sections perpendicular to the irradiation direction of the radiation beam. Images in the lower stage are cross sections horizontal to the irradiation direction of the therapeutic radiation beam.

By utilizing the molecular imaging technique using a molecular diagnostic product typified by FDG, a low-oxygen state and cancer activation degree are superimposed.

As described above, by using the fusion model data in which the absorption dose is associated with a three-dimensional model, an absorption dose image at an angle perpendicular to irradiation or an arbitrary angle can be displayed in real time during treatment. An accumulated absorption dose image in which an absorption dose per irradiation of the therapeutic radiation beam can be generated, and a radiation sensitivity threshold, the molecular-level activation degree information, and the like can be superimposed. In particular, a two-dimensional image can be provided, by which whether an absorption dose (accumulated absorption dose) in a target region or a risk region exceeds a threshold or not can be determined by displaying a target region and a risk region in an image at an angle perpendicular to the irradiation and superimposing the absorption dose or accumulated absorption dose by maximum intensity projection or minimum intensity projection. Since an absorption dose having three-dimensional information can be provided to the operator on a two-dimensional image, an effect is produced such that determination of the operator becomes easier.

(Plan Evaluation Module)

The processes of the plan evaluation module 513 will now be described.

FIRST EXAMPLE

Figure 15:
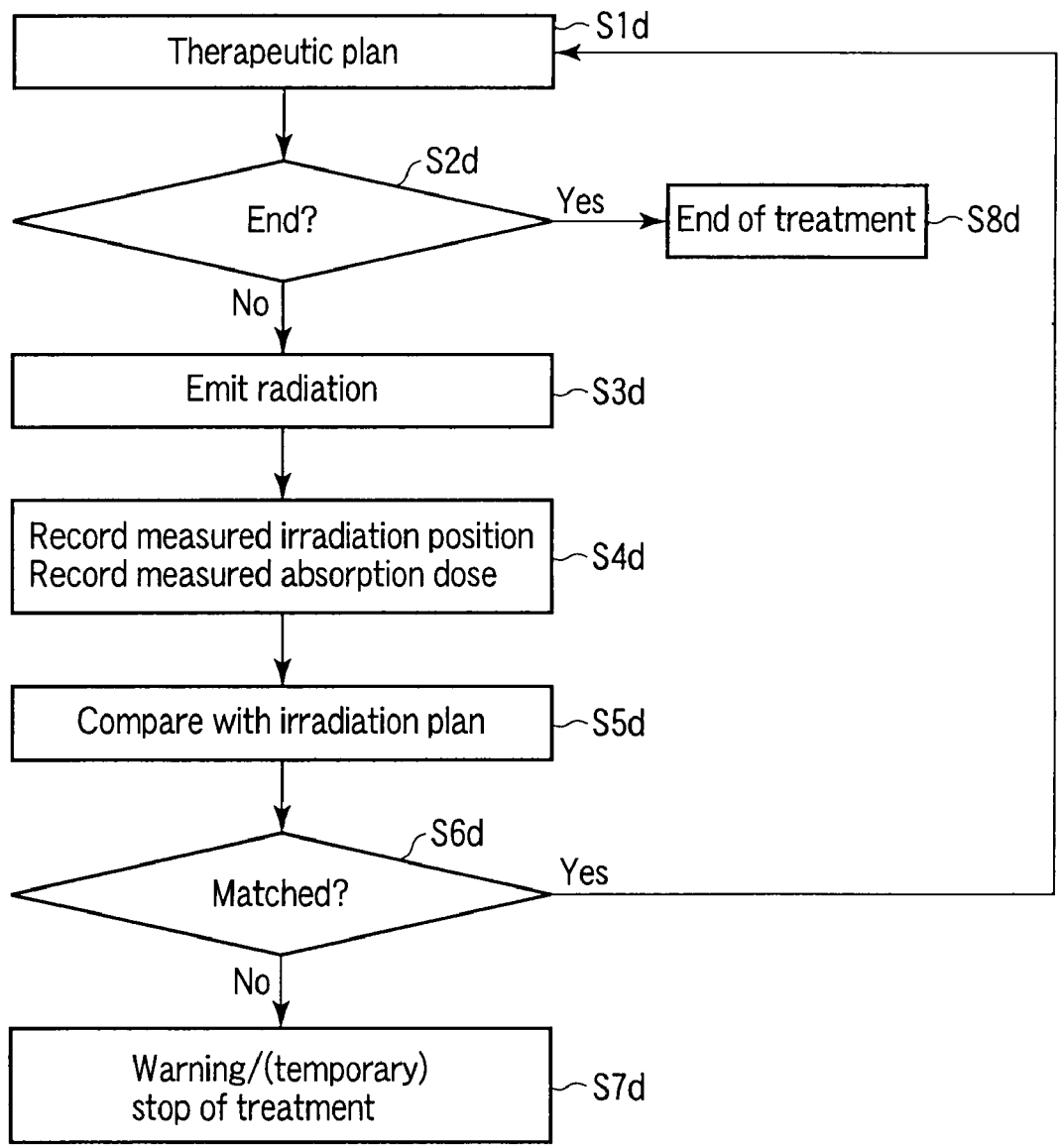
FIG. 15 is a diagram showing an example of a workflow of radiotherapy treatment of the radiotherapeutic system.

FIG. 15 shows an example of a workflow of radiotherapy treatment in the radiotherapeutic system 1 according to the present invention. Along the workflow, a first example of the plan evaluation module 513 will be described.

[Acquisition of Therapeutic Plan in Step S1d]

In FIG. 15, first, a therapeutic plan such as an irradiation method (irradiation position and the number of times) and the like for a patient is determined in advance prior to a therapy by the operator and the like on a therapeutic planning apparatus and is stored as the therapeutic plan data 707 in the storage unit 7 via the network interface 9. The details of the therapeutic plan will be described later.

[Irradiation of Radiation in step S3d]

As shown in FIG. 6, at the start of therapy, the patient is fixed in the same position as that in the therapeutic plan on the bed of the irradiation system 2. When the operator presses a therapy start button (not shown), a therapy start signal is transmitted to the data acquisition controller 4. The data acquisition controller 4 reads the therapeutic plan data 707 from the storage unit 7 and, according to the therapeutic plan, controls the irradiation system 2. As a result, a determined position in the patient is irradiated with radiation from the irradiation system 2.

[Recording of Irradiation Position and Absorption Dose in Step S4*d*]

At the time of emitting radiation from the irradiation system 2, the data acquisition controller 4 controls the scattering radiation detection system 3 and measures the irradiation position of the radiation emitted from the irradiation system 2 to the patient and the scattering radiation dose generated by the irradiation. The data processing system 5 obtains the irradiation position and absorption dose from the measured scattering radiation dose by the conversion processor 505. The obtained irradiation position (hereinbelow, measured irradiation position) and the absorption dose (hereinbelow, measured absorption dose) are time-sequentially stored in the storage unit 7.

[Comparison between Irradiation Plan and Measurement Value in Step S5*d*]

Once the irradiation completes, the plan evaluation module 513 manually or automatically calls the therapeutic plan data 707, the measured irradiation position, and the measured absorption dose amount stored in the storage unit 7 and displays it on the screen of the display unit 6. For example, as shown in FIG. 16A, the measured value is superimposed on a plan image (such as a CT image captured before the operation) as shown in FIG. 16A. FIG. 16A shows that the planned irradiation position and the measured irradiation position are superimposed, so that a deviation of the irradiation position can be grasped at a glance.

Figure 17:
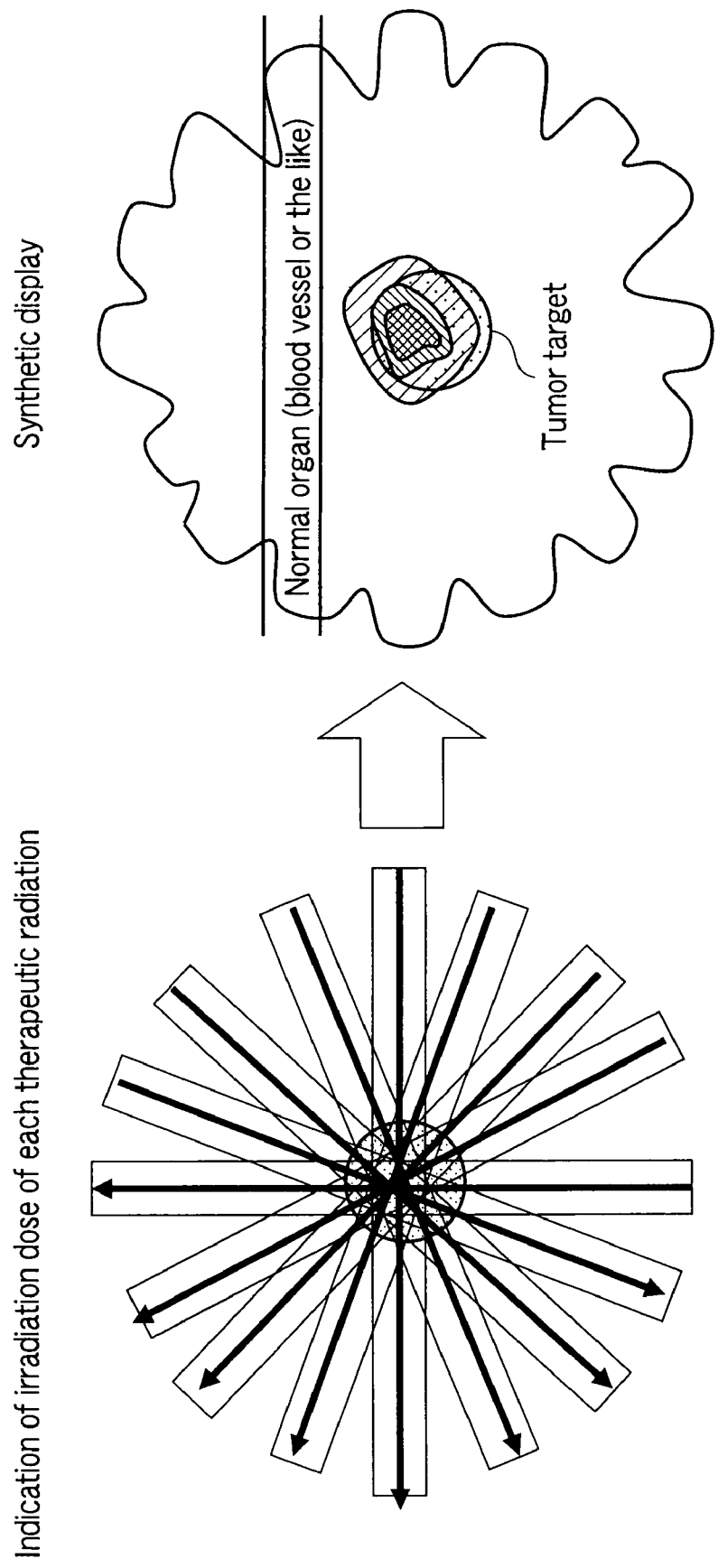
FIG. 17 is a diagram showing an example of a display image generated by the plan evaluation module.

Further, the planned irradiation dose and the measured absorption dose amount are compared by the plan valuation module 513. Whether there is the difference or not, if there is the difference, the value of the difference, and determination of whether the difference value is permissible or not are understandably displayed to the operator. They can be expressed in, for example, a table form as shown in FIG. 16B or a graph form as shown in FIG. 16C. Further, as shown in FIG. 16B, it is preferable to display a risk organ sensitive to radiation such as the heart so as to be emphasized to promote awareness. As shown in FIG. 17, it is also possible to overlap absorption doses of radiations, represent the absorption doses to a tumor target in contour, and superimpose the contour on the morphology image of a site to be treated.

[Match Determination in Step S6*d*]

When the plan evaluation module 513 compares the therapeutic plan and the measured value with each other and finds that they match perfectly or the difference lies in the permissible range, the data acquisition controller 4 manually or automatically transmits a signal to start the next irradiation by the irradiation system 2. The irradiation system 2 irradiates the radiation of the amount based on the therapeutic plan to a position based on the therapeutic plan. As long as the therapeutic plan and the measured value match or the difference lies in the permissible range, unless otherwise a special change occurs, the works in the steps S1*d* to S6*d* in FIG. 15 are repeated until the end of the plan ("End in step S8*d*" of the workflow).

In the storage unit 7, the measured irradiation position and the measured absorption dose per irradiation and the difference between the measured value and the plan value are stored time-sequentially. As necessary, the operator can make an integration value or the like of the absorption dose in arbitrary time and in an arbitrary position during therapy calculated and displayed.

[Warning in Step S7*d*]

On the other hand, when the difference which cannot be permitted occurs between the therapeutic plan and the measured value, as shown in the step S7*d* in FIG. 15, a warning is output by the plan evaluation module 513 and the treatment operation of the irradiation system 2 is (temporarily) stopped. When all of the treatments are finished according to the therapeutic plan, by a change in the therapeutic plan, or cancellation of the therapy, the plan evaluation module 513 stores, as a set, a series of therapeutic data (the measured irradiation position and the measured absorption dose per irradiation, the difference between the measured value and the plan value, and the like) into the storage unit 7. For example, the data set can be used for confirmation of the therapeutic effect, reflected to the next therapeutic plan, and used for examination of the late influence of radiation.

SECOND EXAMPLE

Figure 18:
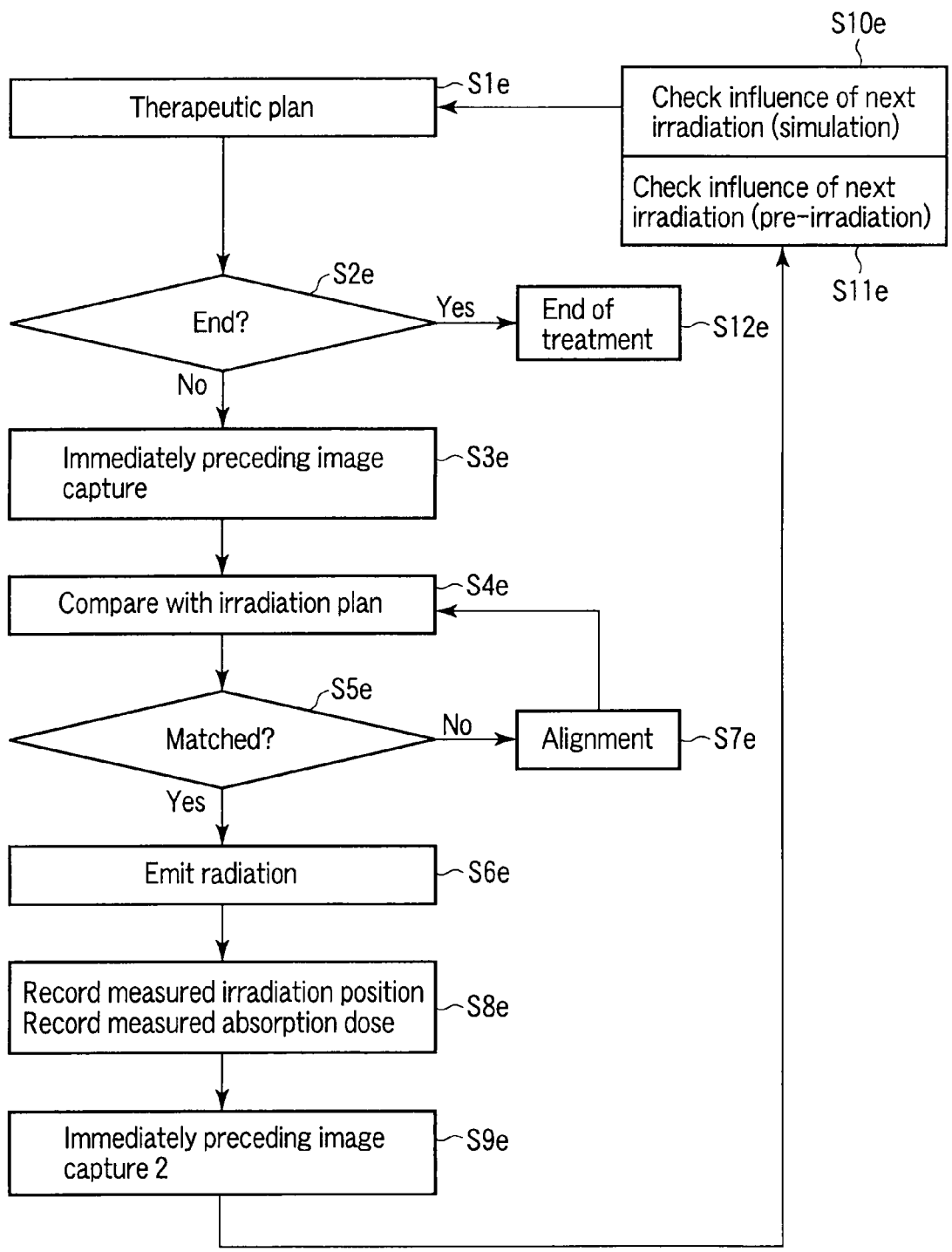
FIG. 18 is a diagram showing another example of a workflow of radiotherapy treatment of the radiotherapeutic system.

FIG. 18 shows another example of a workflow of radiotherapy treatment in the radiotherapeutic system 1 according to the present invention. Along the workflow, a second example of the plan evaluation module 513 will be described.

[Therapeutic Plan in Step S1*e*]

First, a therapeutic plan such as an irradiation method and the like for a patient is determined in advance prior to a therapy by the operator and the like on a therapeutic planning apparatus (not shown) on a network and is stored in the storage unit 7 (the details of the therapeutic plan will be described later).

[Immediately Preceding Image Capturing in Step S3*e*]

At the start of therapy, the patient is fixed in the same position as that in the therapeutic plan on the bed of the irradiation system 2. The operator operates the imaging apparatuses 101 and 102 disposed as shown in FIG. 10 to capture an image just before therapy of an irradiation region in the patient. As the imaging apparatuses 101 and 102, for example, an X-ray imaging apparatus, an X-ray CT apparatus, a 3D ultrasonic diagnostic apparatus, or the like can be used. The coordinates of the therapeutic planning apparatus, the imaging apparatuses 101 and 102, and the irradiation system 2 have to be positioned. The positioning of the coordinates is executed by the fusion model of the data processing system as described above. It is also possible to use, as a base point, the coordinates of an arbitrary point on the bed at the time of therapy, a marker placed on a part of the patient, and a region having a characteristic as a landmark in or out of the body of the patient. It is assumed here that the positions of all of images are adjusted to the center of irradiation of the irradiation system 2.

[Comparison between Radiation Plan and Immediately Preceding Image in Step S4*e*]

Figure 19:
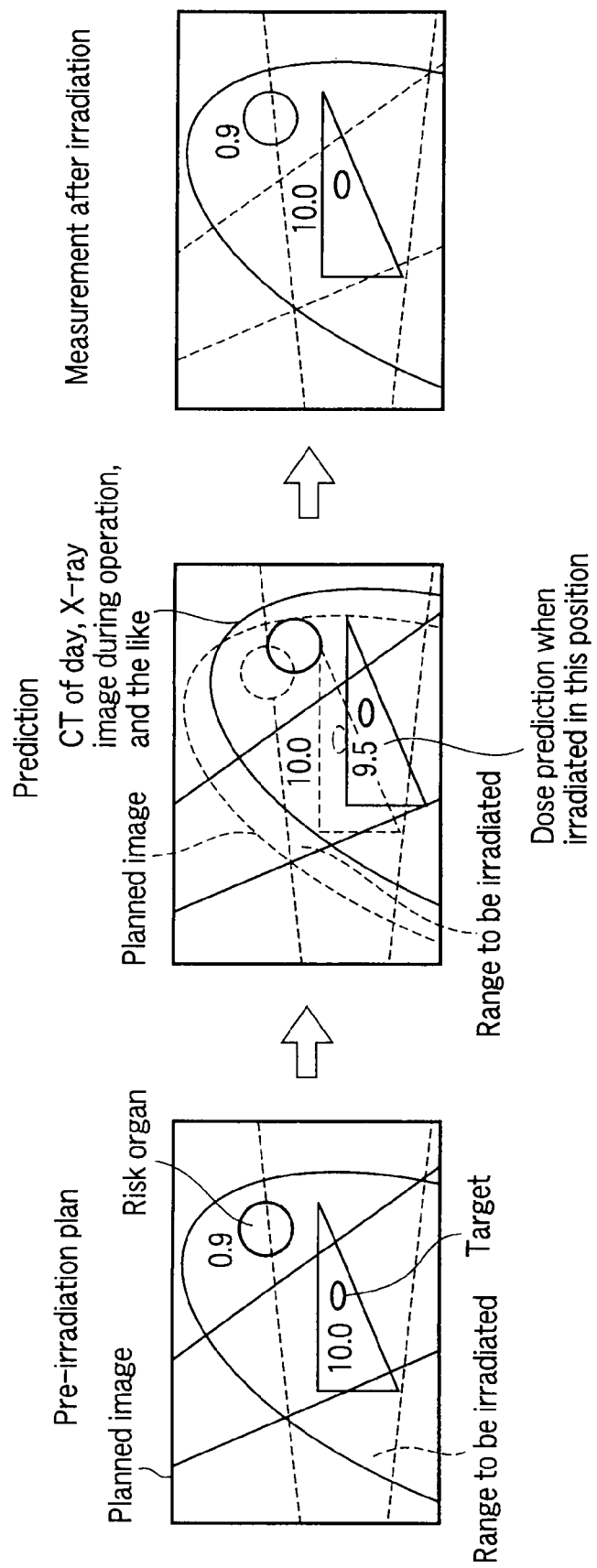
FIG. 19A shows an example of a display image generated by the plan evaluation module.
FIG. 19B shows an example of a display image generated by the plan evaluation module.
FIG. 19C shows an example of a display image generated by the plan evaluation module.

FIG. 19A shows a plan image showing an irradiation position based on the therapeutic plan. The plan evaluation module 513 overlaps a therapeutic plan image and an image just before treatment as shown in FIG. 19B and displays them on the display of the display unit 6.

[Match Determination in Step S5*e*]

By the display, whether there is a positional deviation exerting an influence on therapy or not is visually recognized by the operator. Highest priority is given to a serious positional deviation such as deviation of the position of an object to be treated such as a tumor from an irradiation position, or deviation of the position of a risk organ sensitive to radiation into the radiation passage region.

[Positioning in Step S7e]

In the case where such a serious positional deviation occurs, the operator moves a patient or bed so as to match the position in the therapeutic plan.

Detection of a positional deviation is not limited to the visual check of the operator but can be also automatically performed on the basis of a predetermined marker position on an image, the contour of an organ, a feature amount, or the like. FIG. 20 is a flowchart showing the procedure of the positioning process in this case. The plan evaluation module 513 automatically detects the positional deviation from a predetermined marker position on an image, the contour of an organ, a feature amount, or the like (step S1f). When the positional deviation is within the permissible range, the irradiation is continued (step S3f). On the other hand, when the positional deviation is detected on the outside of the permissible range, the plan evaluation module 513 displays a warning to perform the positioning on the display unit 6 (step S2f). In the case where a positional deviation out of the permissible range occurs (YES in step S2f), therapeutic operation of the irradiation system 2 is temporarily stopped (step S4f), the operator moves the patient or the bed so as to match the position on the therapeutic plan (step S5f). In the case where the invention is not limited to the visual check of the operator but in any of visual detection and automatic detection, if a series positional deviation is detected, to prevent a medical accident, desirably, the data acquisition controller 4 warns the operator, or the radiotherapeutic system 1 is locked so as not to operate.

[Irradiation in Step S6e]

When the operator confirms that the positional deviation of the patient lies in the permissible range of the therapeutic plan, in response to an operation of depressing a button or the like of the operator, the data acquisition controller 4 drives the irradiation system 2 to emit radiation to the patient as shown in FIG. 19C on the basis of the therapeutic plan.

[Recording of Measured Irradiation Position and Measured Absorption Dose in Step S8e]

At the time of emitting radiation from the irradiation system 2, the data acquisition controller 4 controls the scattering radiation detection system 3 and measures the irradiation position of the radiation emitted from the irradiation system 2 to the patient and the scattering radiation dose generated by the irradiation. The data processing system 5 obtains the measured irradiation position and measured absorption dose from the measured scattering radiation dose by the conversion processor 505. The measured irradiation position and the measured absorption dose are time-sequentially stored in the storage unit 7.

[Immediately Preceding Image Acquisition 2 in Step S9e]

After completion of the irradiation, the plan evaluation module 513 captures again an image just before therapy of the patient. Since there is a case that a positional deviation occurs due to deformation of an organ during therapy in addition to motion of the patient due to insufficient fixing, it is desirable to check the surrounding of a object to be treated almost in real time in order to perform accurate therapy. When it is determined that an object to be treated is deviated out of the permissible range, the therapeutic operation of the irradiation system 2 has to be stopped, and the patient or bed has to be moved to a correct position.

[Confirmation of Influence of Irradiation of Next Time in Step S10e]

Figures 21A, 21B, 21C:
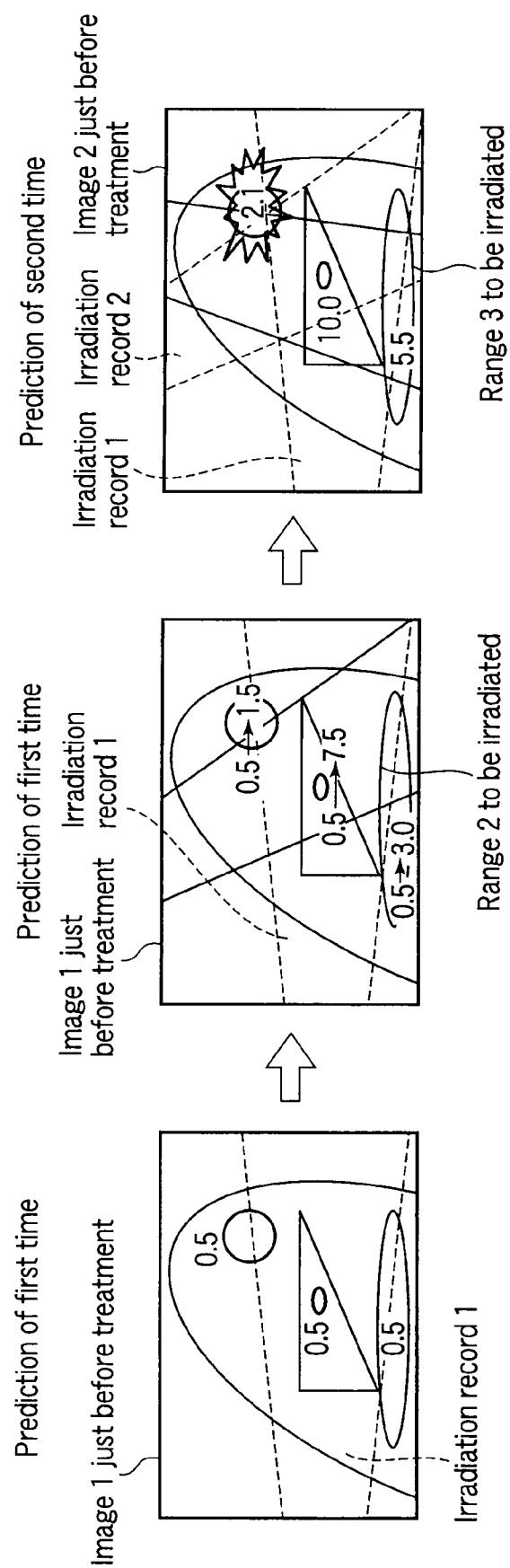
FIG. 21A shows an example of a display image generated by the plan evaluation module.
FIG. 21B shows an example of a display image generated by the plan evaluation module.
FIG. 21C shows an example of a display image generated by the plan evaluation module.

The result of the therapy (the measured irradiation position and the measured absorption dose) stored in the storage unit 7 is superimposed on the immediately preceding image captured, and the resultant image is displayed on the display of the display unit 6 (FIG. 21A).

A simulation of the influence of the irradiation of the next time exerted on the target to be treated and peripheral organs will be described with reference to FIGS. 21A to 21C. FIG. 21A shows an image in which the immediately preceding image and the therapy result are overlapped and displayed. The measured irradiation position is shown by a line and the measured absorption doses are indicated by numbers. FIG. 21B shows an image obtained by calling the next therapeutic plan from the storage unit 7 and superimposing it on an image in which the immediately preceding image and the therapeutic result are overlapped.

First, the next scheduled irradiation position and irradiation dose in the therapeutic plan are displayed as they are. A check is made to see whether the therapeutic target is correct or not and whether irradiation in the permissible range is performed to a risk organ or not. More preferably, a simulation of the influence of the next therapy on the therapy result at present is made to confirm that the radiation dose is not excessive or insufficient. A method of adding the present measured absorption dose to the radiation dose of the plan to be irradiated next while performing positioning using the fusion model and displaying the resultant value is used. A radiation dose of the plan to be irradiated next is obtained in consideration of absorption and scattering of radiation by using the Monte Carlo method or the like, and a predictive value obtained by adding the radiation dose to the accumulated value of the measured absorption dose is displayed. It is also possible to show the simulation result in the diagram as shown in FIG. 21C, and express the present state and the simulation result in a table form as shown in FIG. 22.

As shown in FIG. 21C, when the predictive value exceeds the predetermined irradiation permissible value, the plan evaluation module makes a warning by warning means such as sound, light, characters, and the like. For example, when the plan evaluation module 513 determines that the next irradiation plan is improper by the simulation on the basis of the flowchart of FIG. 23 (YES in step S1g), the therapeutic operation of the irradiation system 2 is temporarily stopped (step S3g). The operator is allowed to select to continue the therapy or interrupt the therapeutic plan (step S4g). For safety, the irradiation system 2 is automatically or manually locked so as not to operate.

[Confirmation of the Influence of Irradiation of Next Time in Step S11e]

Figure 24:
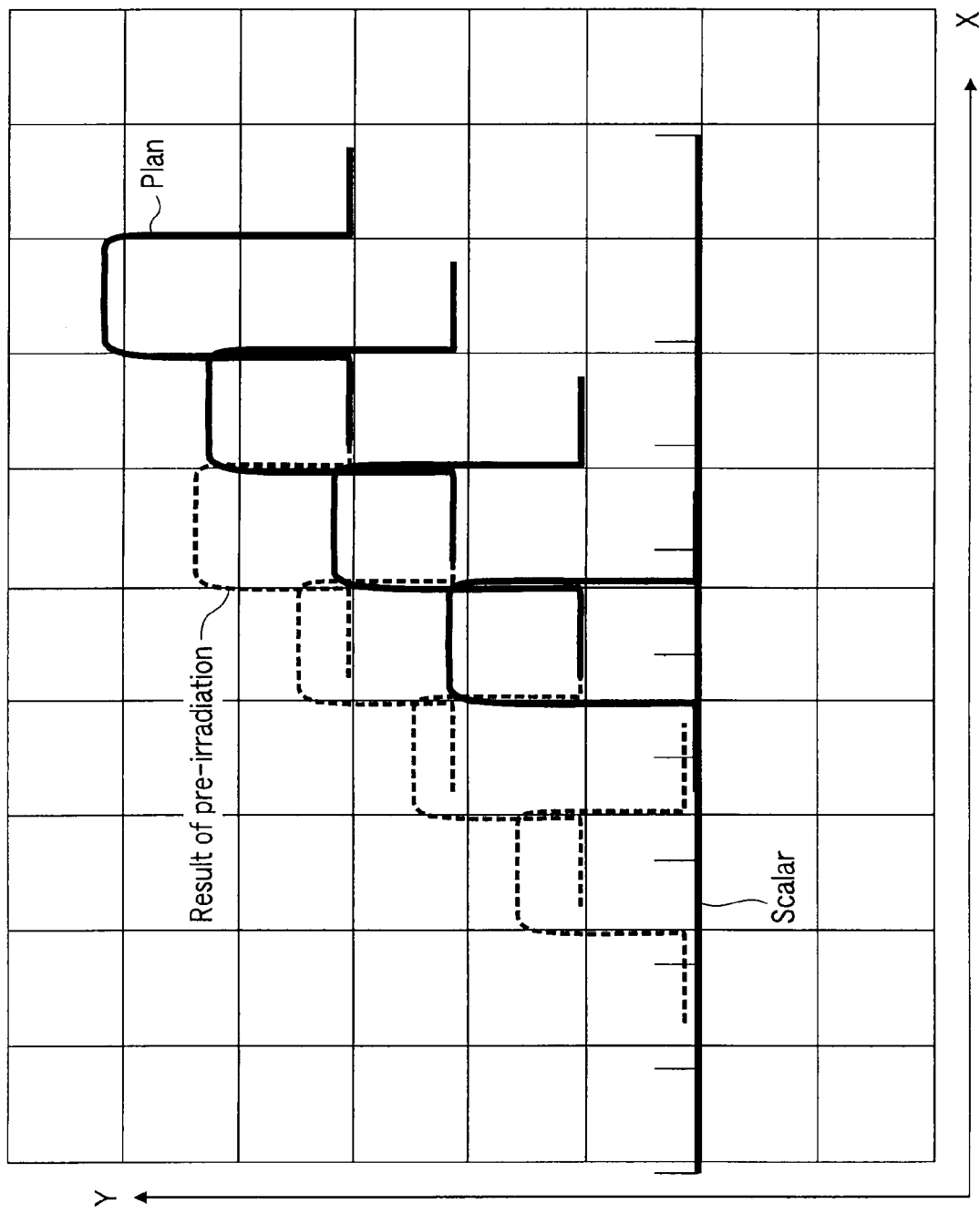
FIG. 24 is a diagram showing an example in which a scalar for determining a positional deviation between a planned image and a measured absorption line image is displayed.

The method of predicting the influence of the next irradiation of the therapeutic target and peripheral organs by simulation has been described above. To determine the influence more accurately, pre-irradiation may be performed. Radiation which is weak enough not to exert influence on the therapy is irradiated from the irradiation system 2 to the next irradiation planned position in the patient. The irradiation position is measured by the scattering radiation detection system 3. Whether or not there is a deviation between the plan and the measured position is determined by comparison between the therapeutic plan image and the measured absorption line image. A deviation may be automatically determined on the basis of values on an image such as a CT value. A scalar may be displayed on an image as shown in FIG. 24 so that a deviation amount may be visually confirmed.

(Therapeutic Plan)

An example of the therapeutic plan will be described with reference to FIGS. 25 to 29.

Figure 25:
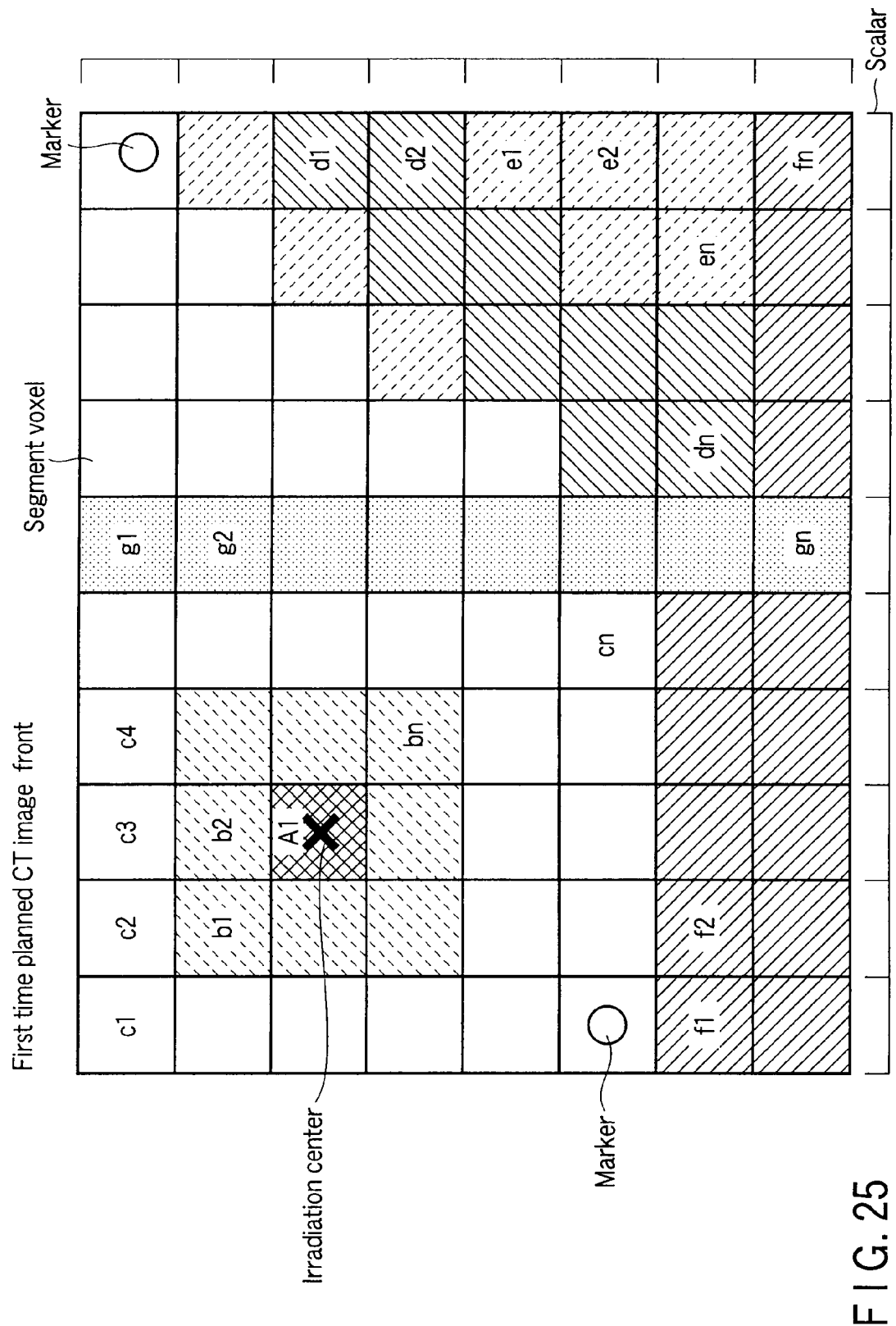
FIG. 25 is a diagram obtained by dividing a planned image into segments.

Since the permissible dose of a normal cell varies among organs, one of objects of the therapeutic plan is a device to emit the therapeutic radiation from the direction of an organ which is relatively resistive to radiation and minimize irradiation of an organ to which irradiation is to be avoided as much as possible. First, each of the organs is subject to segmentation in the plan image as shown in FIG. 25. Concretely, voxels belonging to the same organ (in practice, each voxel has a size of about 1 to 5 mm, but for convenience of explanation, larger voxels are shown. A group of some voxels may be expressed in a large quadrangular prism or the like) are registered in the same group. Groups include a liver malignancy group "a", a liver normal tissue group "c", a stomach normal tissue group "e", an intestine normal tissue group "f", a spinal normal cell group "g", . . . and the like. The segmentation may be performed automatically on the basis of information such as a CT value on the image or manually with a touch pen or the like.

Figure 26:
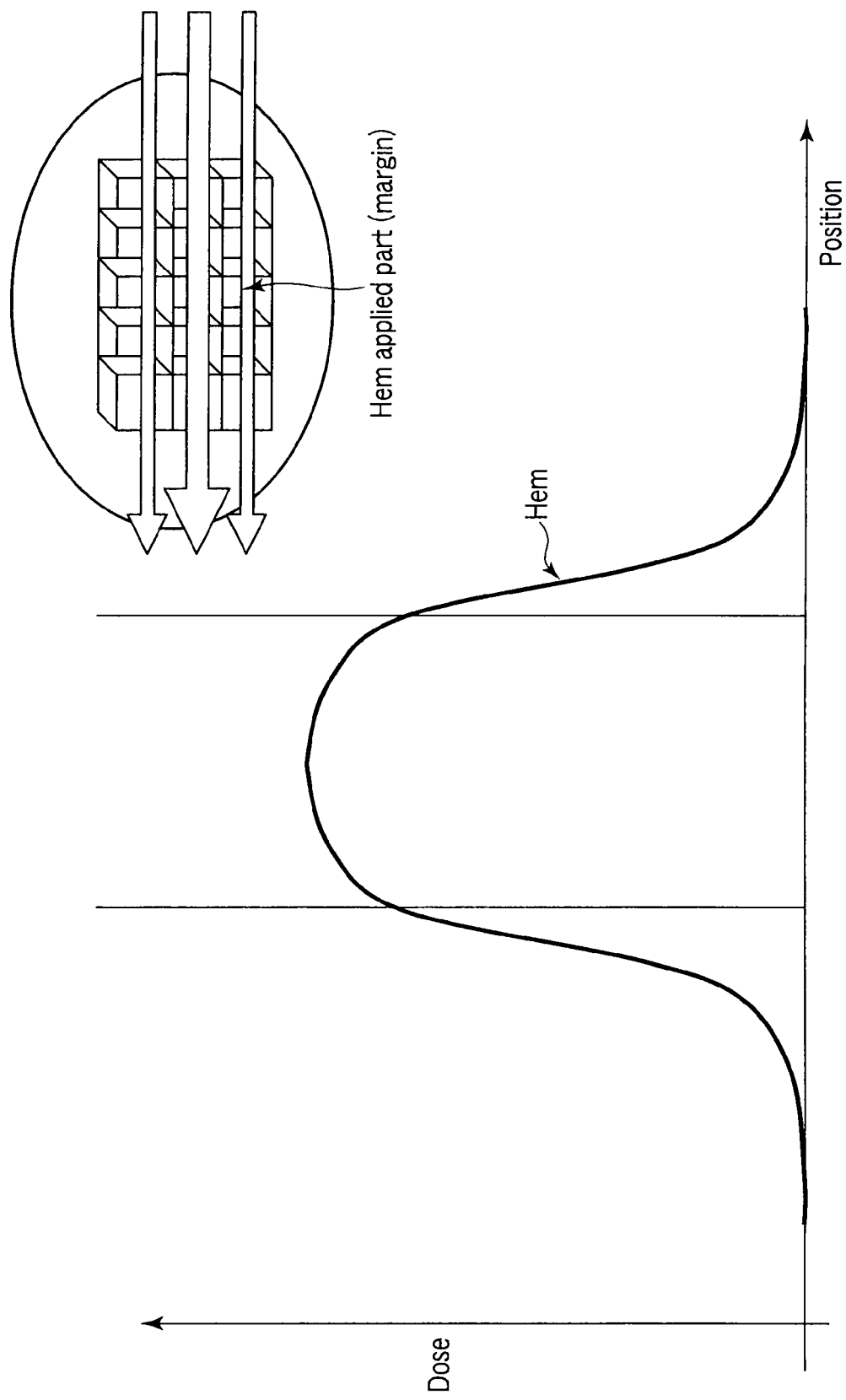
FIG. 26 is a diagram showing an irradiation range of a radiation beam.

In the case where a voxel in the border of organs belongs to a plurality of organs, when all of the organs have the normal tissues, the voxel is preferably registered as a voxel belonging to an organ having the smallest permissible dose. In this method, the risk of side effect is reduced. However, when a region of a tumor to be irradiated with a radiation dose of a predetermined value is included, it has to be registered as the region of the tumor. Since radiation has a hem as shown in FIG. 26, when a tumor is irradiated with a radiation beam, there is a normal tissue which is victimized. The range of normal tissues to be victimized is registered as a "margin region b".

Reference values of the normal tissue permissible dose are written in, for example, "Radiation Therapy Planning Guidelines 2004" issued by The Japanese College of Radiology.

In the embodiment, as shown in FIG. 4, the permissible dose table storing permissible doses of organs is stored in the storage unit 7. To each of the voxels, for example, like a table shown in FIG. 27, a region name arbitrarily given to an organ name and an address in a region are given. When the region name of the liver normal tissue is set as a region "c" and the number of voxels in the region "c" is "n", the addresses are c1 to cn.

Further, information of a permissible dose is given to each of the voxels. There is a case where the permissible dose is determined for each of arbitrary points (every cell) like normal tissues of the stomach, intestine, and spinal, and there is also a case where the permissible dose is determined to each of 1/3, 2/3, and 3/3 of the volume of an organ from the viewpoint of spare ability (refer to FIG. 27). In the regions of normal tissues of the stomach, intestine, and spinal, when it is determined that the radiation dose exceeds or seems to exceed the permissible dose in at least one voxel, warning is given. In the case of the region of the normal tissue of the liver, whether the radiation dose exceeds the permissible value or not is determined on the basis of two kinds of information; the percentage of the voxels of the liver irradiated with the radiation and an average value of radiation dose applied to the voxels (refer to FIG. 27).

On the other hand, information of the minimum value of radiation necessary for treatment is given to voxels belonging to a region "a" in malignancy to be treated. Whether the radiation exceeding the minimum value can be irradiated or not is finally the criterion of determination.

It is known that each of cells has a survival curve with respect to radiation as shown in FIG. 28. By actually measuring the absorption dose, the dose of radiation applied to the cell of a voxel can be known. Therefore, by the survival curve of the cells of an organ to which the voxel belongs, the survival rate of the cell is predicted and can be used for determination of whether the next irradiation can be performed as planned or not. A survival curve table is obtained from the therapeutic planning apparatus on the network and the survival rate of the cell of each voxel can be calculated. In the case where the radiation sensitivity which varies among individuals is known from gene information, the information can be reflected in the setting of the permissible dose. It is sufficient to obtain a gene information table of a patient from the therapeutic planning apparatus.

At the time of planning, as shown in FIG. 29, for example, the minimum value of the ratio of remaining tissues to the liver normal tissues is determined. When the survival rate of each voxel is calculated on the basis of the accumulated value of the measured absorption dose, the survival rate (or fatality rate) to all of the voxels of the liver normal tissues is calculated and checked with the minimum value which is set at the time of planning, and a warning is given.

The value of an error obtained from precision of the apparatus is also set for each of the voxels or each voxel group as shown in FIG. 30 and is reflected in the threshold of the permissible dose.

THIRD EXAMPLE

Using the workflow of FIG. 18, a third example of the plan evaluation module 513 will be described.

[Therapeutic Plan in Step S1e]

First, a therapeutic plan such as an irradiation method and the like for a patient is determined in advance prior to a therapy by the operator and the like on a therapeutic planning apparatus as shown in the table of FIG. 31 and is stored in the storage unit 7. In this example, fractionated irradiation of performing irradiation for three days, from three directions per day is assumed. A plan of irradiations of six times is expressed in a table or drawing on the display of the display unit 6.

[Immediately Preceding Image Capturing in Step S3e]

Figure 32:
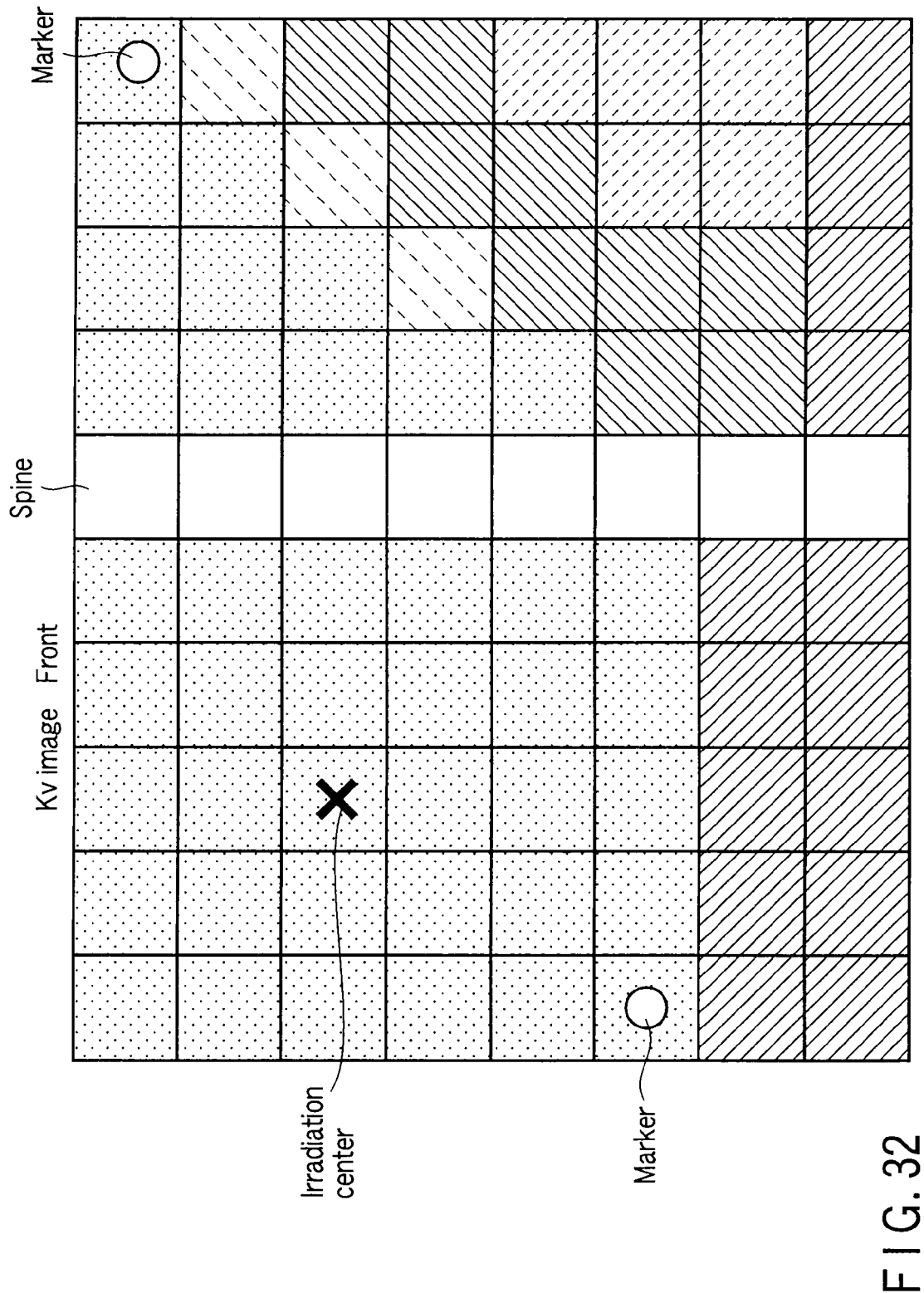
FIG. 32 is a diagram showing an example of an image just before therapy of an irradiation region.

At the start of therapy, the patient is fixed in the same position as that in the therapeutic plan on the bed of the irradiation system 2. The operator operates the imaging apparatuses 101 and 102 disposed as shown in FIG. 10 to capture an image just before therapy (FIG. 32) of an irradiation region in the patient. As the imaging apparatuses 101 and 102, for example, an X-ray imaging apparatus, an X-ray CT apparatus, a 3D ultrasonic diagnostic apparatus, or the like can be used. In this case, a kv image is obtained by using an X-ray fluoroscope apparatus integrated with the irradiation system 2. The coordinates of the therapeutic planning apparatus, the imaging apparatuses 101 and 102, and the irradiation system 2 have to match. As a method of matching the coordinates, it is possible to use, as a base point, the coordinates of an arbitrary point on the bed at the time of therapy, a marker placed on a part of the patient, and a region having a characteristic as a landmark in or out of the body of the patient. It is assumed here that the positions of all of images are adjusted to the center of irradiation of the irradiation system 2.

[Comparison between Irradiation Plan and Immediately Preceding Image in Step S4e]

Figure 33:
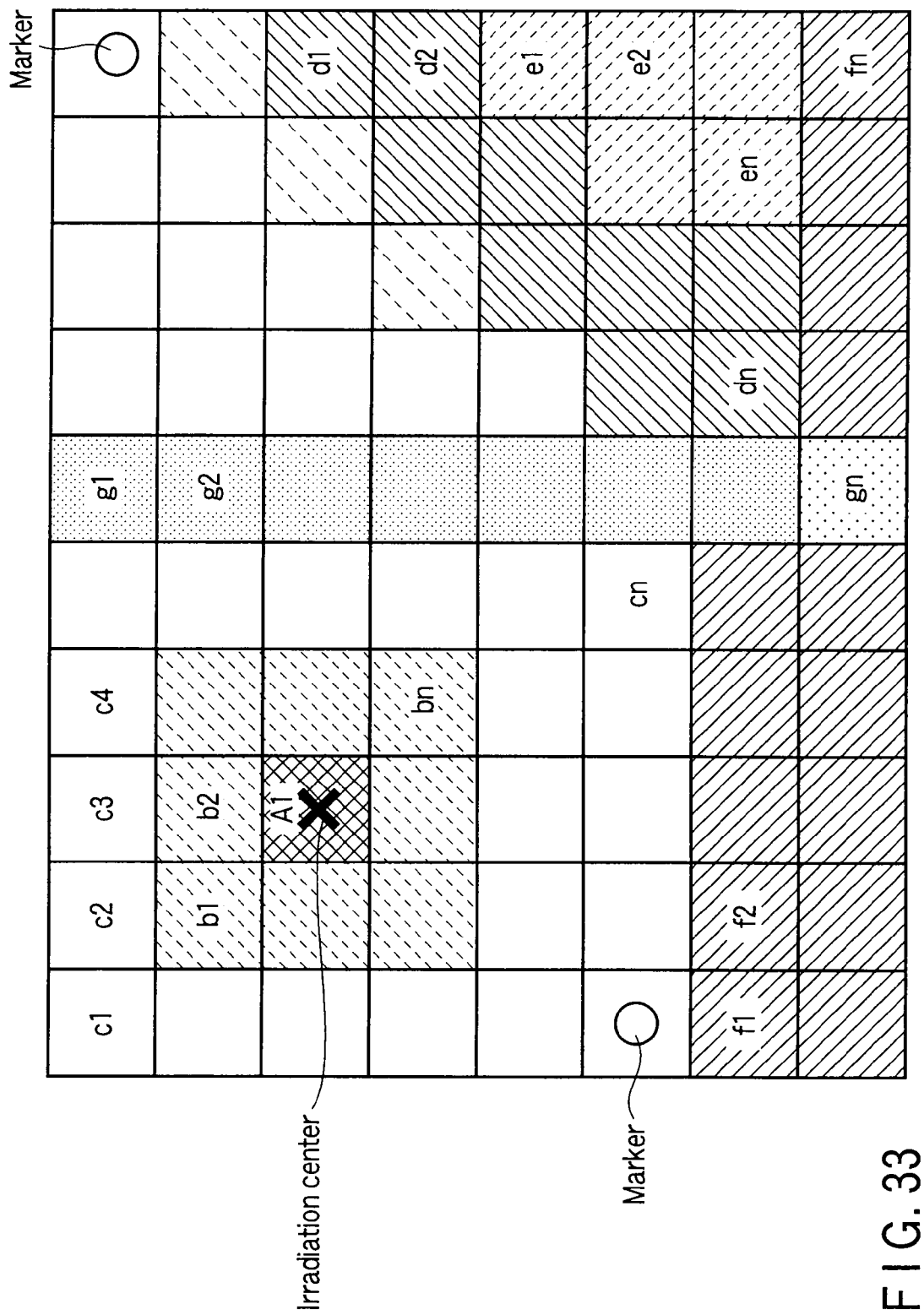
FIG. 33 is a diagram showing an example of a planned image and an image just before therapy.

The plan evaluation module 513 overlaps a therapeutic plan image and an image just before treatment as shown in FIG. 33 and displays them on the display of the display unit 6.

[Match Determination in Step S5e]

By the display, whether there is a positional deviation exerting an influence on therapy or not is visually confirmed by the operator. Highest priority is given to a serious positional deviation such as deviation of the position of an object to be treated such as a tumor from an irradiation position, or deviation of the position of a risk organ sensitive to radiation into the radiation passage region.

[Positioning in Step S7e]

In the case where a serious positional deviation occurs, the operator moves a patient or bed 9 so as to match the position in the therapeutic plan.

Detection of a positional deviation is not limited to the visual check of the operator but can be also automatically performed on the basis of a predetermined marker position on an image, the contour of an organ, a feature amount, or the like. In the case where the invention is not limited to the visual check of the operator but in any of visual detection and automatic detection, if a serious positional deviation is detected, to prevent a medical accident, desirably, the controller warns the operator, or the irradiation system 2 is locked so as not to operate.

[Irradiation in Step S6e]

When the position of the patient and the therapeutic plan coincide, in response to an operation of depressing a button or the like of the operator, the data acquisition controller 4 drives the irradiation system 2 to emit radiation to the patient on the basis of the therapeutic plan.

[Recording of Measured Irradiation Position and Measured Absorption Dose in Step S8e]

At the time of emitting radiation from the irradiation system 2, the data acquisition controller 4 controls the scattering radiation detection system 3 and measures the irradiation position of the radiation emitted from the irradiation system 2 to the patient and the scattering radiation dose generated by the irradiation. The data processing system 5 obtains the measured irradiation position and measured absorption dose from the measured scattering radiation dose by the conversion processor 505. The measured irradiation position and the measured absorption dose are time-sequentially stored in the storage unit 7 as shown in FIGS. 34A and 34B. They can be also expressed by an absorption dose distribution diagram as shown in FIG. 35.

Figure 36:
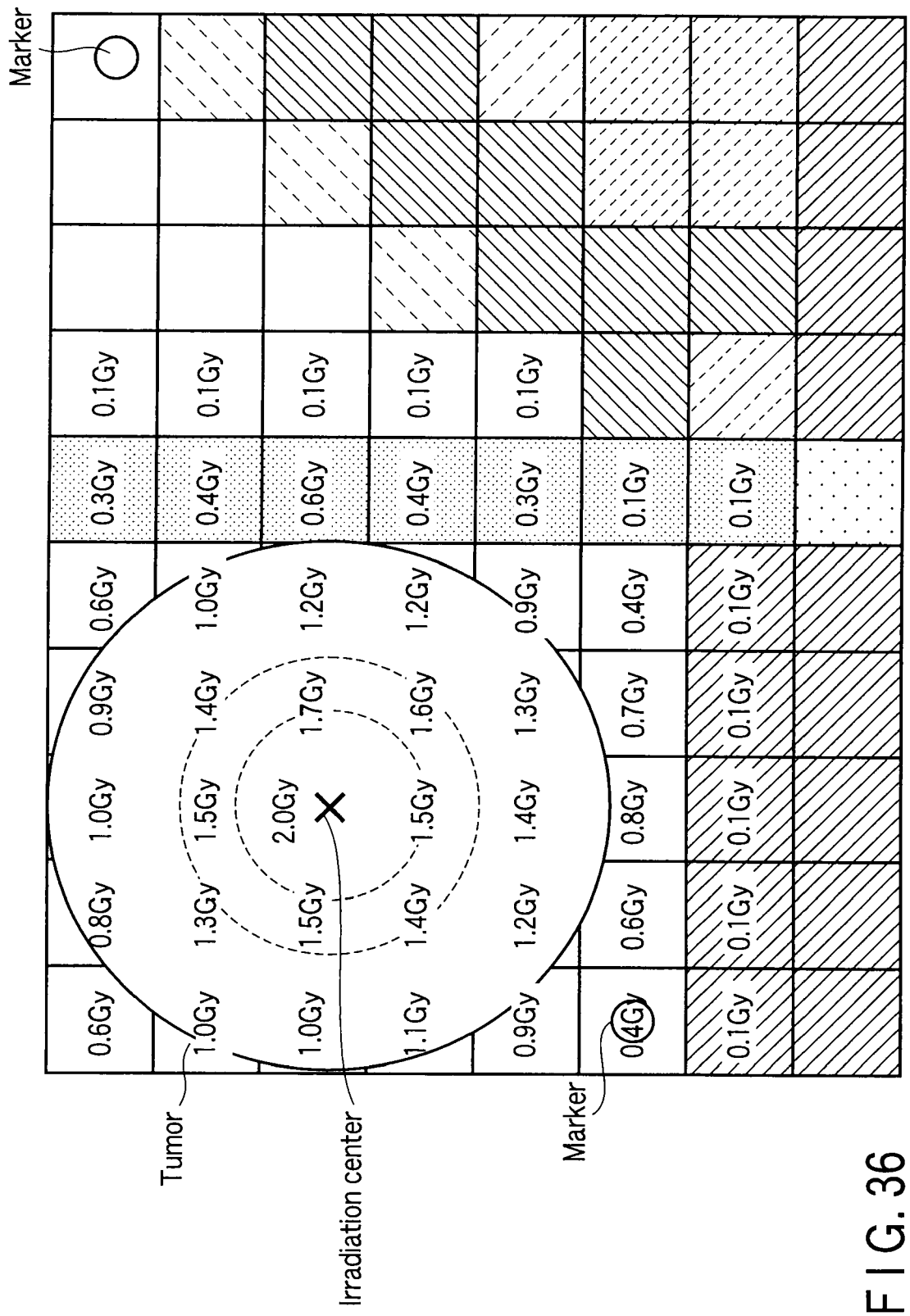
FIG. 36 is a diagram showing an example of an image obtained by superimposing a therapy result and a therapeutic plan image on the image just before therapy.
Figure 37:
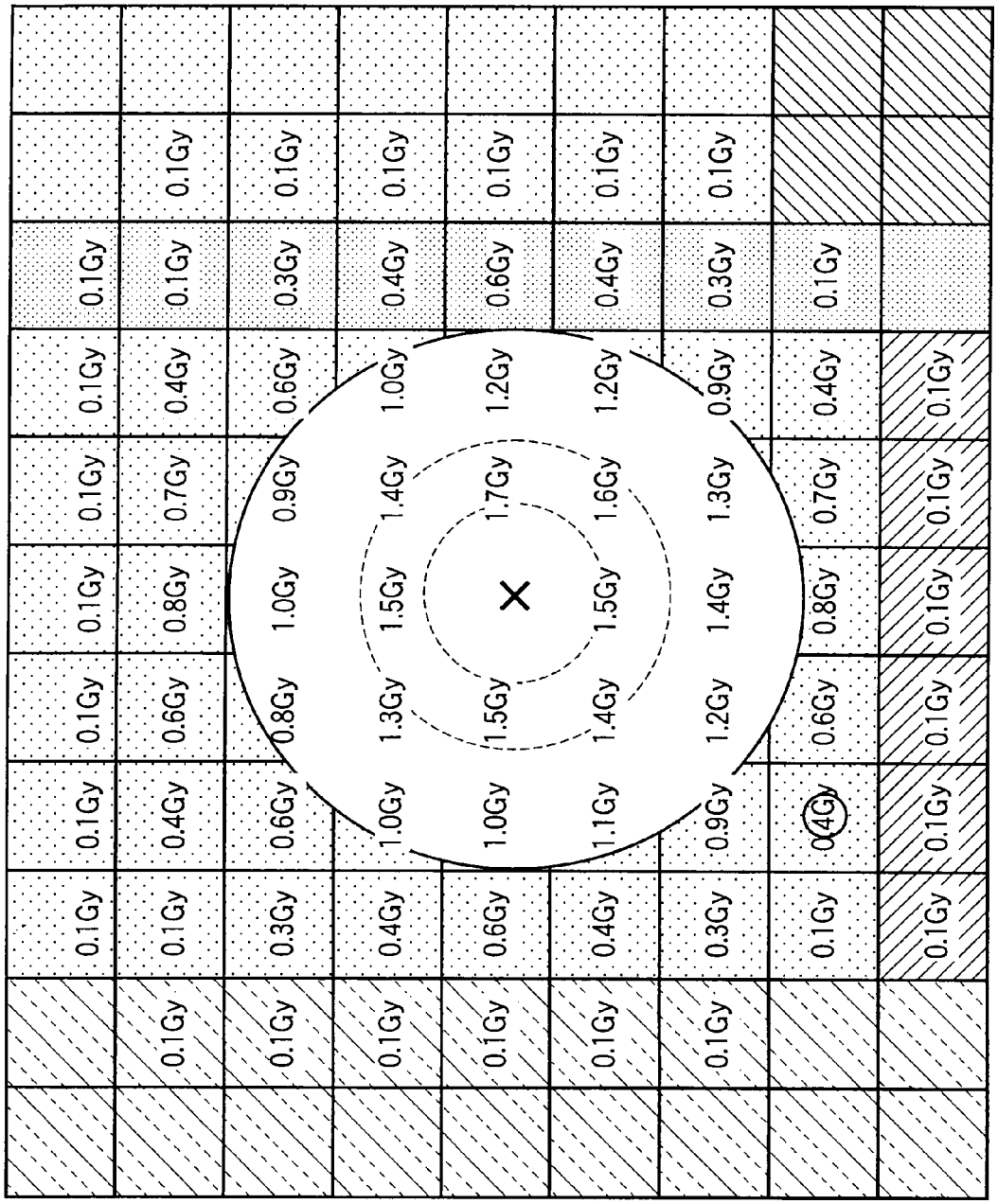
FIG. 37 is a diagram showing an example of an image obtained by superimposing a therapy result and a therapeutic plan image on the image just before therapy.
Figure 38:
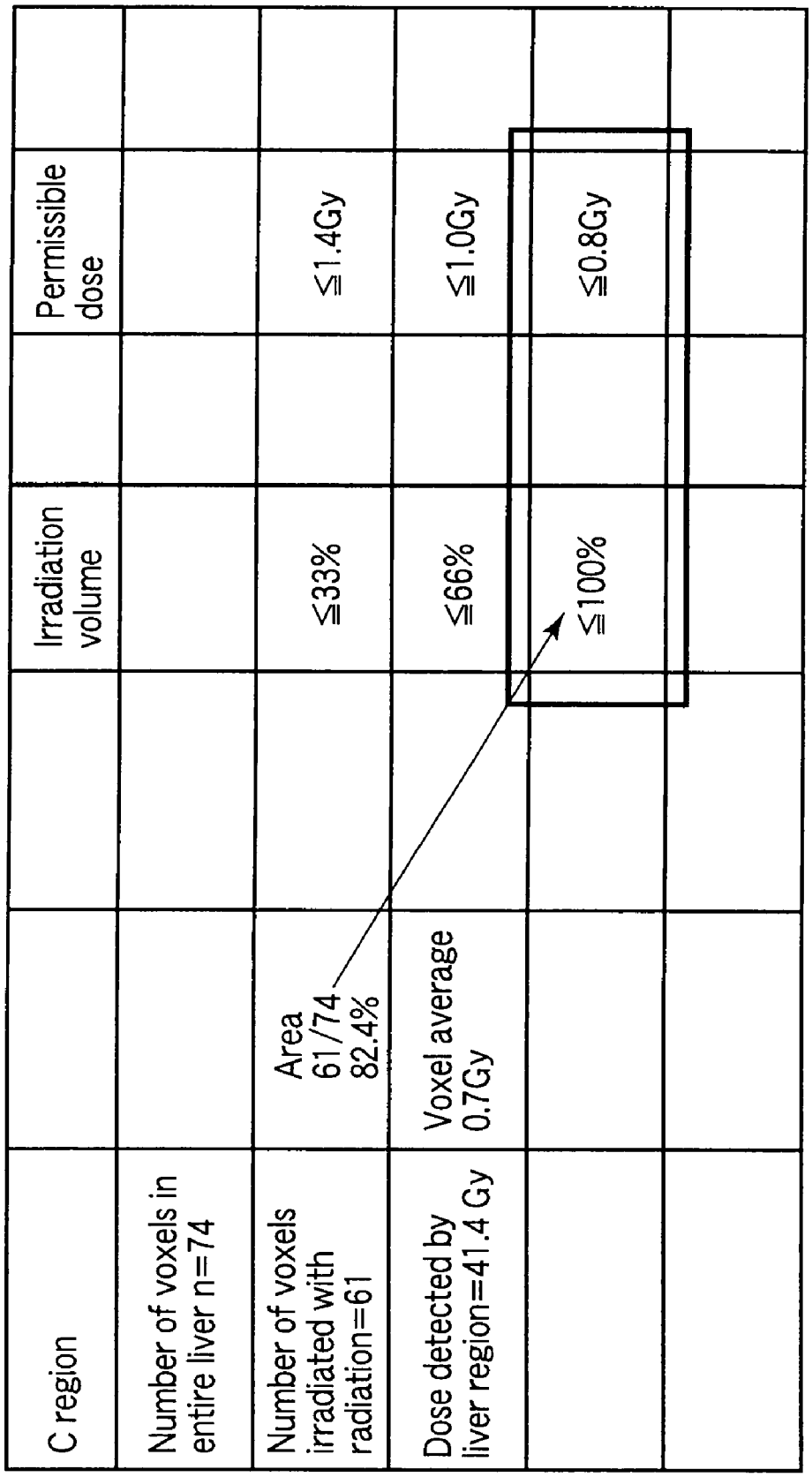
FIG. 38 is a diagram showing an example of a determination procedure in the case of a liver region.
Figure 39:
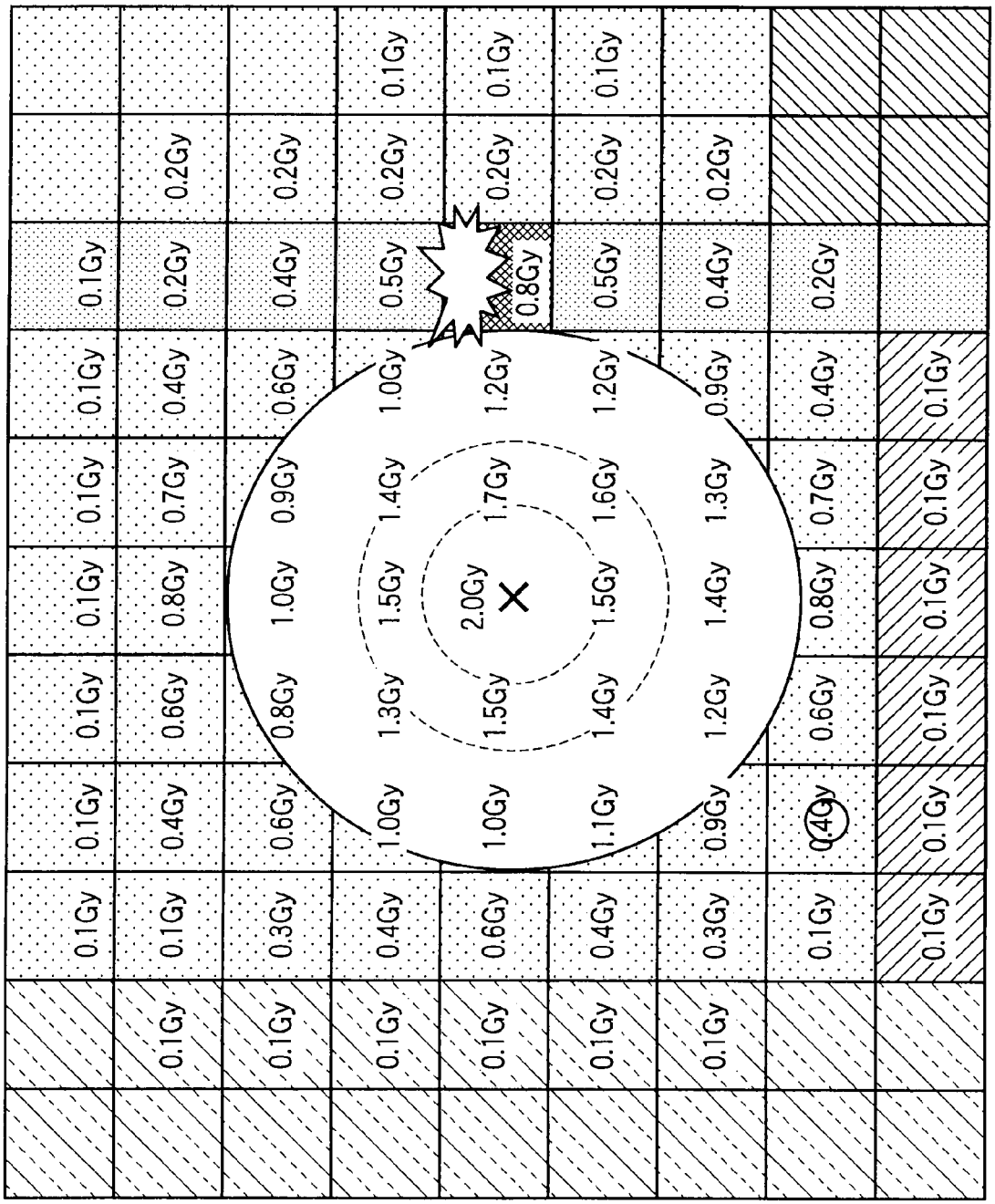
FIG. 39 is a diagram showing an example of warning display when an actually measured absorption dose exceeds a permissible range.

An image obtained by superimposing the therapy result (measured irradiation position and measured absorption dose) and the therapeutic plan image stored in the storage unit 7 on the image captured just before treatment is displayed on the display of the display unit 6 (FIGS. 36 and 37). The plan evaluation module 513 determines the difference from the scheduled irradiation dose which is set in each of the voxels and whether the dose does not exceed the permissible dose or not. As an example, the determination procedure in the case of a liver region in the table of FIG. 38 will be described. When an abnormal state such that the absorption dose measured exceeds the permissible range is found in the determination, a warning is given by light, sound, or character display as shown in FIG. 39 to promote awareness of the operator.

[Immediately Preceding Image Capturing 2 in Step S9e]

After completion of the irradiation, the plan evaluation module 513 captures again an image just before therapy of the patient. Since there is a case that a positional deviation occurs due to deformation of an organ during therapy in addition to motion of the patient due to insufficient fixing, it is desirable to check the surrounding of an object to be treated almost in real time in order to perform accurate therapy. When it is determined that an object to be treated is deviated out of the permissible range, the therapeutic operation of the irradiation system 2 has to be stopped, and the patient or bed has to be moved to a correct position.

[Confirmation of Influence of Irradiation of Next Time in Step S10e]

Figure 40:
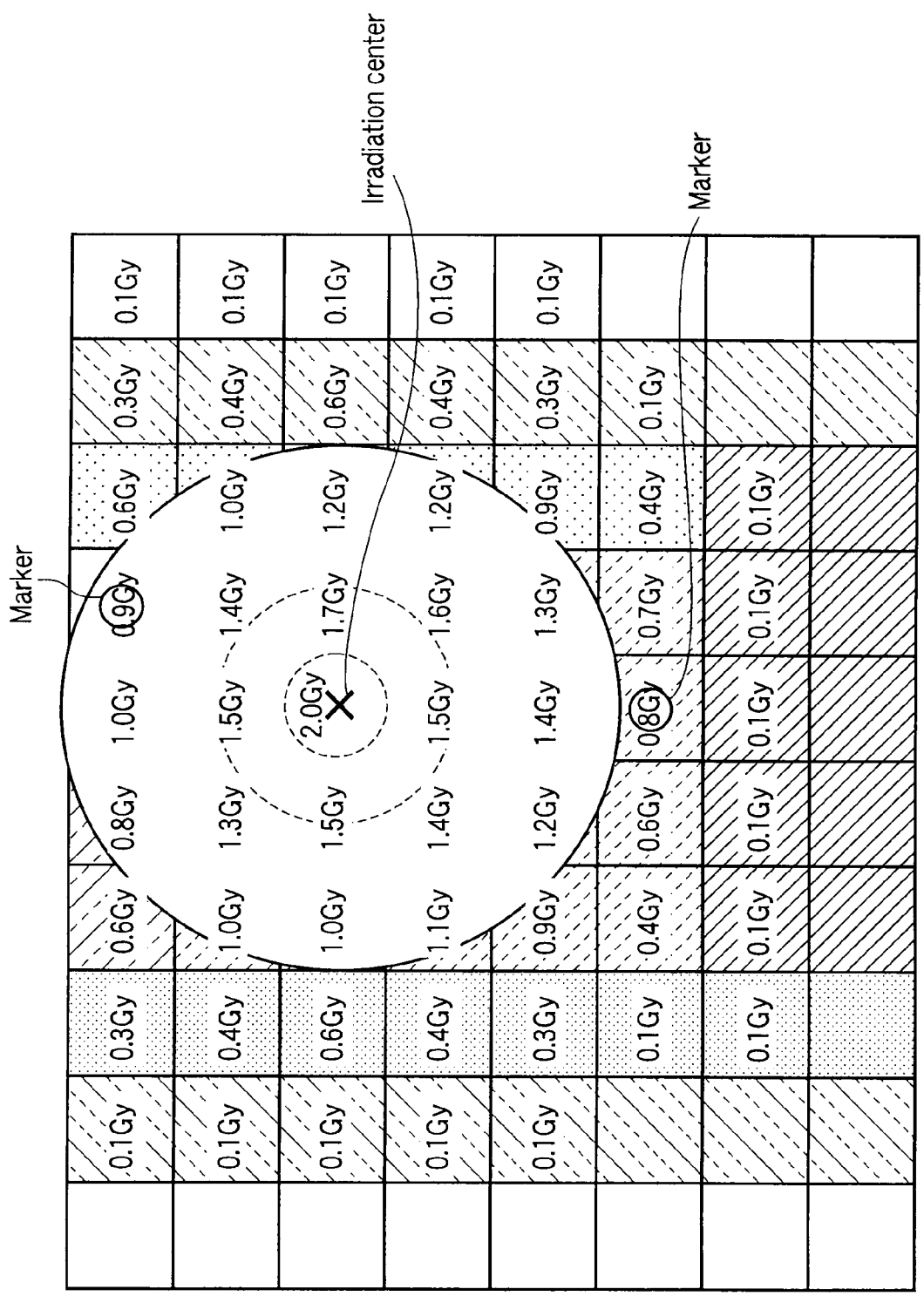
FIG. 40 is a diagram showing the influence of a therapeutic plan image of irradiation of next time.
Figure 41:
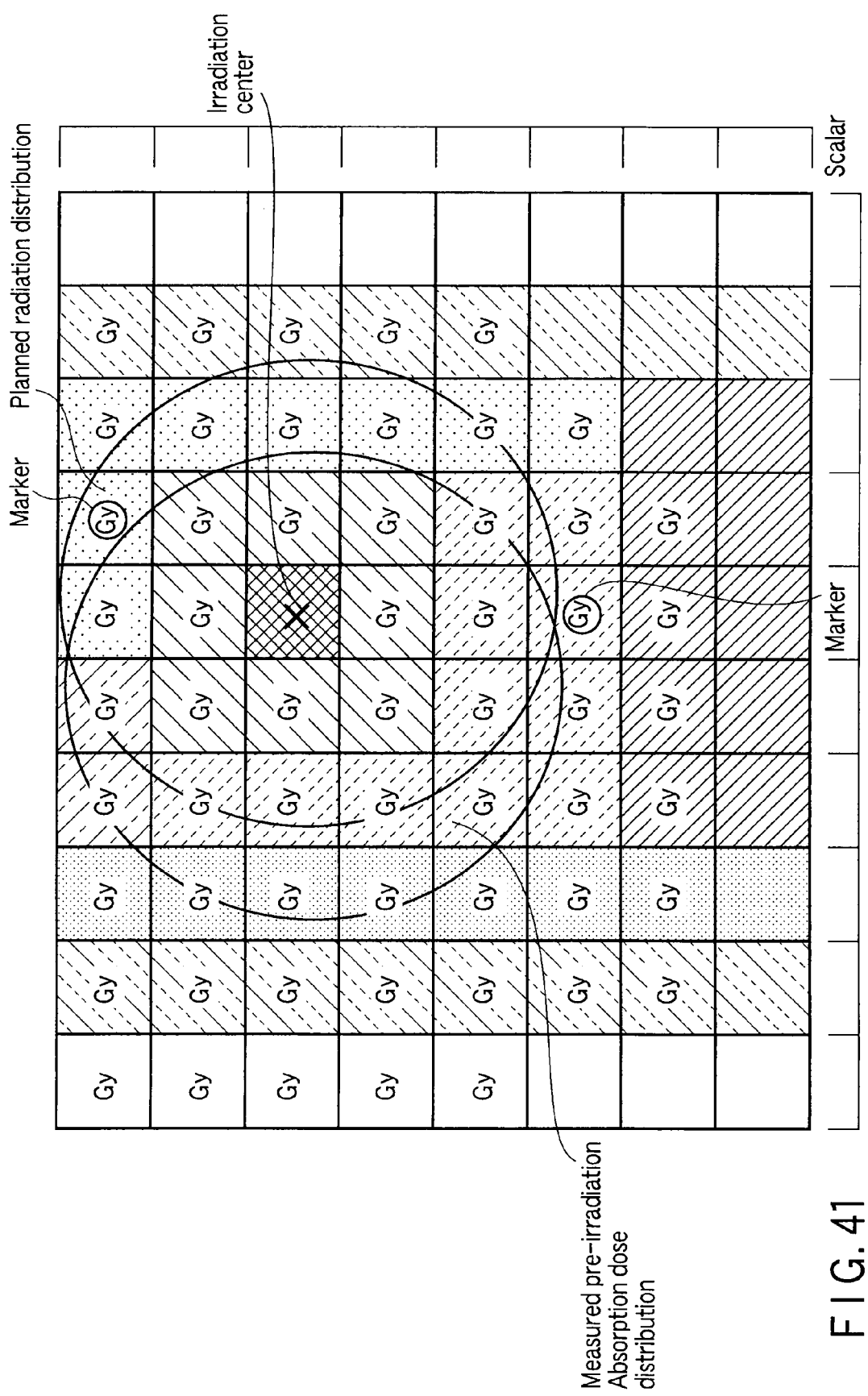
FIG. 41 is a diagram showing an example of an image obtained by superimposing a therapeutic plan image and a measured absorption line image.

FIG. 40 shows a therapeutic plan image of the second time. Numbers show distribution of scheduled radiation to be irradiated next. By overlapping the immediately preceding image (kv image) of the second time on the therapeutic plan image of the second time, a positional deviation can be confirmed. Next, radiation which is weak enough not to exert influence on the therapy is irradiated from the irradiation system 2 to the next irradiation planned position in the patient (pre-irradiation). The irradiation position is measured by the scattering radiation detection system 3. Whether or not there is a deviation between the plan and the measured position is determined by comparison between the therapeutic plan image and the measured absorption line image (FIG. 41).

A deviation may be automatically determined by the plan evaluation module on the basis of values on an image such as a CT value. A scalar may be displayed on an image so that a deviation amount can be visually confirmed. In the case where it is determined that the next irradiation plan is improper due to an uncorrectable deviation or the like, the operator selects whether the therapy is continued, the therapy is temporarily stopped, or the therapeutic plan is changed.

In such a manner, by confirming an actual irradiation state during the therapy and executing the irradiation while checking with the irradiation plan, accurate and safe radiotherapy treatment can be performed. Additionally, failure of irradiation of a region to be treated and excessive irradiation of the normal region can be reduced.

(Plan Update Module)

The processes of the plan update module 515 will be described.

FIRST EXAMPLE

In a first example of the plan update module 515, the irradiation plan is evaluated in consideration of the measured absorption dose, and optimum irradiation conditions (position and output dose) of the irradiation unit 203 in the irradiation system 2 are presented to the operator.

In the following, an irradiation dose denotes a dose of radiation from an irradiation head, an absorption dose denotes a dose absorbed by a human tissue, and an accumulated dose denotes total sum of the absorption dose of a certain tissue.

In FIG. 42, variables are defined as follows.

A: output of the irradiation system 2 (value in the k-th irradiation)

$r_{exposure}$: position of the irradiation head of the irradiation system 2 (value in the k-th irradiation)

u: direction of the irradiation head of the irradiation system 2 (value in the k-th irradiation)

r: vector to an arbitrary voxel in the coordinate system $f_j(r_j)$: absorption dose (measured value) at arbitrary voxel w: mass of each of the voxels R: vector to center of gravity of element μ: absorption coefficient distribution of irradiation region (vector in which values of all of voxels are arranged)

μ is obtained by, for example, a pixel value of the plan CT.

(Method of Grasping Actual Absorption Dose)

[Definition of Absorption Dose]

Main organs and tissues are extracted from a medical image of a CT, MRI, or the like captured in real time, and are segmented, and a target tumor (region to be treated) and a risk organ (risk region) are defined.

The segmented target tumor and risk organ are meshed to M elements. The meshing is performed so that the elements have sizes which are regarded as uniform. Since there are seven variables (A, $r_{exposure}$, and u which will be described later), the number of meshing items is seven or more. Since the absorption dose of a voxel in $r_i$ is defined as $f_j(r_i)$, an average absorption dose of the i-th element whose gravity center position $R_i$ is expressed as follows $$\vec{R}_i = \frac{1}{M} \sum w \cdot \vec{r}_j \quad \text{Equation (1)}$$

is defined as follows using a value obtained by multiplying the absorption dose of each of voxels included in the element by the mass of each voxel and performing weighted averaging on the value.

$$F_i = \frac{1}{M} \sum f_k(\vec{r}_k) \quad \text{Equation (2)}$$

[Identification of Structure]

In the case of determining the irradiation dose in the irradiation plan, the dose absorbed (absorption dose) by the structures (main tissue, risk organ, and the like) up to last time has to be considered. To determine the past absorption dose of each of the structures, the position of the structure has to be traced. For example, when a structure moves (rotate and translate) and is deformed as shown in FIG. 43, the structure region of last time is meshed. The outline of the structure of last time is adjusted by transfer and deformation so as to be overlapped with the outline of the structure of this time (the node points on the outline of the structure of last time are overlapped on the structure of this time). The volume of the structure of last time and that of the structure of this time are compared with each other, and the positions of the node points in the structure of this time are determined so that variations in the volume enlargement/reduction ratios of the elements become minimum. By the operation, the absorption doses of the elements can be traced.

(Crossfiring Plan Generation Method)

[Various Evaluation Criteria]

The total number of irradiation times of today is set to K. Actual absorption dose up to the n-th irradiation is $F_i$ and target dose of a tumor region in all of the K irradiations of today is $d_{tumor}$.

[Condition 1: Evaluation of Dose of Tumor Tissue]

The absorption dose in the entire region of tumor has to exceed $d_{tumor}$. When the absorption dose distributions of the n+1-th to K-th irradiations are $E^k_i (A, r_{exposure}, u, \mu)$, to set the absorption dose of the tumor tissue equal to or larger than the target dose $d_{tumor}$, the following equation has to be satisfied in all of the region i where $r_i \in \Omega_{tumor}$ ($\Omega_{tumor}$ expresses the tumor region), that is, in all of segments belonging to the tumor region.

$$F_i + \sum_{k=n+1}^{K} E^k_i(A, \vec{r}_{exposure}, \vec{u}, \vec{\mu}) \geq d_{tumor} \quad \text{Equation (3)}$$

[Condition 2: Evaluation of Irradiation Dose of Risk Organ]

Also in the irradiation dose of a risk organ, like the irradiation dose of a main tissue, the absorption dose is evaluated. When the absorption dose distributions of the n+1-th to K-th irradiations are $E^k_i (A, r_{exposure}, u, \mu)$, to suppress the absorption dose of the risk organ to be less than the permissible dose $d^j_{riskOrgan}$, each of the elements included in the segments of the risk organ has to satisfy the following equation with respect to all of the region i where $r_i \in \Omega^j_{riskOrgan}$.

$$F_i + \sum_{k=n+1}^{K} E^k_i(A, \vec{r}_{exposure}, \vec{u}, \vec{\mu}) < d^j_{riskOrgan} \quad \text{Equation (4)}$$

where $\Omega^j_{riskOrgan}$ denotes the region of the j-th risk organ in the plurality of risk organs.

[Condition 3: Evaluation of Irradiation Dose of Risk Organ (No. 2)]

Even when the absorption dose exceeds the permissible accumulated dose in a limited partial region in a risk organ, it does not mean that all of the functions disappear. Another criterion of the radiation dose to a risk organ may be a criterion that "the survival rate of cells of a risk organ is a predetermined value or larger". The residual function (function residual ratio) of a risk organ is evaluated by the following equation.

$$S^j_{riskOrgan}(A, \vec{r}_{exposure}, \vec{u}, \vec{\mu}) = \quad \text{Equation (5)}$$

$$\frac{\sum_{\vec{r}_i \in \Omega^j_{riskOrgan}} V_i p^j_{riskOrgan} \left( F_i(\vec{R}_i) + \sum_{k=n+1}^{K} E^k_i(A, \vec{r}_{exposure}, \vec{u}, \vec{\mu}) \right)}{\text{Volume}(\vec{r}_i \in \Omega^j_{riskOrgan})}$$

where Vi denotes volume of the region "i", and $p_{riskOrganA}(F)$ denotes the probability that cells of tissue of a risk organ "j" irradiated with the absorption dose F survive. Volume($r_i \in \Omega^j_{riskOrgan}$) shows the sum of volumes of corresponding regions.

Further, when the residual function rate of the risk organ "j" necessary for maintaining the living body is defined as $\text{rate}^j_{survive}$, whether the irradiation method is proper or not can be determined depending on whether the following equation is satisfied or not. If inequality is satisfied, irradiation using A, $r_{exposure}$, and u at that time is possible. $\text{rate}^j_{survive}$ is a value which is set at the time of planning.

$$S_{riskOrgan}^J(A, \vec{r}_{exposure}, \vec{u}, \vec{\mu}) \geq \text{rate}_{survive}^J \quad \text{Equation (6)}$$

(Irradiation Method Determination Method)

Using the evaluation criteria (conditional expressions 1 to 3), the irradiation method is determined on the basis of the following principle.

In the combination of A, $r_{exposure}$, and u satisfying the conditional expressions 1 to 3, A, $r_{exposure}$, and u maximizing the function residual rate $S^j_{riskOrgan} (A, r_{exposure}, u, \text{ and } \mu)$ are obtained. A, $r_{exposure}$, and u also have to satisfy the conditions of the designing of the apparatus, geometric constraints (arm length), and maximum output of the irradiation system 2. A, $r_{exposure}$, and u are the irradiation conditions of the k-th irradiation. All of irradiation conditions of K-n times from the n+1-th irradiation to the K-th irradiation have to be determined.

First, using the conditional expressions 1 to 3 and the design conditions of the apparatus as constraints, L combinations of A, $r_{exposure}$, and u which can be irradiated are obtained and set as $C_l$ (l=1, ..., L). As a concrete method, K-n times of irradiation conditions A, $r_{exposure}$, and u generated by random number are examined with the conditional expressions 1 to 3 and the design conditions, and a condition which passes the examination is set as $C_l$. By using the L conditions, the following equation is calculated.

$$s_l = \min_j \left( \frac{S^j_{riskOrgan}(\vec{C}_l, \vec{\mu})}{rate^j_{survive}} \right) \quad \text{Equation (7)}$$

$C_l$ having the maximum value in $S_1$ is presented as an optimum protocol of the irradiation plan to the user. $\min_j (\ldots)$ represents that the minimum value is obtained from values in the parenthesis in plural "j".

(Irradiation Plan Update)

[Step 1: First Irradiation Plan]

As L, (for example), a large number of about 100,000 is used. By using the above-stated crossfiring plan generation method, an irradiation plan is generated. At this time, K items of $E^k_i$ (A, $r_{exposure}$, u, μ) have to be calculated on all of the 100,000 irradiation conditions $C_l$. The calculation can be executed by using a known computer simulation method. In this step, all of K irradiation conditions are once determined. As K, for example, a relatively small value such as ten is set. In the initial irradiation plan, the number of irradiations finished is zero, so n=0 is set.

[Step 2]

The irradiations of the K irradiation conditions are executed and the absorption dose distribution is measured (pre-irradiation). To reduce the exposure dose, it is necessary to set the output A to hundredth part of the actual output and multiply the measured absorption dose with the inverse.

[Step 3]

In the first irradiation condition (k=1), a predicted dose $E^1_i$ (A, $r_{exposure}$, u, and μ) on execution of the irradiation is displayed on the screen. $E^1_i$ (A, $r_{exposure}$, u, and μ) displayed at this time is obtained in the step 2.

[Step 4]

Irradiation is executed in the irradiation condition of the first time.

[Step 5]

The actual absorption dose in the irradiation of the first time is measured (n=1).

[Step 6]

The actual absorption dose in the first time is used, and the irradiation plan of the second time on is re-generated. At this time, a value which is about a few times as large as K is used as L. Since much smaller value than 100,000 kinds used for the initial calculation is used, the calculation is executed at high speed, and can be executed in short time of irradiation. When the irradiation condition determined for the first time is set to $C^1$, it is sufficient to select, as $C_l$ used for the irradiation plan of the second time, from values close to $C^1$. By using such a selection method, the irradiation plan updated after the irradiation of the first time is a minor correction from the irradiation plan of the first time. Although $E^k_i$ (A, $r_{exposure}$, u, and μ) is obtained by simulation in the initial irradiation plan, in the second or subsequent irradiation plans, $E^k_i$ (A, $r_{exposure}$, u, and μ) is obtained by simulation and using measurement values of the pre-irradiation. Specifically, a change in the absorption dose distribution for a small correction is obtained by simulation. By applying same deformation to the absorption dose measured in the step 2, "K-n" items (from k=n+1 to k=K) predictive doses $E^k_i$ (A, $r_{exposure}$, u, and μ) are obtained for each of the L items of irradiation plan candidates $C_l$. Since the irradiation is finished once, n=1.

[Step 7]

The irradiation condition (k=2) of the second time and the predicted dose for executing the irradiation are displayed on the screen.

[Step 8]

The irradiation is executed under the irradiation condition of the second time.

[Step 9]

The actual absorption dose in the irradiation of the second time is measured, and accumulated dose obtained by adding the actual absorption doses of the first and second times is calculated (n=2). To obtain the accumulated dose, the above-described fusion model is used.

[Step 10]

In a manner similar to step 6, the irradiation plan of the third time or later is re-generated.

[Step 11]

Similarly, the irradiation is executed to the K-th irradiation.

Figure 49:
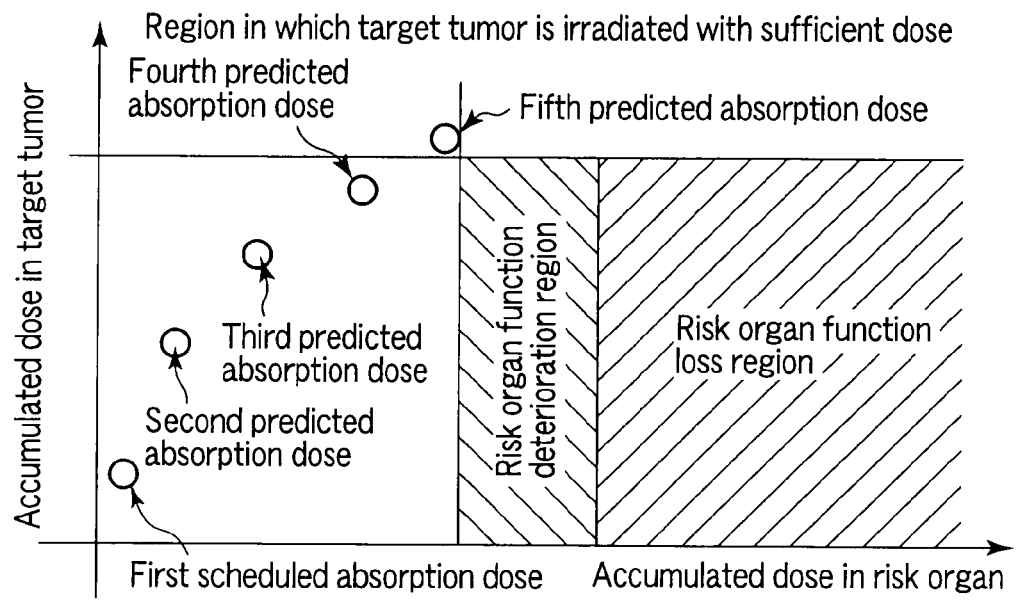
FIG. 49 is a diagram showing accumulated doses of a tumor and a risk organ.

During the irradiation therapy, screen display is performed as will be described below. A doctor watches the screen and determines whether the irradiation process advances as planned or not. When a large error occurs in the plan due to an error in the set X-ray absorption coefficient, large movement of the patient during the irradiation process, and the like, for example, the predicted accumulated dose in a risk organ may exceed the permissible dose as shown in FIG. 49. In such a case, the irradiation plan is re-generated by a method similar to step 1, not step 6. In this case, the irradiation plan can be largely changed in consideration of the accumulated dose different from the small correction from the initial plan. Thus, the irradiation plan in which the predicted accumulated dose in a risk organ becomes the permissible dose or less can be found.

(Irradiation Plan Update Flow)

Figure 44:
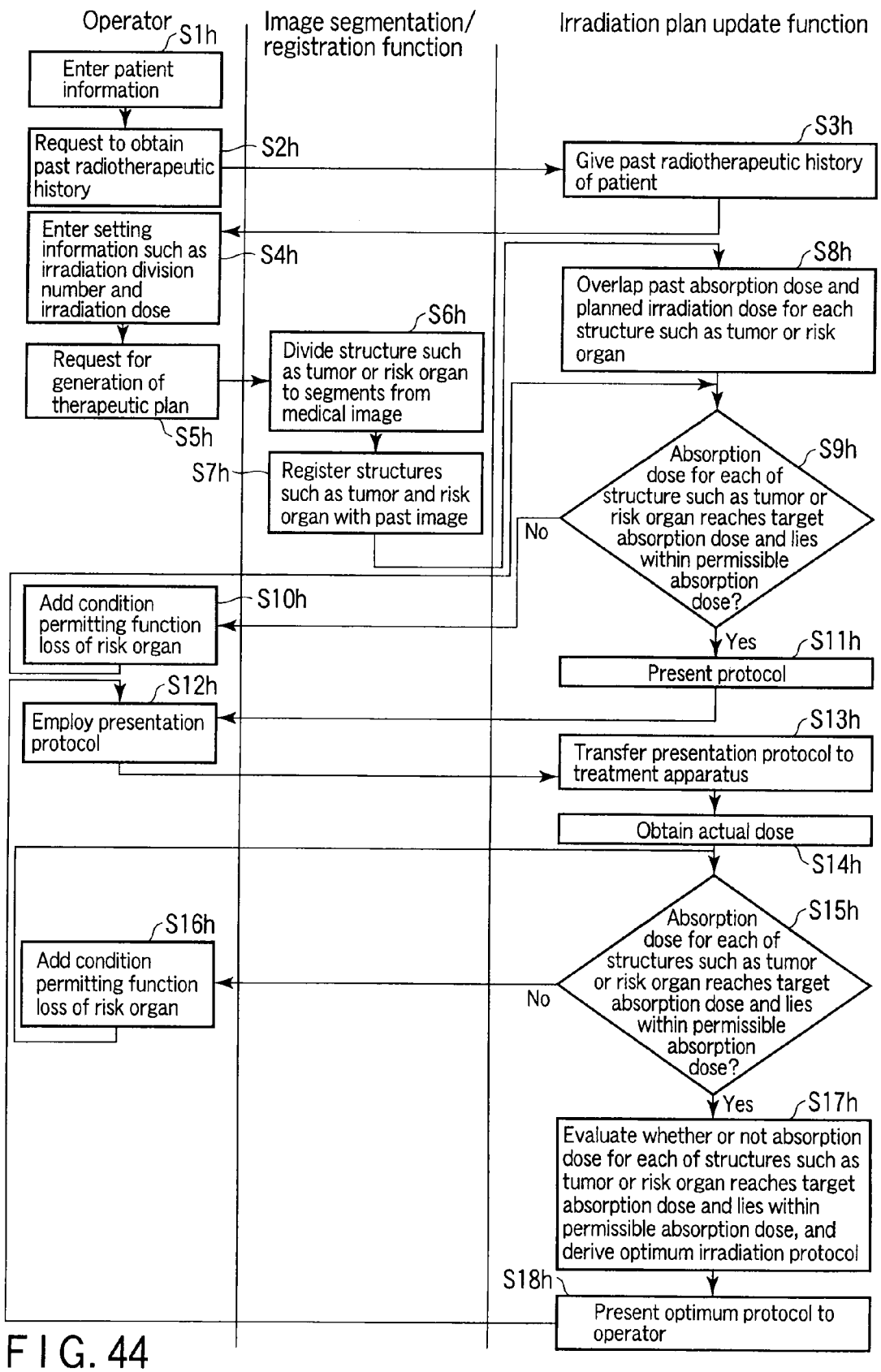
FIG. 44 is a flowchart showing the procedure of an irradiation plan update process.

FIG. 44 is a flowchart showing the procedure of the irradiation plan update process in the plan update module 515.

The operator enters patient information by the operating unit 8 (step S1h) and requests for acquisition of a radiotherapy record (step S2h). On receipt of the request, the plan update module 515 reads the radiotherapy record of the patient from the storage unit 7 and outputs it on the display unit 6 (step S3h).

The operator enters setting information such as the number of irradiation division times, irradiation dose, and the like (step S4h), and requests for generation of a therapy plan (step S5h). The plan update module 515 segments a structure such as a tumor or a risk organ in a medical image (step S6h). The plan update module 515 registers the structure such as tumor and risk organ segmented together with past images (step S7h).

The plan update module 515 overlaps the past absorption dose and the planned irradiation dose for each of the structures such as tumor and risk organ (step S8h). The plan update module 515 determines whether the absorption dose reaches the target absorption dose and remains within the permissible absorption dose or not for each of the structure such as tumor and risk organ (step S9h). When the conditions are not satisfied in the determination, the fact is presented in the display unit 6, and the operator adds, for example, a condition of permitting a function loss of a risk organ (step S10h). The plan update module 515 performs the determination in step S9h again and, when the conditions are satisfied, the plan update module 515 presents a protocol (step S11h).

A result of the determination of whether the irradiation plan satisfies the conditions or not and presentation of the protocol satisfying the conditions are performed as follows. The plan update module 515 obtains the total of the accumulated dose and the prediction dose and displays it on the screen with respect to each of the three cases; the case where the plan is not corrected, the case of slightly correcting the plan by the method of step 6, and the case of changing the plan by the method of step 1. On the screen, results of the determination of whether the conditions are satisfied or not are presented for the three cases. The operator refers to the displayed images and the determination results, determines one of the three protocols to be employed, and selects the protocol to be employed by the operating screen. The image displayed in the method of step 1 and the determination result may not be displayed initially but may be displayed in accordance with an operation of the user.

When the presentation protocol is employed by the operator (step S12h), the plan update module 515 transfers the presentation protocol to the data acquisition controller 4 (step A13h). The plan update module 515 obtains the reconstructed absorption dose distribution (step S14h), and determines whether the absorption dose of each of the structures such as tumor and risk organ reaches the target absorption dose and is within the permissible absorption dose or not (step S15h). When the determination conditions are not satisfied, the operator adds a condition of permitting the function loss of the risk organ again (step S16h).

When the determination conditions are satisfied, the plan update module 515 evaluates whether the absorption dose reaches the target absorption dose and lies within the permissible absorption dose or not for each of the structures such as tumor and risk organ, and derives the optimum irradiation protocol (step S17h). The plan update module 515 presents the derived protocol as the optimum protocol to the operator (step S18h).

(Display GUI Image)

Figure 46:
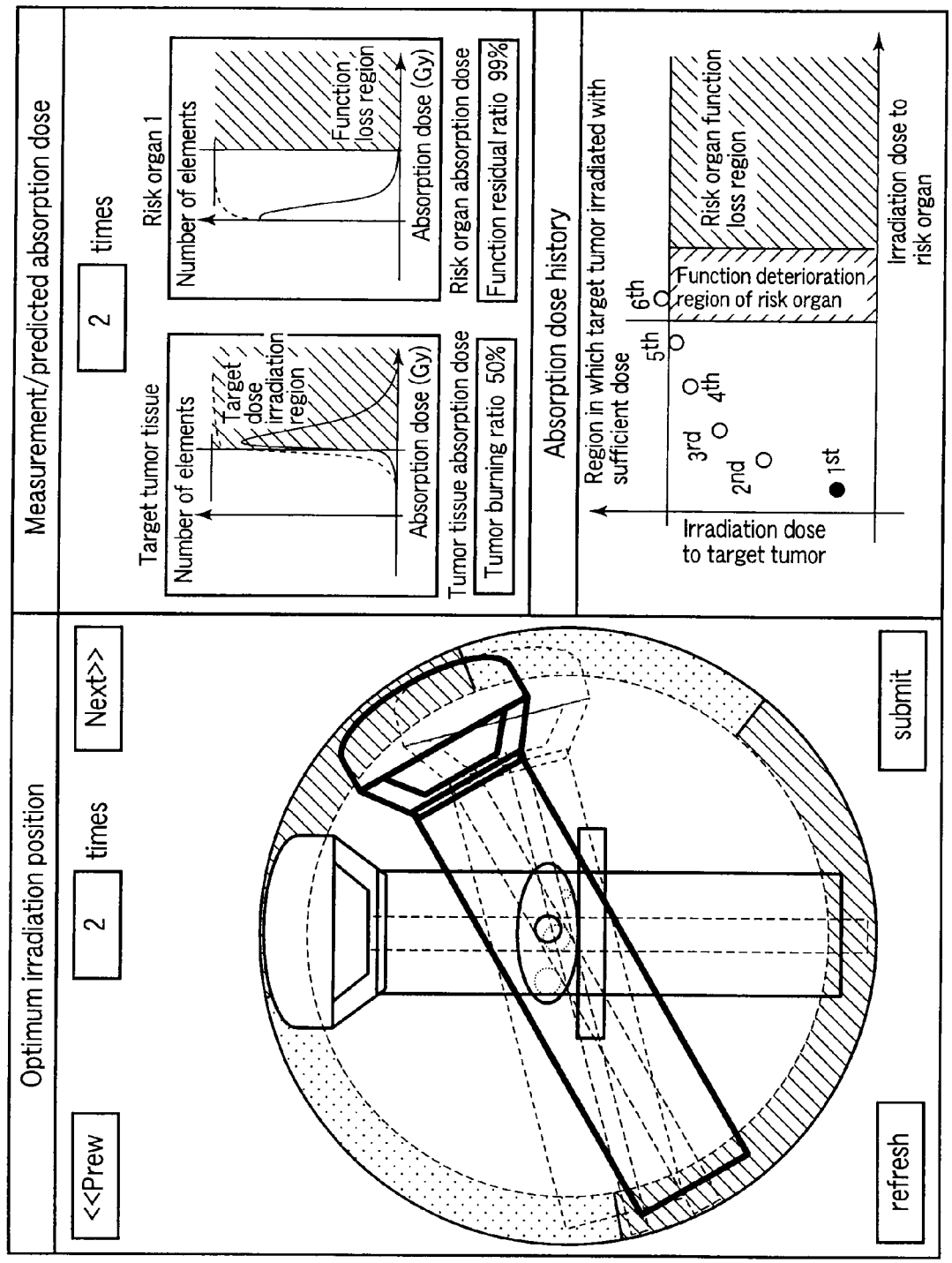
FIG. 46 is a diagram showing an example of the screen image displayed in the display unit.

FIGS. 45 and 46 show screen configuration examples of a GUI image displayed on the display unit 6.

Before treatment starts, the operator enters a patient ID and patient name and requests for past radiotherapeutic data. As the radiotherapeutic data, the absorption dose of each of elements of the risk organ and the absorption dose of each of elements of each of tumor tissues are requested.

[Past Therapy Record]

At the time of display, the absorption dose of each of the elements included in a risk organ is multiplied with the weight of the element, and the weight-averaged absorption dose is displayed as the absorption dose of the risk organ. Similarly, the weight-averaged absorption dose is displayed as the absorption dose of the tumor tissue.

The permissible limit of the risk organ is set manually or automatically (by taking a numerical value from a reference value database determined by guidelines or the like). The number of times of irradiation and the irradiation dose of this time are set, and generation of a plan is requested.

[Setting of Allowable Limit of Risk Organ]

In the case of automatic setting, the predetermined permissible accumulated dose and the function residual ratio are displayed.

A permissible function residual ratio is used as the permissible limit (rate$_{survive}$) when the risk organ is exposed in any of irradiation beam paths. The function residual ratio is expressed by an occupation ratio of elements which do not exceed the permissible accumulated dose in all of the elements included in the risk organ.

[Setting of The Irradiation Division Number and Dose]

Conditions for generating a therapeutic plan are entered.

[Presentation of Crossfiring Plan]

A protocols satisfying the conditions and optimum by evaluation of the planned dose is displayed (after irradiation, an update request is made to obtain the absorption dose of last time, and the optimum protocol is generated by using the crossfiring plan generation process and displayed).

To visually confirm the expected effects of a designated angle (or record after irradiation) and the protocol, "irradiation optimum position", "measured/predicted absorption doses", and "absorption dose history" are displayed.

[Display of Irradiatable Range]

FIG. 47 is a diagram showing an irradiation position presentation method. The irradiation position/region satisfying the evaluation of the planned dose is divided into a region where a risk organ is damaged and a region where sufficient dose can be given to a tumor tissue by color. When a treatment apparatus in the diagram is dragged and rotated, "measured/predicted absorption dose" and "absorption dose history" according to the irradiation position are displayed. Consequently, the operator can confirm the effect. In the case where the operator performs irradiation from the position to which the treatment apparatus in the diagram is dragged, the operator depresses a "submit" button so as to be reflected in the "crossfiring plan" (the operator can perform manual operation). By performing "update" in the "crossfiring plan", the subsequent plan is updated on the basis of the irradiation position designated by the operator.

[Absorption Dose and Residual Function of Each Structure]

FIGS. 48A and 48B are diagrams showing the relation between the absorption dose and the number of elements in tumor and risk organ. The fatality or survival rate may be displayed. A planned value per irradiation may be displayed or a planned value after completion of all of irradiations scheduled today may be displayed. Naturally, when irradiation is actually performed, a measurement value is displayed. The measured value of the irradiation performed already and planned values of the remaining irradiations may be displayed. By the display, whether a final goal can be achieved or not can be known in the middle.

[Display of Absorption Dose History]

Accumulated doses (both predicted and measured values) in tumors and risk organs are displayed. For example, just before irradiation, as shown in FIG. 49, predicted values from the first to fifth (final) irradiations are plotted. The dose for a tumor is sufficient and that for a risk organ is equal to or less than the permissible value.

Figure 50:
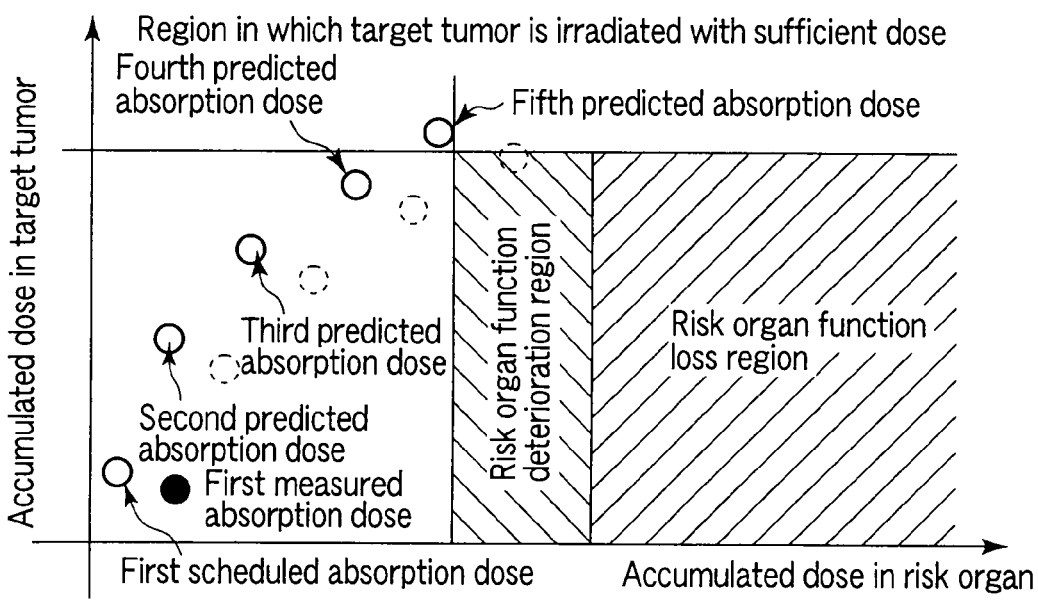
FIG. 50 is a diagram showing accumulated doses of a tumor and a risk organ.

FIG. 50 shows the case where the first irradiation is performed and a deviation occurs. A measured value of the first irradiation and predicted values for the second to fifth (final) irradiations are plotted and it is understood that if the irradiation is continued, the goal cannot be achieved. In such a case, the program returns to step (6) or (1) and corrects the plan.

The ratio of the tumor tissue (therapy achievement ratio) is defined as follows.

$$\frac{\text{Volume}\left(F_i + \sum_{k=n+1}^{K} E_i^k(A, \vec{r}_{exposure}, \vec{u}, \vec{\mu}) \geq d_{tumor}\right)}{\text{Volume}(\vec{r}_i \in \Omega_{tumor})} \quad \text{Equation (8)}$$

The ratio may be used for the vertical axis. "Volume( . . . )" expresses herein the sum of volume of the corresponding region.

As described above, in the first example, the irradiation plan evaluation function is generated in consideration of the past absorption dose, and the position of the irradiation unit 203 in the irradiation system 2 satisfying the evaluation function and the output dose are presented to the operator.

SECOND EXAMPLE

In a second example of the plan update module 515, a risk that a risk organ (risk region) is exposed to a radiation beam is evaluated. An irradiation plan is evaluated in consideration of a measured absorption dose, and optimum irradiation conditions (position and output dose) of the irradiation unit 203 in the irradiation system 2 are presented to the operator.

A risk that a risk organ is exposed to a radiation beam depends on a beam path and the disposition of the risk organ. As an evaluation index, therefore, the distance between the center of a radiation beam and the risk organ is considered. A beam path in which the sum of distances from elements included in the risk organ to the radiation beam is the maximum is proposed to the operator as an optimum beam path having the lowest risk that the risk organ is exposed to the radiation beam.

When there are a plurality of risk organs, a beam path in which the sum of distances from elements included in all of the risk organs to the radiation beam path is the maximum is proposed to the operator as an optimum beam path. For example, the distance from the j-th element included in an i-th risk organ shown in FIG. 51 to a beam path is expressed by the following equation.

$$|\vec{h}_{i,j}| = |\vec{h}_{i,j}(\vec{r}_{exposure}\ \vec{R}_{i,j}\ \vec{u})|$$

$$= \left|\vec{r}_{exposure} - \vec{R}_{i,j} + \frac{(\vec{R}_{i,j} - \vec{r}_{exposure}) \cdot \vec{u}}{|\vec{u}|^2}\vec{u}\right|$$

Equation (9)

The distance from all of elements in all of risk organs is $\Sigma\Sigma|h_{ij}|$, and the plan update module 515 presents the beam path ($r_{exposure}$ and u) whose distance is the longest to the operator. The plan update module 515 may obtain and present a path that maximizes $\min_{i,j}(h_{ij})$.

In the second example, a risk that a risk organ is exposed to a radiation beam is evaluated by the distance between the risk organ and the beam path. In such a manner, by numerically introducing a prevention region, a beam path reducing the risk that the risk organ is exposed to the radiation beam can be presented.

As described above, in the embodiment, a radiation absorption dose is displayed so as to be superimposed on a morphology image of an arbitrary section in real time. Thus, the user can promptly, easily, and visually confirm the radiation irradiated position and the absorption dose. Further, on the basis of the obtained absorption dose, information for evaluating a therapeutic plan in advance and treatment support information such as the optimum therapeutic plan can be obtained. Thus, whether the radiotherapy treatment is performed according to the therapeutic plan or not can be grasped during treatment. Insufficient irradiation of a region to be treated and excessive irradiation of a normal region in the periphery of the region to be treated can be prevented. As a result, the effect of the radiotherapy treatment can be improved, reduction in the amount of excessive exposure of the subject can be realized, and the invention can contribute to improve the quality of the radiotherapy treatment.

The present invention is not limited to the foregoing embodiments but can be embodied by modifying the components without departing from the gist at the time of carrying out the invention.

For example, in the foregoing embodiments, the data processing system is included in the radiotherapeutic system. The present invention is not limited to the configuration. The data processing system can be provided as a single radiotherapeutic support apparatus separately from the irradiation system, the scattering radiation detection system, and the like.

The functions in the embodiments can be also realized by installing a program for executing the process into a computer such as a work station and developing the program on a memory. The program which can make a computer execute the method can be stored in a recording medium such as a magnetic disk (floppy (registered trademark) disk, hard disk, or the like), optical disks (CD-ROM, DVD, or the like), a semiconductor memory, or the like and distributed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A radiotherapy support apparatus comprising:
    a conversion unit which converts scattering radiation data to absorption dose volume data indicative of a distribution of absorbed radiation dose, the scattering radiation data being obtained by detecting a scattering radiation which occurs on the basis of a radiotherapeutic beam emitted to a subject;
    a calculation unit which calculates survival rate or fatality rate from the absorption dose volume data on the basis of information expressing relations between the absorption dose in a region and the survival rate or the fatality rate of normal cell so as to be associated with a plurality of segments,
    a comparison unit which compares between the survival rate and a value which is set at a time of planning or between the fatality rate and the value so as to be associated with a plurality of segments, and
    an evaluation unit which evaluates a result of the comparison of the comparison unit, and outputs a warning or stops operation of a treatment apparatus in accordance with the evaluation result.

2. The apparatus according to claim 1, wherein the scattering radiation is back scattering radiation of the radiotherapeutic beam.

3. The apparatus according to claim 2, wherein the back scattering angle θ lies in the range of $120°\leq\theta\leq165°$.

4. The apparatus according to claim 1, wherein the absorption dose volume data indicates a three-dimensional distribution.

* * * * *